US006790975B2

(12) United States Patent
Ichimura et al.

(10) Patent No.: US 6,790,975 B2
(45) Date of Patent: Sep. 14, 2004

(54) AMINOSTYRYLANTHRACENE COMPOUND, SYNTHETIC INTERMEDIATE THEREOF, AND PROCESS FOR THE PRODUCTION THEREOF

(75) Inventors: Mari Ichimura, Kanagawa (JP); Tadashi Ishibashi, Kanagawa (JP); Shinichiro Tamura, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 09/980,323

(22) PCT Filed: Apr. 6, 2001

(86) PCT No.: PCT/JP01/03003

§ 371 (c)(1),
(2), (4) Date: Mar. 19, 2002

(87) PCT Pub. No.: WO01/77065

PCT Pub. Date: Oct. 18, 2001

(65) Prior Publication Data

US 2003/0149290 A1 Aug. 7, 2003

(30) Foreign Application Priority Data

Apr. 6, 2000 (JP) ........................................ 2000-104582

(51) Int. Cl.[7] ..................... C07C 255/52; C07C 211/54; C07F 9/02
(52) U.S. Cl. ....................... 558/207; 558/418; 558/419; 558/420; 558/378; 564/427; 564/393
(58) Field of Search .................................. 558/207, 418, 558/419, 421; 564/426; 428/690, 917

(56) References Cited

U.S. PATENT DOCUMENTS

| | | |
|---|---|---|
| 5,332,820 | 7/1994 | Duncia |
| 6,242,116 | 6/2001 | Tadashi et al. |

FOREIGN PATENT DOCUMENTS

| | | | |
|---|---|---|---|
| EP | 1 072 669 A2 | * | 1/2001 |
| EP | 1090911 | | 4/2001 |
| JP | 2-255789 | | 10/1990 |
| JP | 2000-12227 | | 1/2000 |
| JP | 2001-106657 | | 4/2001 |

OTHER PUBLICATIONS

"Application of DMSO Acidities to the Wittig Reaction with 6–Deoxy–6–formyl–B–cyclodextrin", Robert L. Ivy et al; J. Org. Chem 1997; vol. 62, No. 18, pp 6415–6416.

"Synthesis and Exploratory Photophysical Investigation of Donor–bridge–acceptor Systems Derived from N–substituted 4–piperidones", T. Scherer et al; Recl. Trav. Chim. Pays–Bas, 1993, vol. 112 No. 10, pp 535–548.

"Synthesis and Cation–mediated Electron Transfer in Intramolecular Fluorescence Quenching of Donor–Acceptor Podands: Observation of Marcus Inverted Region in Foward Electron Transfer Reactions", H. Jiang et al; The Royal Society of Chemistry, May 2000, Perkin 2; No. 5, pp. 925–930.

"Synthesis and Characterization of Dicyanoanthracene–tethered B–cyclodextrins", Brian K. Hubbard, et al, J. Chem. Soc. Perkin Trans 2, 1996, No. 55 pp. 1005–1009.

* cited by examiner

Primary Examiner—Robert W. Ramsuer
Assistant Examiner—Ebenezer Sackey
(74) Attorney, Agent, or Firm—Sonnenschein, Nath & Rosenthal LLP

(57) ABSTRACT

This invention is an aminostyrylanthracene compound represented by, for example, the following general formula [I]. This compound is produced by condensation from a corresponding aminobenzaldehyde and a phosphonic ester or phosphonium salt.

General formula [I]

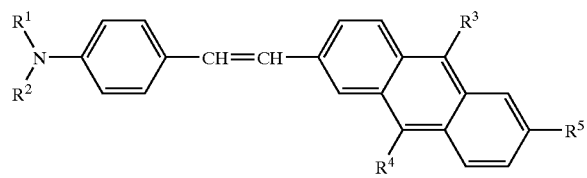

[where, in the general formula [I] above, $R^2$ represents an unsubstituted aryl group, $R^1$ represents an aryl group which may have a variety of substituents, and $R^3$ to $R^5$ each represent a hydrogen atom, a cyano group, or a hydrocarbon group.]

28 Claims, 12 Drawing Sheets

AMINOSTYRYLANTHRACENE COMPOUND, SYNTHETIC INTERMEDIATE THEREOF, AND PROCESS FOR THE PRODUCTION THEREOF

This application is a 371 of PCT/JP01/03003 filed Apr. 6, 2001.

BACKGROUND OF THE INVENTION

The present invention relates to an aminostyrylanthracene compound suitable as an organic luminescent material emitting any desired color and a synthetic intermediate thereof, and a process for production thereof.

BACKGROUND ART

The organic electroluminescent element (EL element) is recently attracting attention as a candidate for the flat panel display which emits natural light, has a high response speed, and has no dependence on viewing angle. Thus, the organic luminescent material constituting EL elements is arousing acute interest. The first advantage of the organic luminescent material is that its optical properties can be controlled to a certain extent by molecular design. This makes it possible to realize a full-color organic luminescent element made of luminescent materials emitting three primary colors (red, blue, and green) individually.

Styryl compounds represented by the following general formula [A] find use as an organic electroluminescent material and also find use in various applications because they emit intense light (ranging from blue to red in the visible region) depending on the substituent introduced thereinto. In addition, being sublimable, they offer the advantage of forming a uniform amorphous film by vacuum deposition. The present-day molecular orbital calculations permit one to make an approximate prediction of the material's optical properties. In actual, a technology to produce the desired material efficiently is most important for industry.

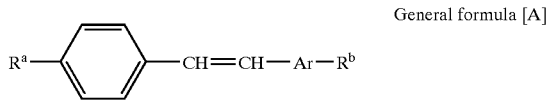

General formula [A]

(where, in the general formula [A] above, Ar represents an aryl group which may have a substituent, $R^a$ and $R^b$ each represent a hydrogen atom, a saturated or unsaturated hydrocarbon group, an aryl group which may have a substituent, a cyano group, a halogen atom, a nitro group, a hydrocarbon oxy group, or a hydrocarbon amino group, which may be identical or different.)

Organic luminescent materials produced so far are mostly those compounds represented by the general formula [A] above. Many of them emit light of blue to green, and only a few of them emit light of yellow to red. [The Institute of Electronics, Information and Communication Engineers; Technical Research Report; Organic Electronics, 17, 7 (1992), Inorganic and Organic Electroluminescence 96 Berlin, 101 (1996)] There has been no established method for their efficient production.

SUMMARY OF THE INVENTION

It is an object of the present invention, which was completed in view of the present state mentioned above, to provide a compound suitable for use as an organic luminescent material emitting intense yellow to red light, a synthetic intermediate thereof, and a process for its efficient production.

In order to address the above-mentioned problem, the present inventors carried out extensive studies. As the result, they found that an aminostyrylanthracene compound represented by the general formula [I], [II], [III], or [IV] emits intense light and hence is useful as a luminescent material for yellow to red light, and they also established a general, efficient process for its production.

First, the present invention relates to an aminostyrylanthracene compound represented by the following general formula [I], [II], [III], or [IV]. (referred to as "the compound of the present invention" hereinafter)

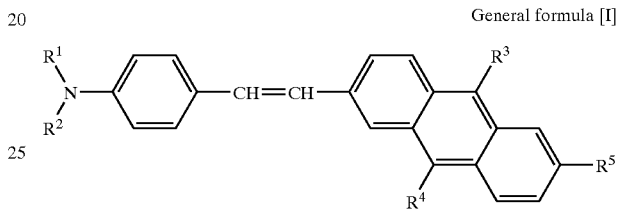

General formula [I]

[where, in the general formula [I] above, $R^2$ represents an unsubstituted aryl group, $R^1$ represents an aryl group represented by the following general formula (1),

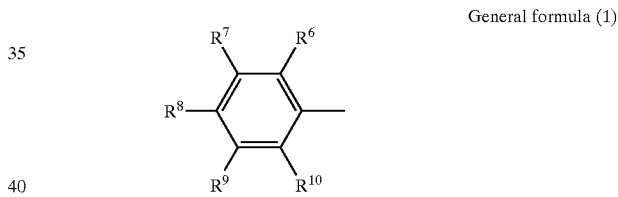

General formula (1)

(where, in the general formula (1) above, $R^6$, $R^7$, $R^8$, $R^9$, and $R^{10}$ are identical or different groups, each representing a hydrogen atom, a saturated or unsaturated hydrocarbon oxy group having one or more carbons, a hydrocarbon group, a hydrocarbon amino group, a fluoroalkyl group, or an aryl group which may have a substituent.) $R^3$ and $R^4$ are identical or different groups, at least one of them being a hydrogen atom, a cyano group, a fluoroalkyl group, a nitro group, or a halogen atom, and $R^5$ represents a hydrogen atom, a saturated or unsaturated hydrocarbon group having one or more carbons, or an aryl group which may have a substituent.]

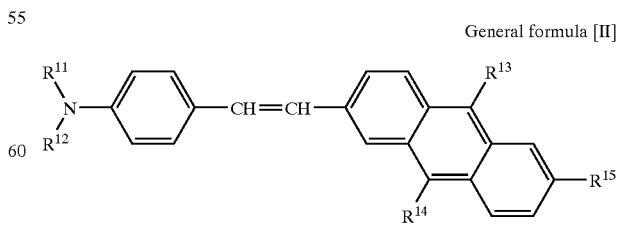

General formula [II]

[where, in the general formula [II] above, $R^{11}$ and $R^{12}$ are identical or different groups, each representing an aryl group represented by the following general formula (2), General formula (2)

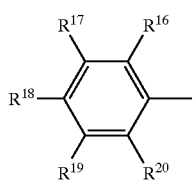

(where, in the general formula (2) above, $R^{16}$, $R^{17}$, $R^{18}$, $R^{19}$, and $R^{20}$ are identical or different groups, each representing a hydrogen atom, a saturated or unsaturated hydrocarbon oxy group having one or more carbons, a hydrocarbon group, a hydrocarbon amino group, a fluoroalkyl group, or an aryl group which may have a substituent.) $R^{13}$ and $R^{14}$ are identical or different groups, at least one of them being a hydrogen atom, a cyano group, a fluoroalkyl group, a nitro group, or a halogen atom, and $R^{15}$ represents a hydrogen atom, a saturated or unsaturated hydrocarbon group having one or more carbons, or an aryl group which may have a substituent.]

General formula [III]

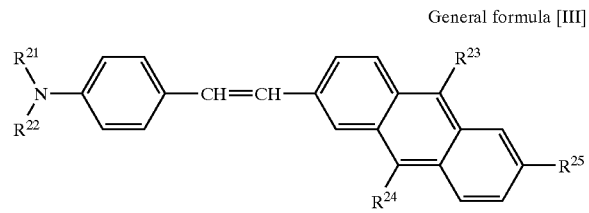

[where, in the general formula [III] above, $R^{21}$ represents an aryl group represented by the following general formula (3), General formula (3)

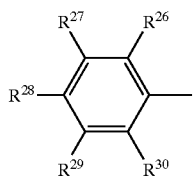

(where, in the general formula (3) above, $R^{26}$, $R^{27}$, $R^{28}$, $R^{29}$, and $R^{30}$ are identical or different groups, each representing a hydrogen atom, a saturated or unsaturated hydrocarbon oxy group having one or more carbons, a hydrocarbon group, a hydrocarbon amino group, or a fluoroalkyl group.) $R^{22}$ represents an aryl group represented by the following general formula (4), General formula (4)

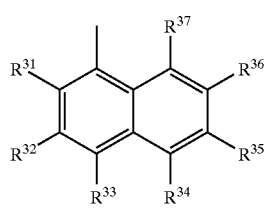

(where, in the general formula (4) above, $R^{31}$, $R^{32}$, $R^{33}$, $R^{34}$, $R^{35}$, $R^{36}$, and $R^{37}$ are identical or different groups, each representing a hydrogen atom, a saturated or unsaturated hydrocarbon oxy group having one or more carbons, a hydrocarbon group, a hydrocarbon amino group, a fluoroalkyl group, or an aryl group which may have a substituent.)

$R^{23}$ and $R^{24}$ are identical or different groups, at least one of them being a hydrogen atom, a cyano group, a fluoroalkyl group, a nitro group, or a halogen atom, and $R^{25}$ represents a hydrogen atom, a saturated or unsaturated hydrocarbon group having one or more carbons, or an aryl group which may have a substituent.]

General formula [IV]

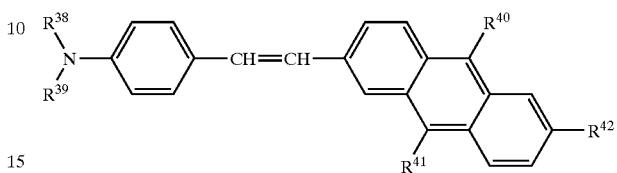

[where, in the general formula [IV] above, $R^{38}$ and $R^{39}$ are identical or different groups, at least one of them being a hydrogen atom or a saturated or unsaturated hydrocarbon group having one or more carbons, $R^{40}$ and $R^{41}$ are identical or different groups, each representing a hydrogen atom, a cyano group, a fluoroalkyl group, a nitro group, or a halogen atom, and $R^{42}$ represents a hydrogen atom, a saturated or unsaturated hydrocarbon group having one or more carbons, or an aryl group which may have a substituent.]

The compound of the present invention can be effectively used as an organic luminescent material which emits yellow to red light. It has a high glass transition point and a high melting point. It is stable electrically, thermally, and chemically and is amorphous. It easily takes on a glassy state and hence is capable of vapor deposition.

The compound of the present invention should preferably be one which is represented by any of the following general formulas.

General formula (5)

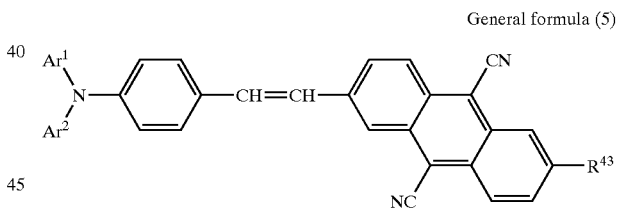

[where, in the general formula (5) above, $Ar^1$ and $Ar^2$ are identical or different aryl groups which may have a substituent and, if they have a substituent, they represent a group selected from aryl groups represented by the following general formulas (6), (7), (8), (9), (10), and (11).

General formula (6)

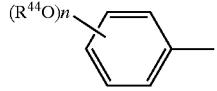

General formula (7)

General formula (8)

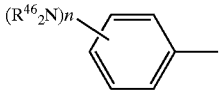

-continued

General formula (9)

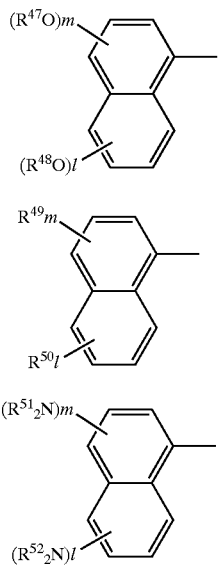

General formula (10)

General formula (11)

General formula (13)

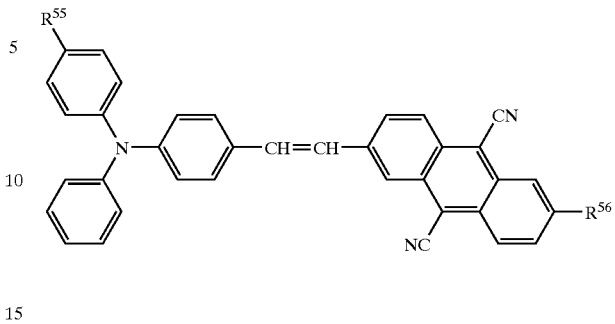

(where, in the general formula (13) above, $R^{55}$ represents a saturated or unsaturated hydrocarbon group having 1 to 6 carbons, a trifluoromethyl group, or an aryl group which may have a substituent, and $R^{56}$ represents a hydrogen atom, a saturated or unsaturated hydrocarbon group having 1 to 6 carbons, or an aryl group which may have a substituent.)

(where, in the general formulas (6), (7), (8), (9), (10), and (11) above, $R^{44}$, $R^{45}$, and $R^{46}$ each represent a saturated or unsaturated hydrocarbon group having one or more carbons (preferably 1 to 6) or a fluoroalkyl group, $R^{47}$, $R^{48}$, $R^{49}$, $R^{50}$, $R^{51}$, and $R^{52}$ are identical or different groups, each representing a saturated or unsaturated hydrocarbon group having one or more carbons (preferably 1 to 6 carbons), or a fluoroalkyl group, n is an integer of 0 to 5, m is an integer of 0 to 3, and 1 is an integer of 0 to 3), $R^{43}$ represents a hydrogen atom, a saturated or unsaturated hydrocarbon group having one or more carbons, or an aryl group which may have a substituent.]

To be more concrete, the compound of the present invention should preferably be one which is represented by the following general formula (12), (13), (14), (15), (16), (17), or (18).

General formula (14)

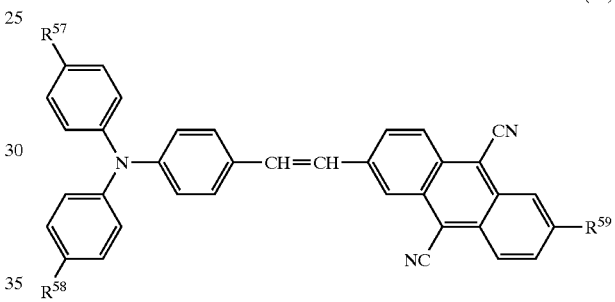

(where, in the general formula (14) above, $R^{57}$ and $R^{58}$ each represent a saturated or unsaturated hydrocarbon group having 1 to 6 carbons, a trifluoromethyl group, or an aryl group which may have a substituent, and $R^{59}$ represents a hydrogen atom, a saturated or unsaturated hydrocarbon group having 1 to 6 carbons, or an aryl group which may have a substituent.)

General formula (12)

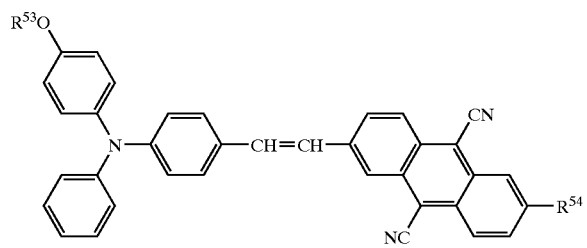

(where, in the general formula (12) above, $R^{53}$ represents a saturated or unsaturated hydrocarbon group having 1 to 6 carbons or an aryl group which may have a substituent, and $R^{54}$ represents a hydrogen atom, a saturated or unsaturated hydrocarbon group having 1 to 6 carbons, or an aryl group which may have a substituent.)

General formula (15)

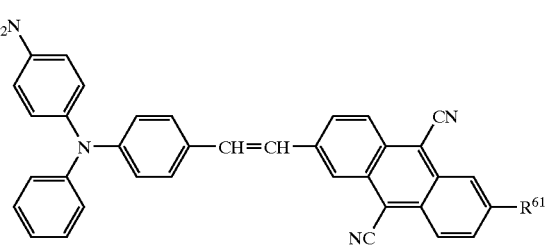

(where, in the general formula (15) above, $R^{60}$ represents a saturated or unsaturated hydrocarbon group having 1 to 6 carbons or an aryl group which may have a substituent, and $R^{61}$ represents a hydrogen atom, a saturated or unsaturated hydrocarbon group having 1 to 6 carbons, or an aryl group which may have a substituent.)

General formula (16)

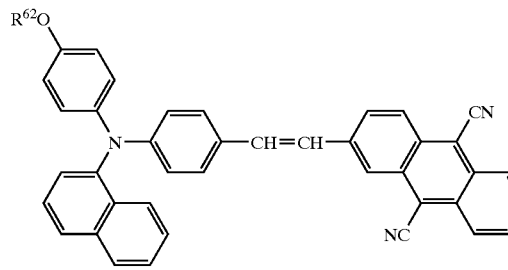

(where, in the general formula (16) above, $R^{62}$ represents a saturated or unsaturated hydrocarbon group having 1 to 6 carbons or an aryl group which may have a substituent, and $R^{63}$ represents a hydrogen atom, a saturated or unsaturated hydrocarbon group having 1 to 6 carbons, or an aryl group which may have a substituent.)

General formula (17)

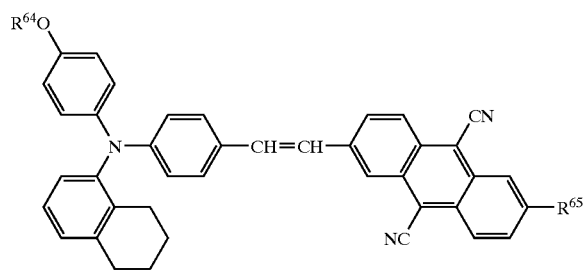

(where, in the general formula (17) above, $R^{64}$ represents a saturated or unsaturated hydrocarbon group having 1 to 6 carbons or an aryl group which may have a substituent, and $R^{65}$ represents a hydrogen atom, a saturated or unsaturated hydrocarbon group having 1 to 6 carbons, or an aryl group which may have a substituent.)

General formula (18)

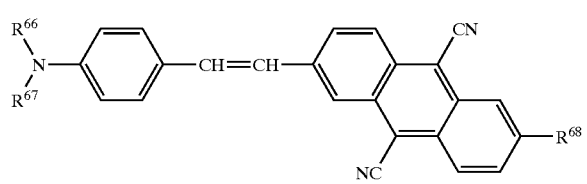

(where, in the general formula (18) above, $R^{66}$ and $R^{67}$ each represent a saturated or unsaturated hydrocarbon group having 1 to 6 carbons or an aryl group which may have a substituent, and $R^{68}$ represents a hydrogen atom, a saturated or unsaturated hydrocarbon group having 1 to 6 carbons, or an aryl group which may have a substituent.)

The compound of the present invention is exemplified by the one which is represented by the following structural formula (19)-1, (19)-2, (19)-3, (19)-4, (19)-5, (19)-6, (19)-7, (19)-8, (19)-9, (19)-10, (19)-11, or (19)-12.

Structural formula (19)-1

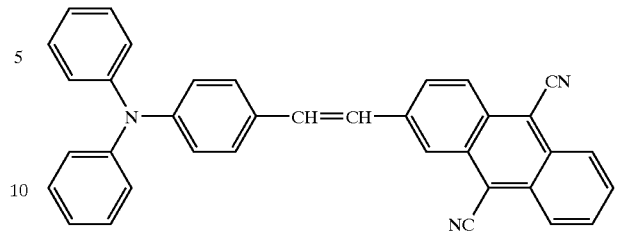

Structural formula (19)-2

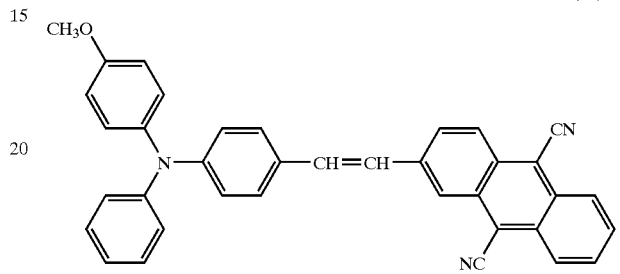

Structural formula (19)-3

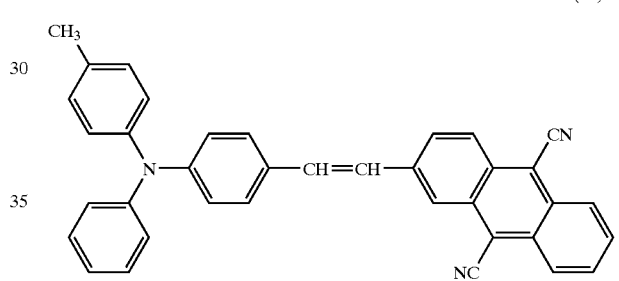

Structural formula (19)-4

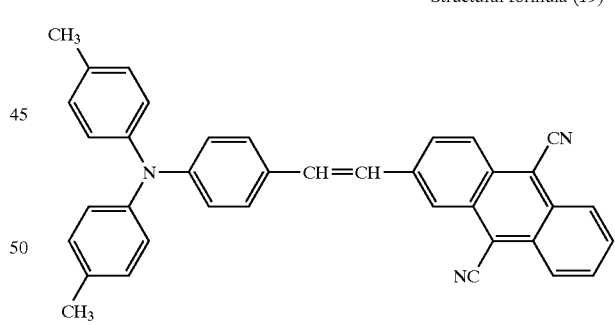

Structural formula (19)-5

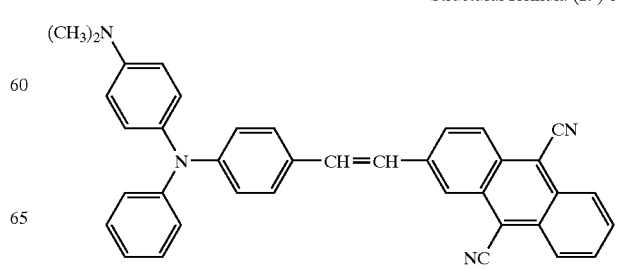

Structural formula (19)-6

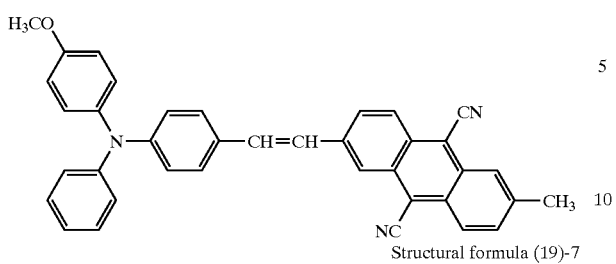

Structural formula (19)-7

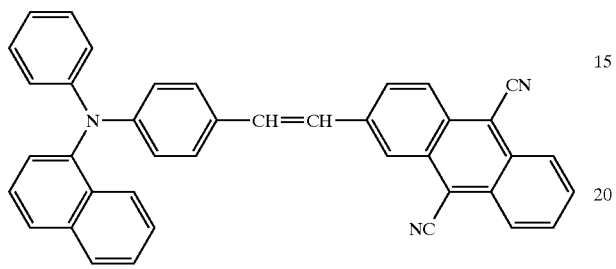

Structural formula (19)-8

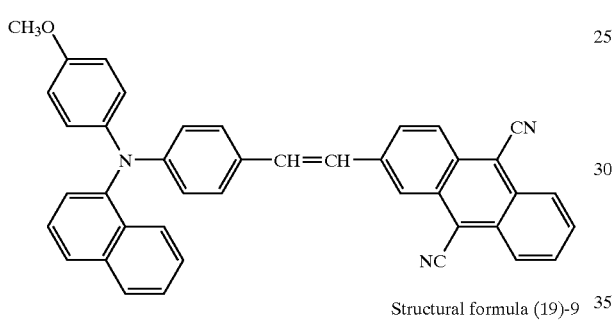

Structural formula (19)-9

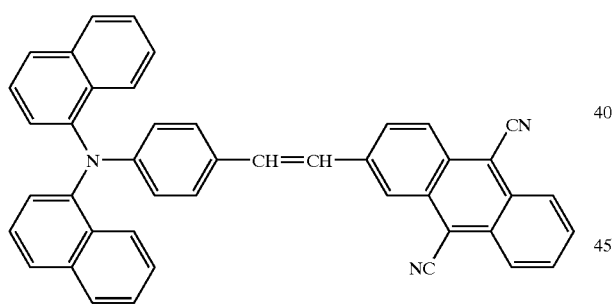

Structural formula (19)-10

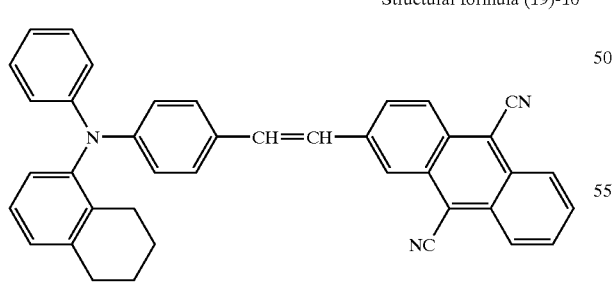

Structural formula (19)-11

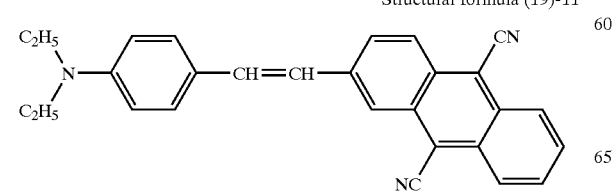

Structural formula (19)-12

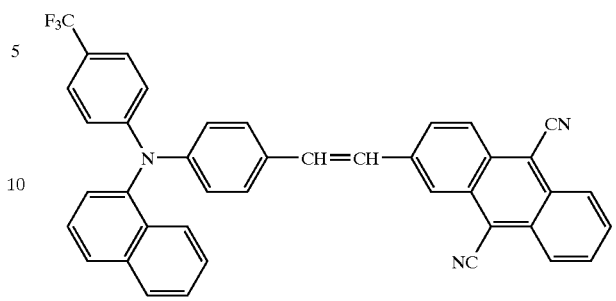

The compound of the present invention should preferably be one which is represented by the following general formula.

General formula (20)

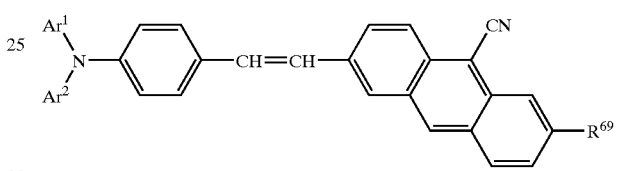

(where, in the general formula (20) above, $Ar^1$ and $Ar^2$ are identical or different aryl groups which may have a substituent and, if they have a substituent, they represent a group selected from aryl groups represented by the following general formulas (6), (7), (8), (9), (10), and (11).

General formula (6)

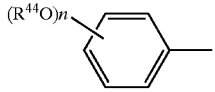

General formula (7)

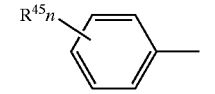

General formula (8)

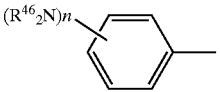

General formula (9)

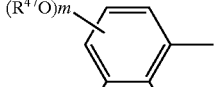

General formula (10)

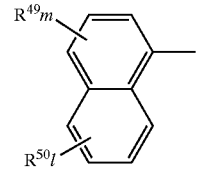

-continued

General formula (11)

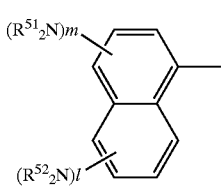

(where, in the general formulas (6), (7), (8), (9), (10), and (11) above, $R^{44}$, $R^{45}$, $R^{45}$, and $R^{46}$ each represent a saturated or unsaturated hydrocarbon group having one or more carbons (preferably 1 to 6 carbons) or a fluoroalkyl group, $R^{47}$, $R^{48}$, $R^{49}$, $R^{50}$, $R^{51}$, and $R^{52}$ are identical or different groups, each representing a saturated or unsaturated hydrocarbon group having one or more carbons (preferably 1 to 6 carbons), or a fluoroalkyl group, n is an integer of 0 to 5, m is an integer of 0 to 3, and l is an integer of 0 to 3), and $R^{69}$ represents a hydrogen atom, a saturated or unsaturated hydrocarbon group or an aryl group which may have a substituent.]

To be more concrete, the compound of the present invention should preferably be one which is represented by the following general formula (21), (22), (23), (24), (25), (26), or (27).

General formula (21)

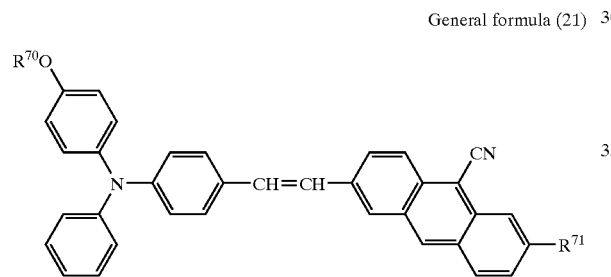

(where, in the general formula (21) above, $R^{70}$ represents a saturated or unsaturated hydrocarbon group having 1 to 6 carbons or an aryl group which may have a substituent, and $R^{71}$ represents a hydrogen atom, a saturated or unsaturated hydrocarbon group having 1 to 6 carbons, or an aryl group which may have a substituent.)

General formula (22)

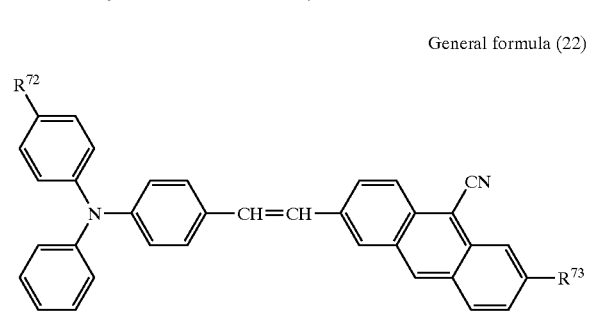

(where, in the general formula (22) above, $R^{72}$ represents a saturated or unsaturated hydrocarbon group having 1 to 6 carbons, a trifluoromethyl group, or an aryl group which may have a substituent, and $R^{73}$ represents a hydrogen atom, a saturated or unsaturated hydrocarbon group having 1 to 6 carbons, or an aryl group which may have a substituent.)

General formula (23)

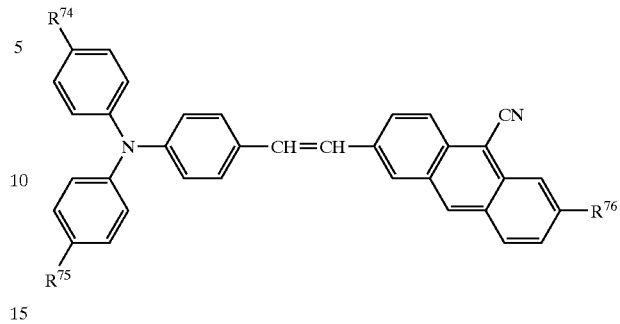

(where, in the general formula (23) above, $R^{74}$ and $R^{75}$ each represent a saturated or unsaturated hydrocarbon group having 1 to 6 carbons, a trifluoromethyl group, or an aryl group which may have a substituent, and $R^{76}$ represents a hydrogen atom, a saturated or unsaturated hydrocarbon group having 1 to 6 carbons, or an aryl group which may have a substituent.)

General formula (24)

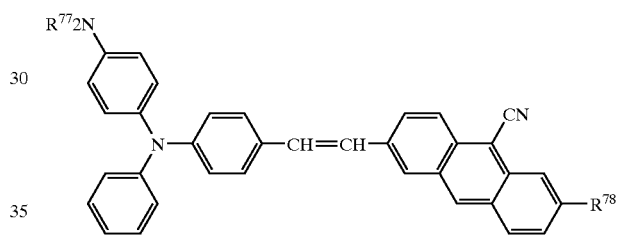

(where, in the general formula (24) above, $R^{77}$ represents a saturated or unsaturated hydrocarbon group having 1 to 6 carbons or an aryl group which may have a substituent, and $R^{78}$ represents a hydrogen atom, a saturated or unsaturated hydrocarbon group having 1 to 6 carbons, or an aryl group which may have a substituent.)

General formula (25)

(where, in the general formula (25) above, $R^{79}$ represents a saturated or unsaturated hydrocarbon group having 1 to 6 carbons or an aryl group which may have a substituent, and $R^{80}$ represents a hydrogen atom, a saturated or unsaturated hydrocarbon group having 1 to 6 carbons, or an aryl group which may have a substituent.)

General formula (26)

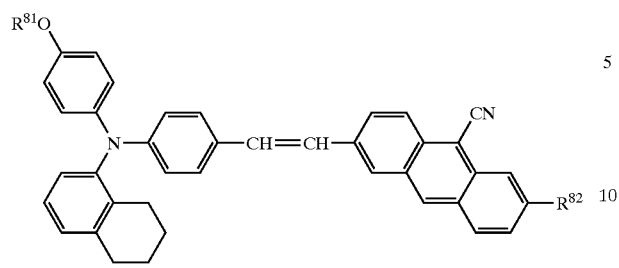

(where, in the general formula (26) above, $R^{81}$ represents a saturated or unsaturated hydrocarbon group having 1 to 6 carbons or an aryl group which may have a substituent, and $R^{82}$ represents a hydrogen atom, a saturated or unsaturated hydrocarbon group having 1 to 6 carbons, or an aryl group which may have a substituent.)

General formula (27)

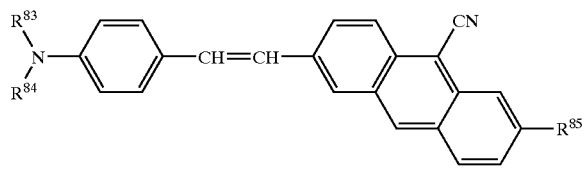

(where, in the general formula (27) above, $R^{82}$ and $R^{83}$ each represent a saturated or unsaturated hydrocarbon group having 1 to 6 carbons or an aryl group which may have a substituent, and $R^{85}$ represents a hydrogen atom, a saturated or unsaturated hydrocarbon group having 1 to 6 carbons, or an aryl group which may have a substituent.)

The compound of the present invention is exemplified by the one which is represented by the following structural formula (28)-1, (28)-2, (28)-3, (28)-4, (28)-5, (28)-6, (28)-7, (28)-8, (28)-9, (28)-10, (28)-11, or (28)-12.

Structural formula (28)-1

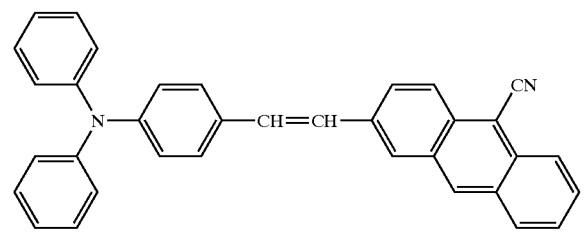

Structural formula (28)-2

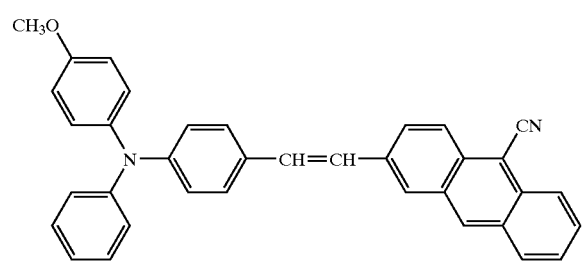

Structural formula (28)-3

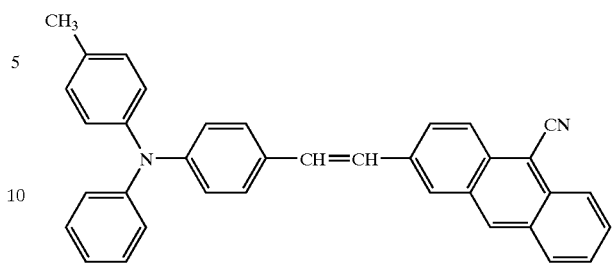

Structural formula (28)-4

Structural formula (28)-5

Structural formula (28)-6

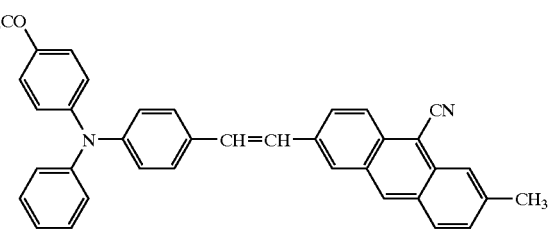

Structural formula (28)-7

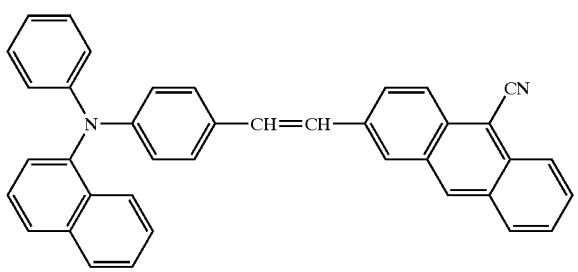

-continued

Structural formula (28)-8

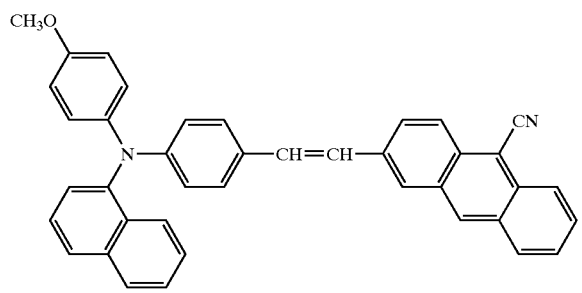

Structural formula (28)-9

Structural formula (28)-10

Structural formula (28)-11

Structural formula (28)-12

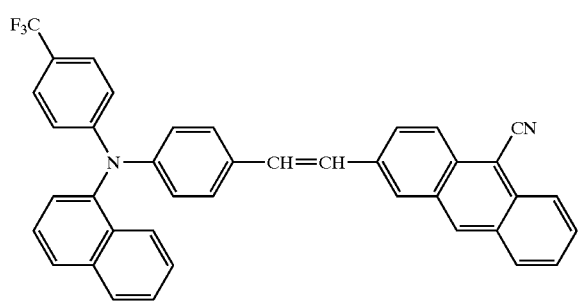

The compound of the present invention should preferably be one which is represented by the following general formula.

General formula (29)

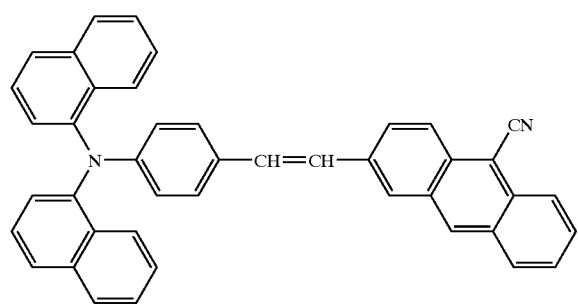

(where, in the general formula (29) above, $Ar^1$ and $Ar^2$ are identical or different aryl groups which may have a substituent and, if they have a substituent, they represent a group selected from aryl groups represented by the following general formulas (6), (7), (8), (9), (10), and (11).

General formula (6)

General formula (7)

General formula (8)

General formula (9)

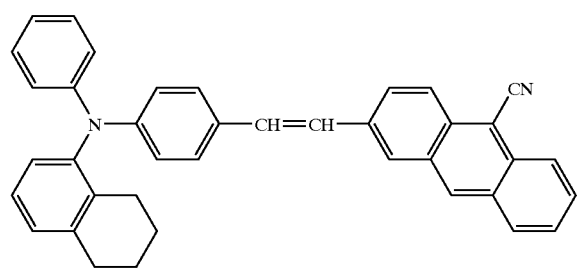

General formula (10)

General formula (11)

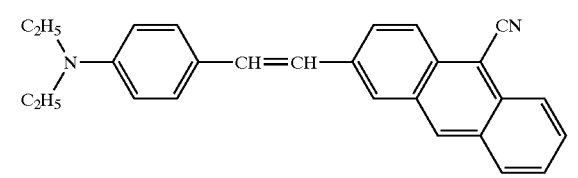

(where, in the general formulas (6), (7), (8), (9), (10), and (11) above, $R^{44}$, $R^{45}$, and $R^{46}$ each represent a saturated or unsaturated hydrocarbon group having one or more carbons (preferably 1 to 6 carbons) or a fluoroalkyl group, $R^{47}$, $R^{48}$, $R^{49}$, $R^{50}$, $R^{51}$, and $R^{52}$ are identical or different groups, each representing a saturated or unsaturated hydrocarbon group having one or more carbons (preferably 1 to 6 carbons), or a fluoroalkyl group, n is an integer of 0 to 5, m is an integer of 0 to 3, and l is an integer of 0 to 3), $R^{86}$ represents a hydrogen atom, a saturated or unsaturated hydrocarbon group having one or more carbons, or an aryl group which may have a substituent.)

To be more concrete, the compound of the present invention should preferably be one which is represented by the following formula (30), (31), (32), (33), (34), (35), or (36).

General formula (30)

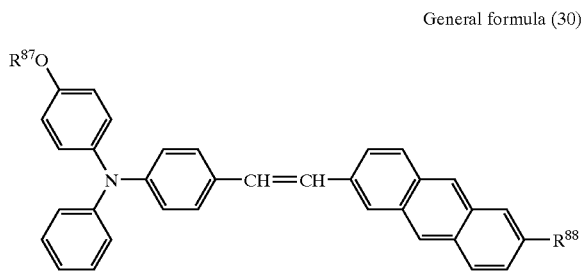

(where, in the general formula (30) above, $R^{87}$ represents a saturated or unsaturated hydrocarbon group having 1 to 6 carbons or an aryl group which may have a substituent, and $R^{88}$ represents a hydrogen atom, a saturated or unsaturated hydrocarbon group having 1 to 6 carbons, or an aryl group which may have a substituent.)

General formula (31)

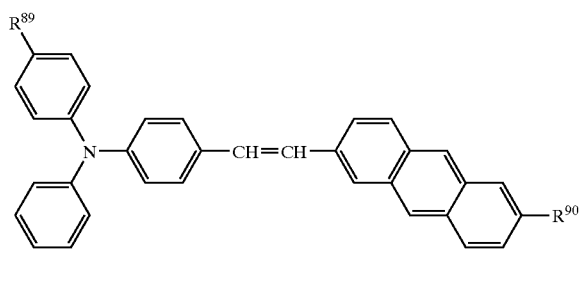

(where, in the general formula (31) above, $R^{89}$ represents a saturated or unsaturated hydrocarbon group having 1 to 6 carbons, a trifluoromethyl group, or an aryl group which may have a substituent, and $R^{90}$ represents a hydrogen atom, a saturated or unsaturated hydrocarbon group having 1 to 6 carbons, or an aryl group which may have a substituent.)

General formula (32)

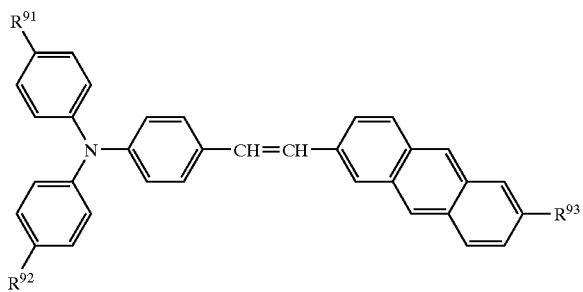

(where, in the general formula (32) above, $R^{91}$ and $R^{92}$ each represent a saturated or unsaturated hydrocarbon group having 1 to 6 carbons, a trifluoromethyl group, or an aryl group which may have a substituent, and $R^{93}$ represents a hydrogen atom, a saturated or unsaturated hydrocarbon group having 1 to 6 carbons, or an aryl group which may have a substituent.)

General formula (33)

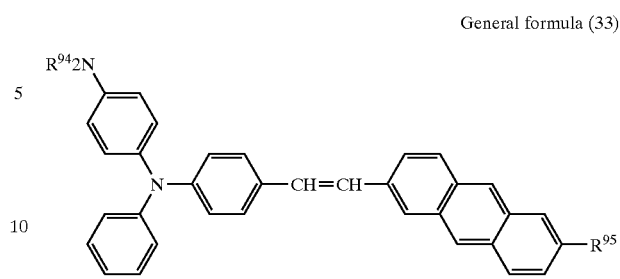

(where, in the general formula (33) above, $R^{94}$ represents a saturated or unsaturated hydrocarbon group having 1 to 6 carbons or an aryl group which may have a substituent, and $R^{95}$ represents a hydrogen atom, a saturated or unsaturated hydrocarbon group having 1 to 6 carbons, or an aryl group which may have a substituent.)

General formula (34)

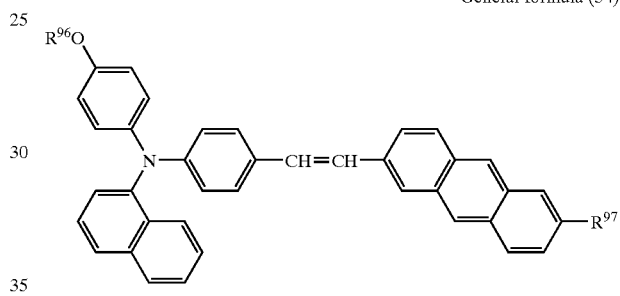

(where, in the general formula (34) above, $R^{96}$ represents a saturated or unsaturated hydrocarbon group having 1 to 6 carbons or an aryl group which may have a substituent, and $R^{97}$ represents a hydrogen atom, a saturated or unsaturated hydrocarbon group having 1 to 6 carbons, or an aryl group which may have a substituent.)

General formula (35)

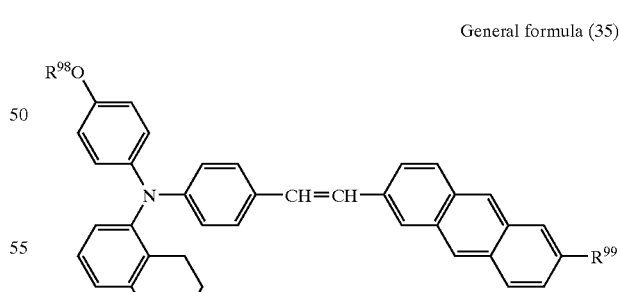

(where, in the general formula (35) above, $R^{98}$ represents a saturated or unsaturated hydrocarbon group having 1 to 6 carbons or an aryl group which may have a substituent, and $R^{99}$ represents a hydrogen atom, a saturated or unsaturated hydrocarbon group having 1 to 6 carbons, or an aryl group which may have a substituent.)

General formula (36)

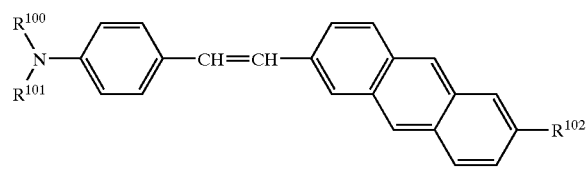

(where, in the general formula (36) above, $R^{100}$ and $R^{101}$ each represent a saturated or unsaturated hydrocarbon group having 1 to 6 carbons or an aryl group which may have a substituent, and $R^{102}$ represents a hydrogen atom, a saturated or unsaturated hydrocarbon group having 1 to 6 carbons, or an aryl group which may have a substituent.)

To be concrete, the compound of the present invention is exemplified by the one which is represented by the following structural formula (37)-1, (37)-2, (37)-3, (37)-4, (37)-5, (37)-6, (37)-7, (37)-8, (37)-9, (37)-10, (37)-11, or (37)-12.

Structural formula (37)-1

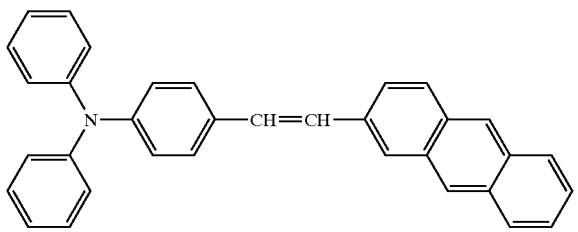

Structural formula (37)-2

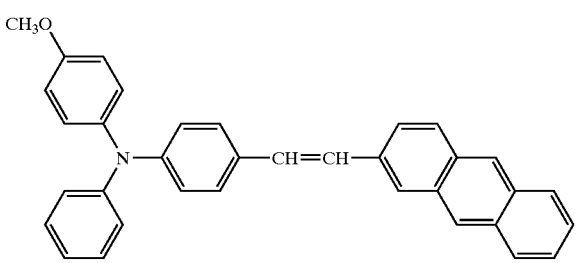

Structural formula (37)-3

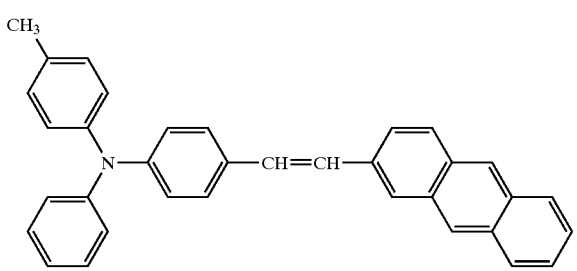

Structural formula (37)-4

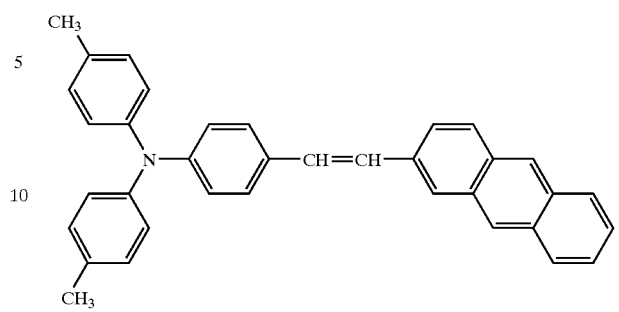

Structural formula (37)-5

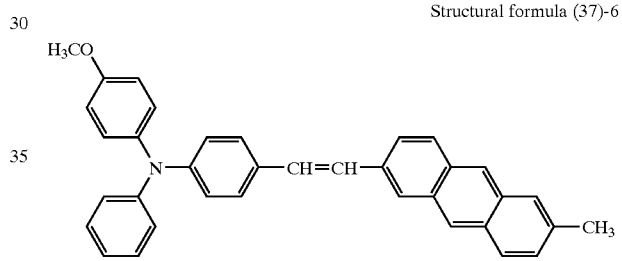

Structural formula (37)-6

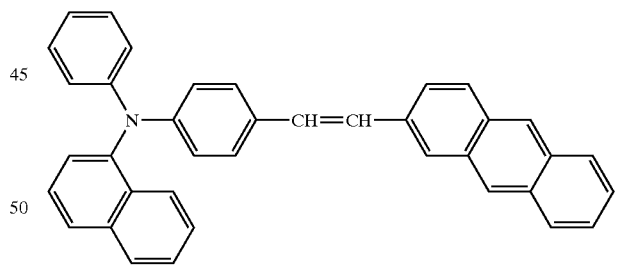

Structural formula (37)-7

Structural formula (37)-8

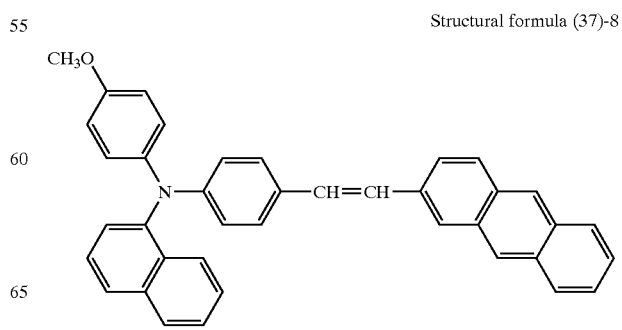

-continued

Structural formula (37)-9

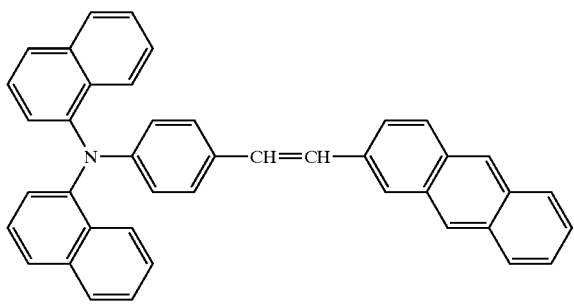

Structural formula (37)-10

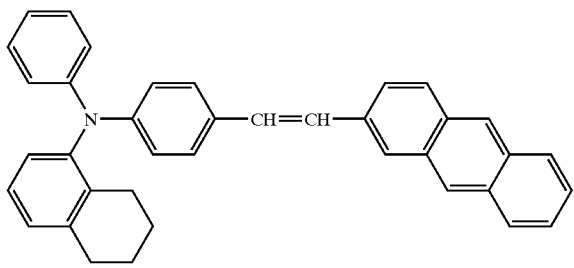

Structural formula (37)-11

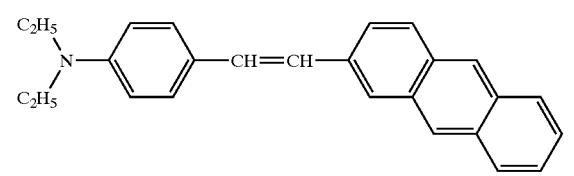

Structural formula (37)-12

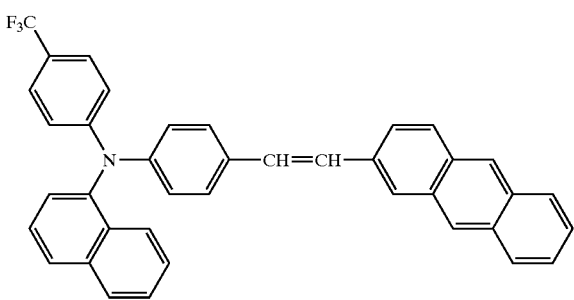

The compound of the present invention may be exemplified by the following compounds in addition to those mentioned above. (There are some duplicates.)

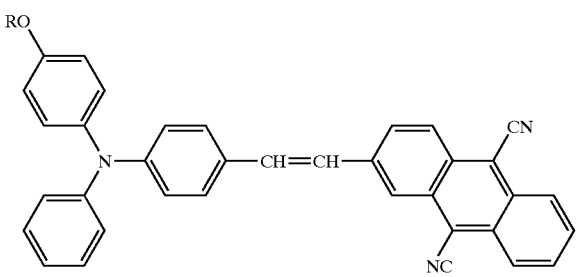

R = $C_2H_5$i-$C_3H_7$i-$C_5H_9$, t-$C_4H_9$,
cyclo-$C_6H_{10}C_6H_5$

-continued

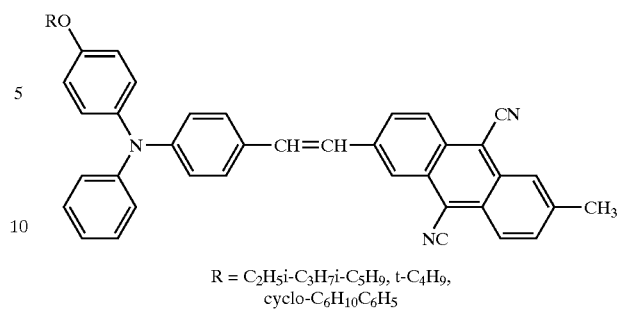

R = $C_2H_5$i-$C_3H_7$i-$C_5H_9$, t-$C_4H_9$,
cyclo-$C_6H_{10}C_6H_5$

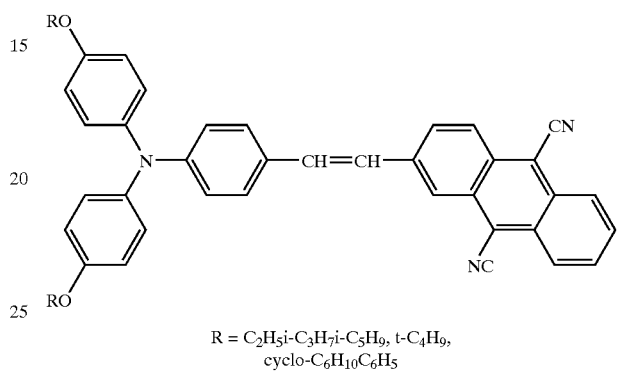

R = $C_2H_5$i-$C_3H_7$i-$C_5H_9$, t-$C_4H_9$,
cyclo-$C_6H_{10}C_6H_5$

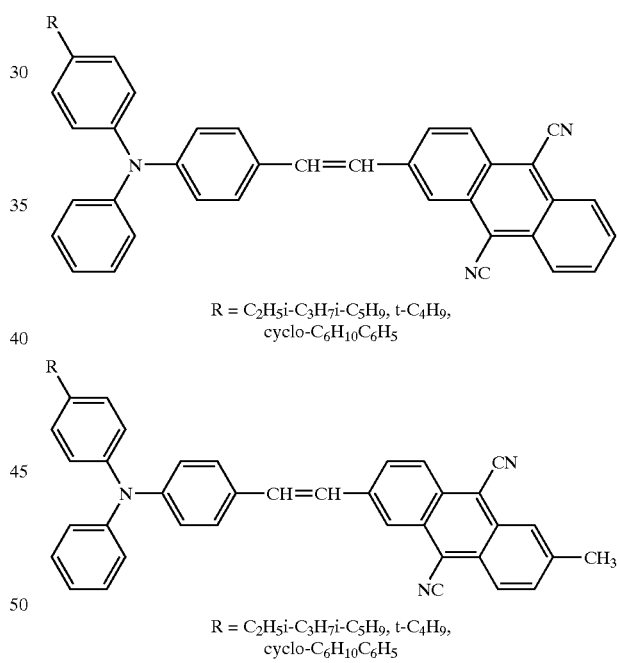

R = $C_2H_5$i-$C_3H_7$i-$C_5H_9$, t-$C_4H_9$,
cyclo-$C_6H_{10}C_6H_5$

R = $C_2H_5$i-$C_3H_7$i-$C_5H_9$, t-$C_4H_9$,
cyclo-$C_6H_{10}C_6H_5$

R = $C_2H_5$i-$C_3H_7$i-$C_5H_9$, t-$C_4H_9$,
cyclo-$C_6H_{10}C_6H_5$

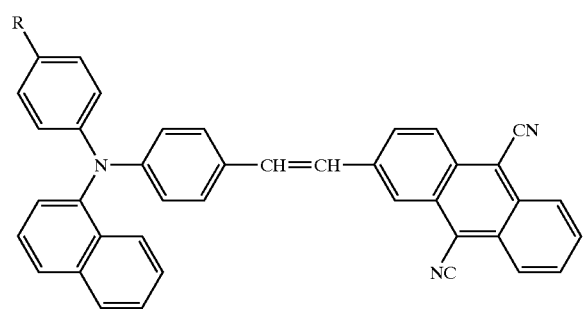
R = C₂H₅i-C₃H₇i-C₅H₉, t-C₄H₉,
cyclo-C₆H₁₀C₆H₅
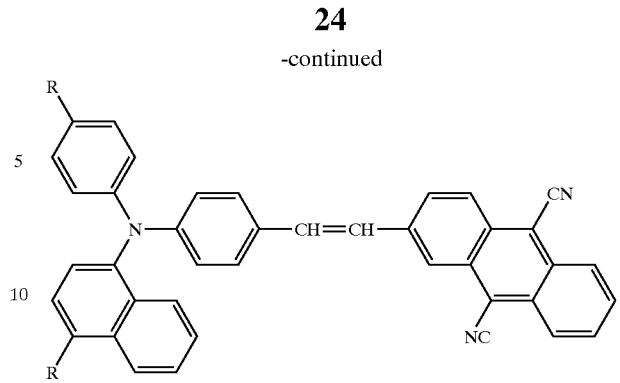
R = C₂H₅, i-C₃H₇, i-C₅H₉, t-C₄H₉,
cyclo-C₆H₁₀C₆H₅
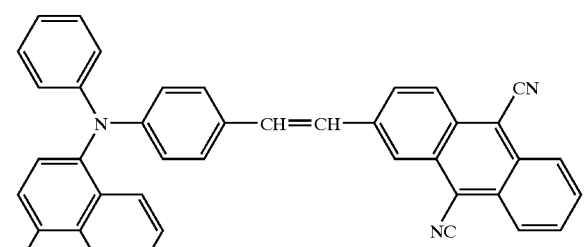
R = C₂H₅i-C₃H₇i-C₅H₉, t-C₄H₉,
cyclo-C₆H₁₀C₆H₅
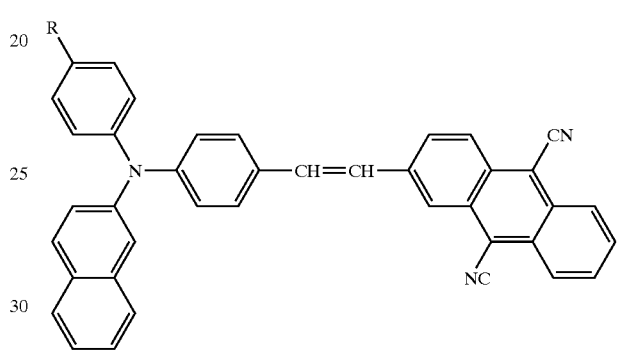
R = C₂H₅, i-C₃H₇, i-C₅H₉, t-C₄H₉,
cyclo-C₆H₁₀C₆H₅
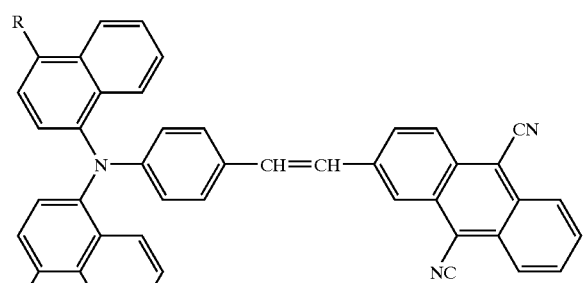
R = C₂H₅i-C₃H₇i-C₅H₉, t-C₄H₉,
cyclo-C₆H₁₀C₆H₅
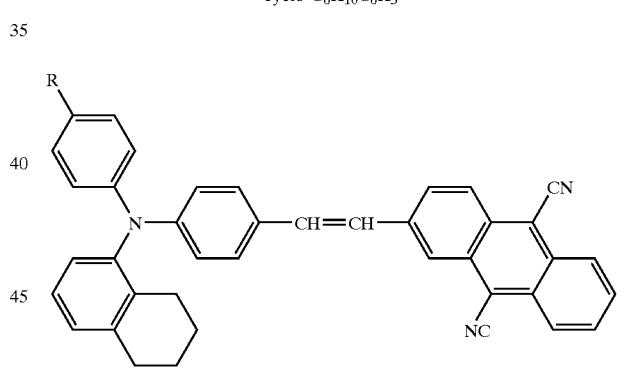
R = C₂H₅, i-C₃H₇, i-C₅H₉, t-C₄H₉,
cyclo-C₆H₁₀C₆H₅
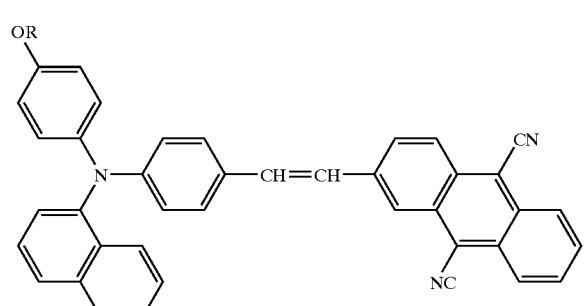
R = C₂H₅, i-C₃H₇, i-C₅H₉, t-C₄H₉,
cyclo-C₆H₁₀C₆H₅
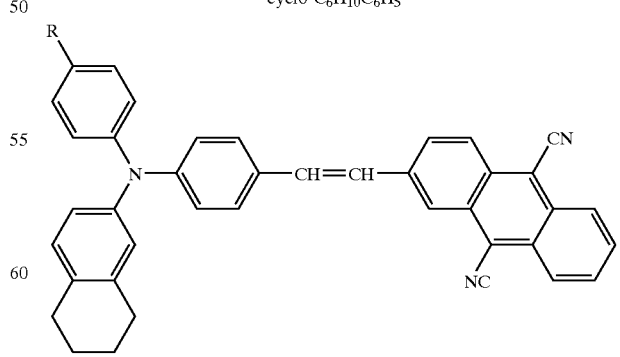
R = C₂H₅, i-C₃H₇, i-C₅H₉, t-C₄H₉,
cyclo-C₆H₁₀C₆H₅

-continued
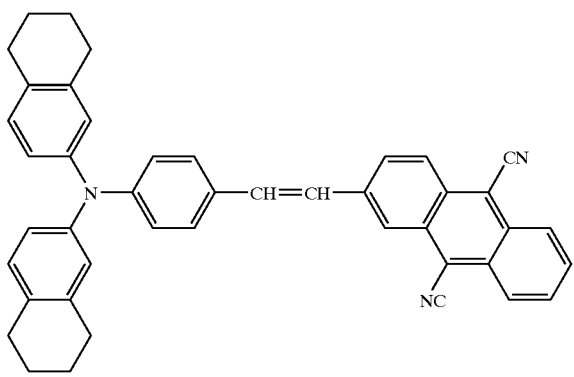
R = C₂H₅, i-C₃H₇, i-C₅H₉, t-C₄H₉, cyclo-C₆H₁₀C₆H₅
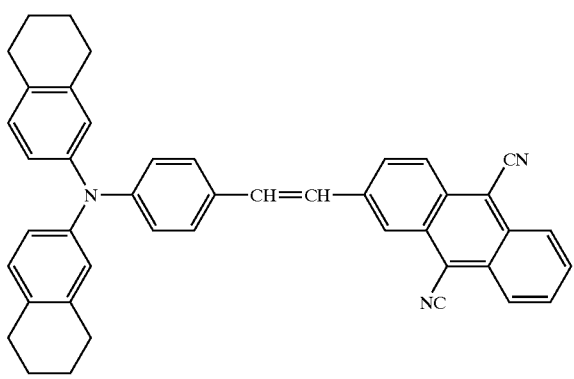
R = C₂H₅, i-C₃H₇, i-C₅H₉, t-C₄H₉, cyclo-C₆H₁₀C₆H₅
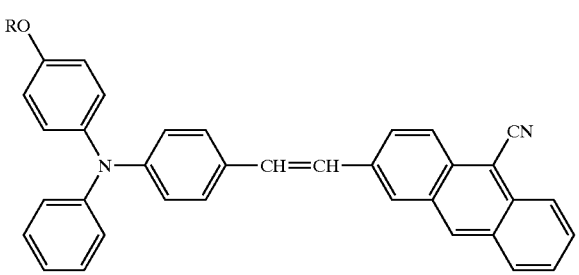
R = C₂H₅, i-C₃H₇, i-C₅H₉, t-C₄H₉, cyclo-C₆H₁₀C₆H₅
-continued
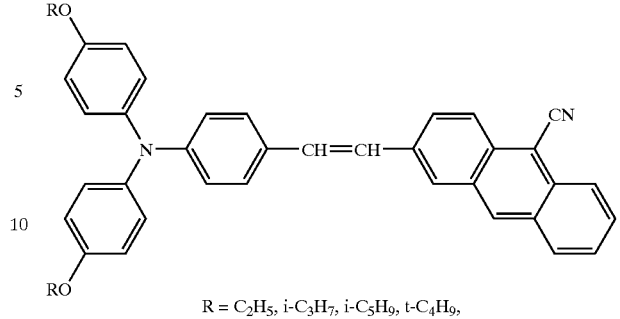
R = C₂H₅, i-C₃H₇, i-C₅H₉, t-C₄H₉, cyclo-C₆H₁₀C₆H₅
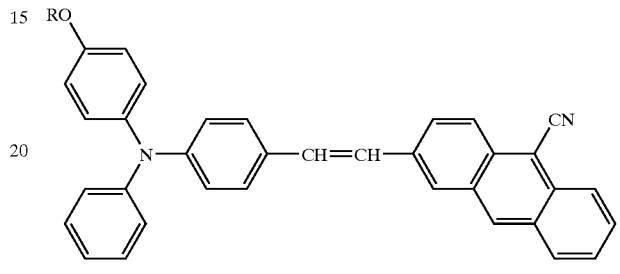
R = C₂H₅, i-C₃H₇, i-C₅H₉, t-C₄H₉, cyclo-C₆H₁₀C₆H₅
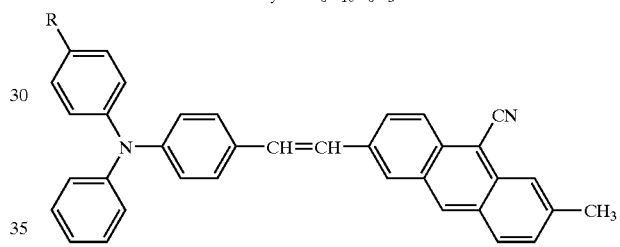
R = C₂H₅, i-C₃H₇, i-C₅H₉, t-C₄H₉, cyclo-C₆H₁₀C₆H₅
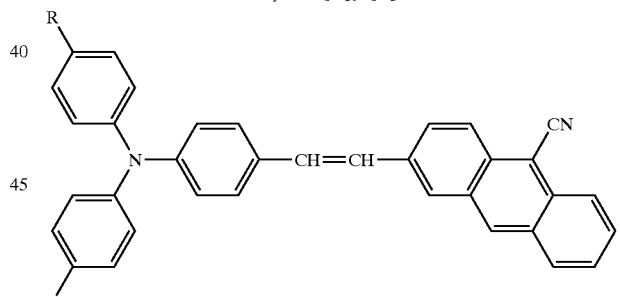
R = C₂H₅, i-C₃H₇, i-C₅H₉, t-C₄H₉, cyclo-C₆H₁₀C₆H₅
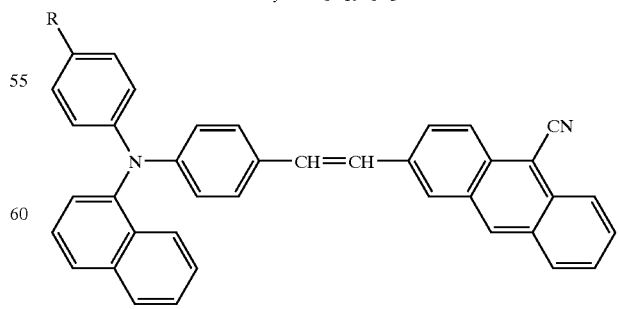
R = C₂H₅, i-C₃H₇, i-C₅H₉, t-C₄H₉, cyclo-C₆H₁₀C₆H₅

-continued
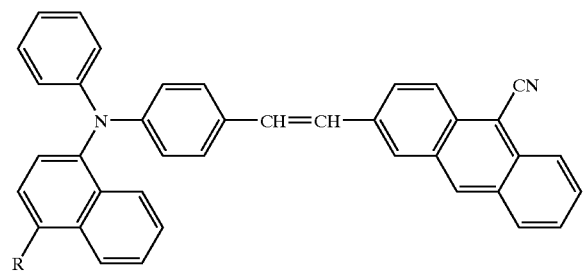
R = C₂H₅, i-C₃H₇, i-C₅H₉, t-C₄H₉,
cyclo-C₆H₁₀C₆H₅
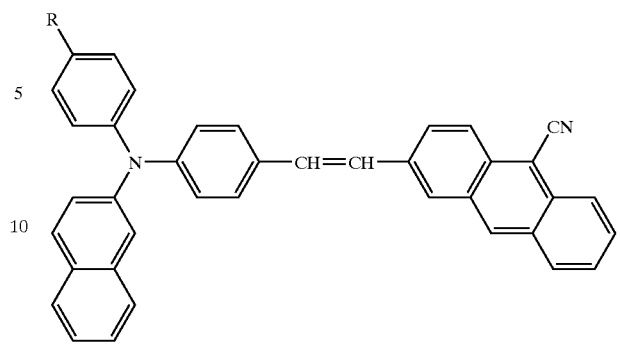
R = C₂H₅, i-C₃H₇, i-C₅H₉, t-C₄H₉,
cyclo-C₆H₁₀C₆H₅
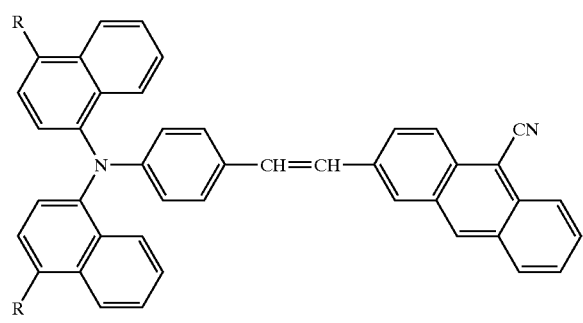
R = C₂H₅, i-C₃H₇, i-C₅H₉, t-C₄H₉
cyclo-C₆H₁₀C₆H₅
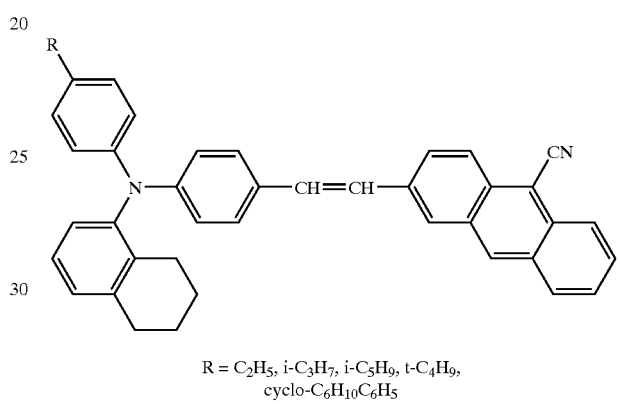
R = C₂H₅, i-C₃H₇, i-C₅H₉, t-C₄H₉,
cyclo-C₆H₁₀C₆H₅
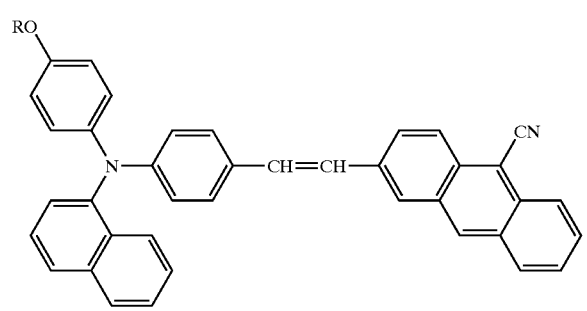
R = C₂H₅, i-C₃H₇, i-C₅H₉, t-C₄H₉,
cyclo-C₆H₁₀C₆H₅
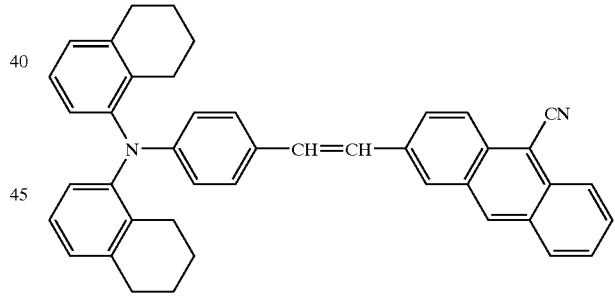
R = C₂H₅, i-C₃H₇, i-C₅H₉, t-C₄H₉,
cyclo-C₆H₁₀C₆H₅
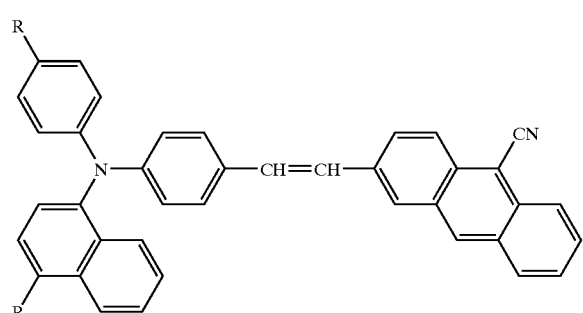
R = C₂H₅, i-C₃H₇, i-C₅H₉, t-C₄H₉,
cyclo-C₆H₁₀C₆H₅
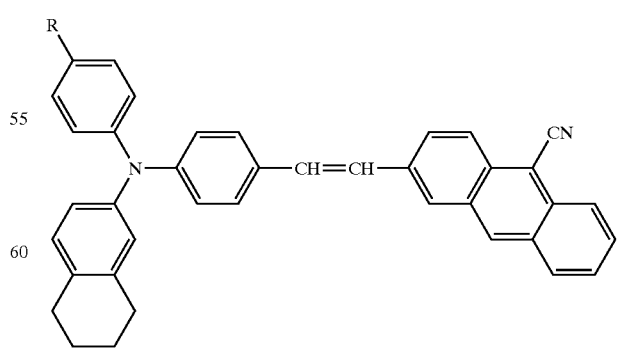
R = C₂H₅, i-C₃H₇, i-C₅H₉, t-C₄H₉,
cyclo-C₆H₁₀C₆H₅

-continued

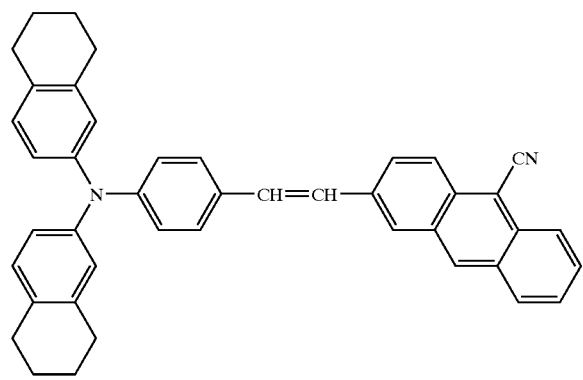

R = C₂H₅, i-C₃H₇, i-C₅H₉, t-C₄H₉,
cyclo-C₆H₁₀C₆H₅

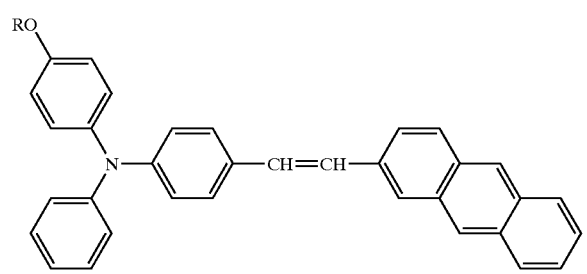

R = C₂H₅, i-C₃H₇, i-C₅H₉, t-C₄H₉,
cyclo-C₆H₁₀C₆H₅

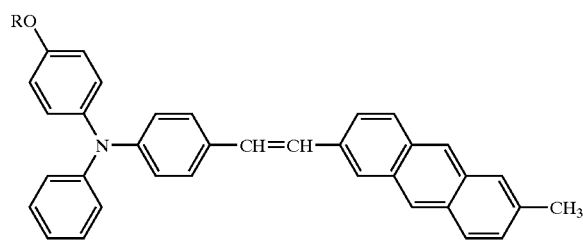

R = C₂H₅, i-C₃H₇, i-C₅H₉, t-C₄H₉,
cyclo-C₆H₁₀C₆H₅

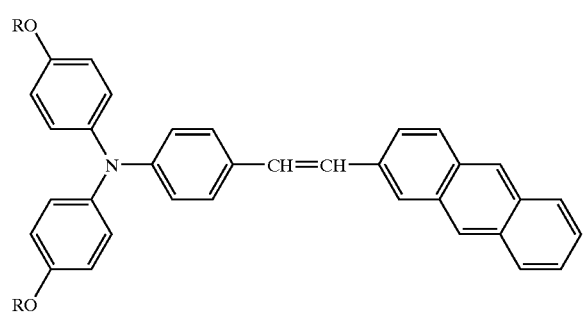

R = C₂H₅, i-C₃H₇, i-C₅H₉, t-C₄H₉,
cyclo-C₆H₁₀C₆H₅

-continued

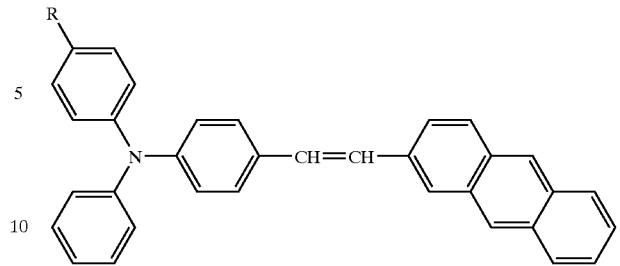

R = C₂H₅, i-C₃H₇, i-C₅H₉, t-C₄H₉,
cyclo-C₆H₁₀C₆H₅

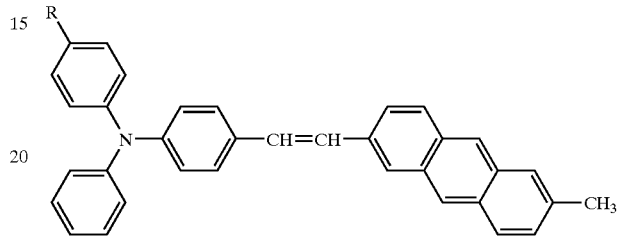

R = C₂H₅, i-C₃H₇, i-C₅H₉, t-C₄H₉,
cyclo-C₆H₁₀C₆H₅

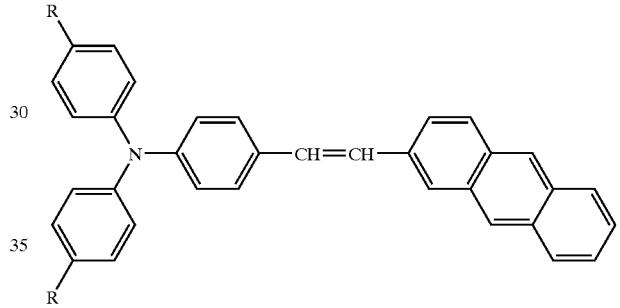

R = C₂H₅, i-C₃H₇, i-C₅H₉, t-C₄H₉,
cyclo-C₆H₁₀C₆H₅

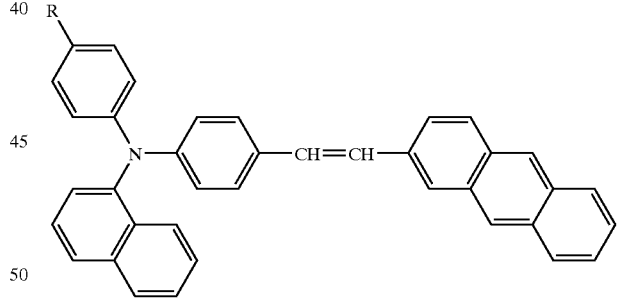

R = C₂H₅, i-C₃H₇, i-C₅H₉, t-C₄H₉,
cyclo-C₆H₁₀C₆H₅

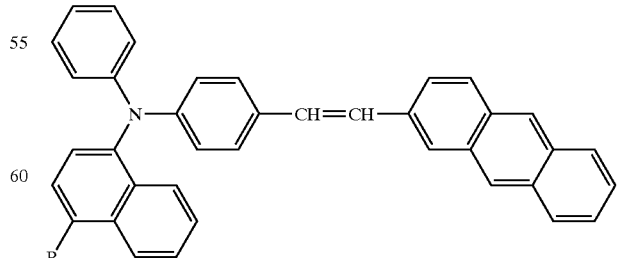

R = C₂H₅, i-C₃H₇, i-C₅H₉, t-C₄H₉,
cyclo-C₆H₁₀C₆H₅

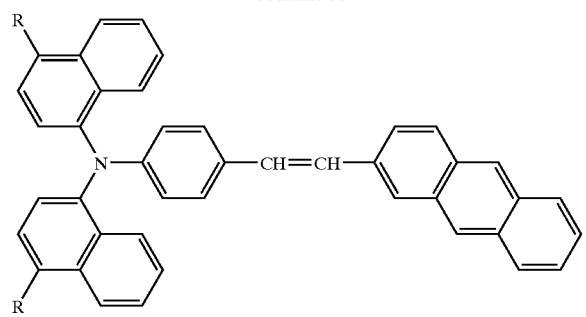
R = C₂H₅, i-C₃H₇, i-C₅H₉, t-C₄H₉,
cyclo-C₆H₁₀C₆H₅
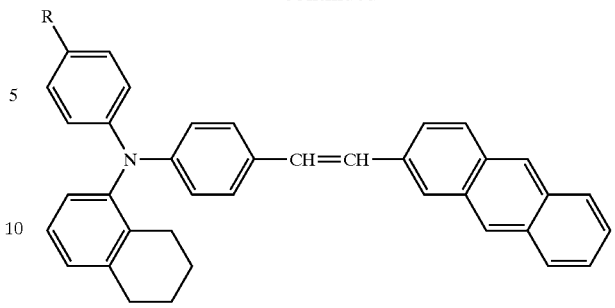
R = C₂H₅, i-C₃H₇, i-C₅H₉, t-C₄H₉,
cyclo-C₆H₁₀C₆H₅
R = C₂H₅, i-C₃H₇, i-C₅H₉, t-C₄H₉,
cyclo-C₆H₁₀C₆H₅
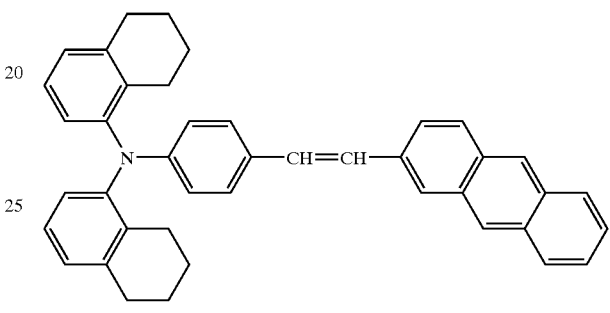
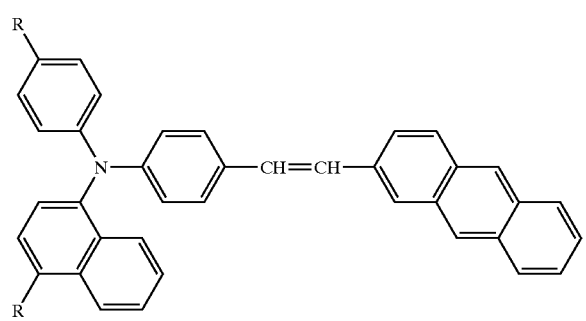
R = C₂H₅, i-C₃H₇, i-C₅H₉, t-C₄H₉,
cyclo-C₆H₁₀C₆H₅
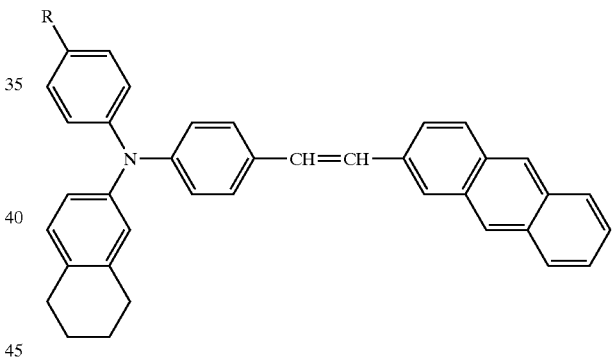
R = C₂H₅, i-C₃H₇, i-C₅H₉, t-C₄H₉,
cyclo-C₆H₁₀C₆H₅
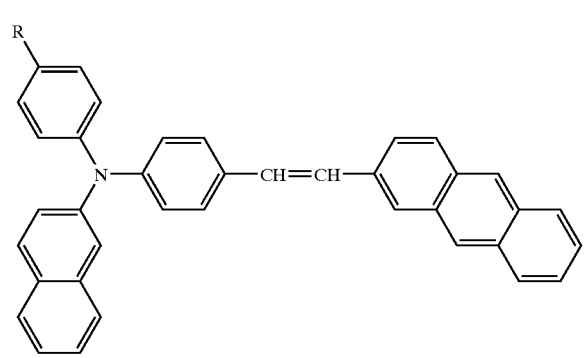
R = C₂H₅, i-C₃H₇, i-C₅H₉, t-C₄H₉,
cyclo-C₆H₁₀C₆H₅
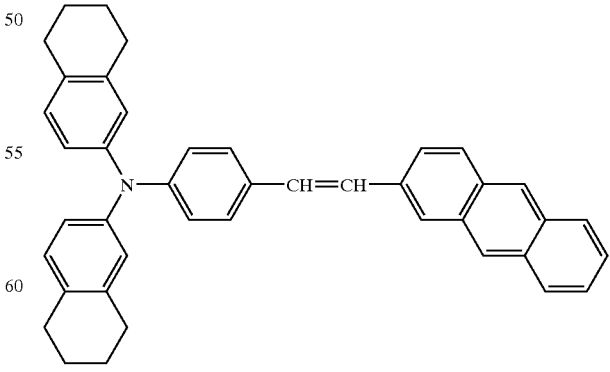
R = C₂H₅, i-C₃H₇, i-C₅H₉, t-C₄H₉,
cyclo-C₆H₁₀C₆H₅

According to the present invention, the compound of the present invention is produced efficiently by a process which comprises condensing an aminobenzaldehyde represented by the following general formula [V] with a phosphonic ester represented by the following general formula [VI] or a phosphonium salt represented by the following general formula [VII], thereby giving an aminostyrylanthracene compound represented by the general formula [I], [II], [III], or [IV] above.

General formula [V]

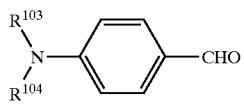

(where, in the general formula [V] above, $R^{103}$ and $R^{104}$ each represent the group corresponding to $R^1$, $R^2$, $R^{11}$, $R^{12}$, $R^{21}$, $R^{22}$, $R^{38}$, or $R^{39}$ mentioned above.)

General formula [VI]

General formula [VII]

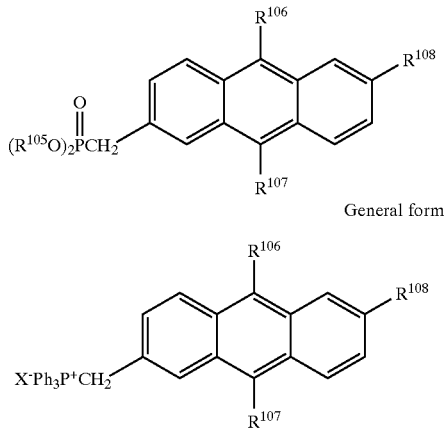

(where, in the general formulas [VI] and [VII] above, $R^{105}$ represents a hydrocarbon group (preferably a saturated hydrocarbon group having 1 to 4 carbons), $R^{106}$ and $R^{107}$ each represent the group corresponding to $R^3$, $R^4$, $R^{13}$, $R^{14}$, $R^{23}$, $R^{24}$, $R^{40}$, or $R^{41}$ mentioned above, $R^{108}$ represents the group corresponding to the $R^5$, $R^{16}$, $R^{25}$, or $R^{42}$ mentioned above, and X represents a halogen atom.)

To be concrete, the process for producing the compound of the present invention comprises performing said condensation by Wittig-Horner reaction or Wittig reaction, treating said phosphonic ester and/or said phosphonium salt with a base in a solvent, thereby giving carboanions, and condensing these carboanions with said aminobenzaldehyde.

The aminostyrylanthracene compound represented by the following general formula (5)

General formula (5)

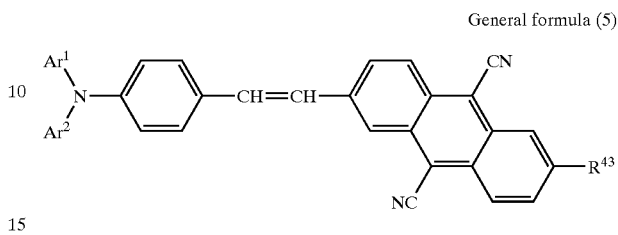

[where, in the general formula (5) above, $Ar^1$, $Ar^2$ and $R^{43}$ are defined as above.] is obtained by condensing 4-(N,N-diarylamino)benzaldehyde represented by the following general formula (38) with a phosphonic ester represented by the following general formula (39) or a phosphonium salt represented by the following general formula (40).

General formula (38)

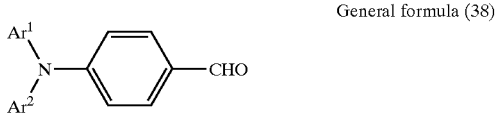

General formula (39)

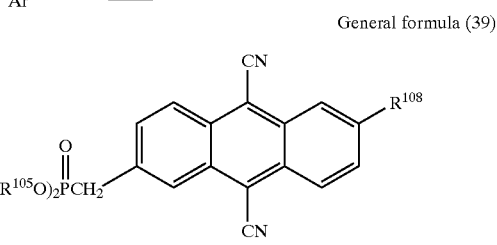

General formula (40)

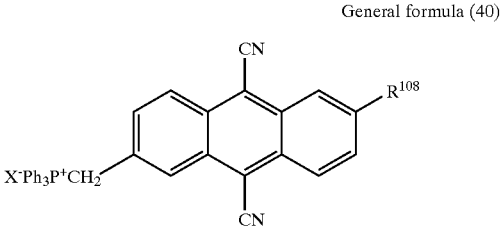

(where, in the general formulas (38), (39), and (40) above, $Ar^1$, $Ar^2$, $R^{105}$, and X are defined as above.)

The reaction may be expressed by the reaction scheme 1 as follows.

Reaction scheme 1

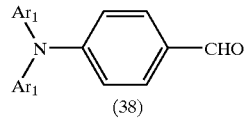
(38)

+

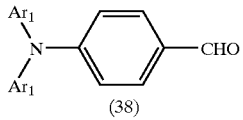
(38)

+

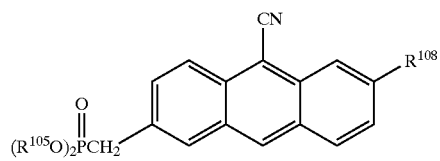 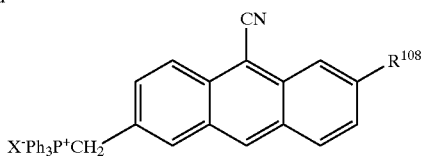

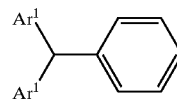

This reaction starts with treatment of the compound represented by the general formula (39) or (40) with a base in an appropriate solvent. This treatment evolves carboanions, which are subsequently condensed with an aldehyde represented by the general formula (38) so that the reaction is completed. Possible base/solvent combinations are as follows.

Sodium hydroxide/water, sodium carbonate/water, potassium carbonate/water, sodium ethoxide/ethanol or dimethylformamide, sodium methoxide/methanol-diethyl ether mixture or dimethylformamide, triethylamine/ethanol or diglyme or chloroform or nitromethane, pyridine/methylene chloride or nitromethane, 1,5-disazabicyclo[4.3.0]non-5-en/dimethylsulfoxide, potassium t-butoxide/dimethylsulfoxide or tetrahydrofuran or benzene or dimethylformamide, phenyl lithium/diethyl ether or tetrahydrofuran, t-butyl lithium/diethyl ether or tetrahydrofuran, sodium amide/ammonia, sodium hydride/dimethylformamide or tetrahydrofuran, triethyl sodium/diethyl ether or tetrahydrofuran, and the like.

This reaction proceeds selectively at a comparative low temperature (−30° C. to 30° C.). Therefore, the desired product can be purified easily by chromatography. Moreover, the compound of the present invention represented by the general formula (5) is highly crystalline and hence can be purified by recrystallization. The method of recrystallization is not specifically restricted. It may be readily accomplished by dissolving in acetone and adding hexane, or by dissolving in toluene with heating and then concentrating and cooling. This reaction may be carried out at normal pressure for 3 to 24 hours.

The process for producing the compound of the present invention gives an aminostyrylanthracene compound represented by the above-mentioned general formula (12), (13), (14), (15), (16), (17), (18), (21), (22), (23), (24), (25), (26), (27), (30), (31), (32), (33), (34), (35), or (36). To be concrete, the process gives an aminostyrylanthracene compound represented by the above-mentioned general formula (19)-1, (19)-2, (19)-3, (19)-4, (19)-5, (19)-6, (19)-7, (19)-8, (19)-9, (19)-10, (19)-11, (19)-12, (28)-1, (28)-2, (28)-3, (28)-4, (28)-5, (28)-6, (28)-7, (28)-8, (28)-9, (28)-10, (28)-11, (28)-12, (37)-1, (37)-2, (37)-3, (37)-4, (37)-5, (37)-6, (37)-7, (37)-8, (37)-9, (37)-10, (37)-11, or (37)-12.

The present invention also provides a variety of compounds suitable as synthetic intermediates for the compound of the present invention.

The synthetic intermediate compound for the aminostyrylanthracene compound represented by the above-mentioned general formula [I], [II], [III], or [IV] is a phosphonic ester represented by the above-mentioned general formula [VI] or a phosphonium salt represented by the above-mentioned general formula [VII].

This synthetic intermediate (referred to as "the synthetic intermediate 1 of the present invention" hereinafter) is typically represented by the following general formula (39), (40), (41), (42), (43), or (44).

General formula (39)

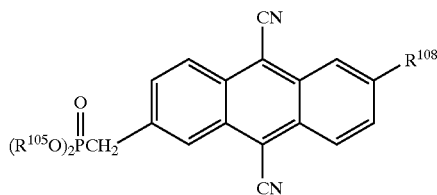

General formula (40)

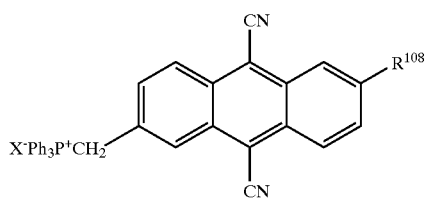

General formula (41)

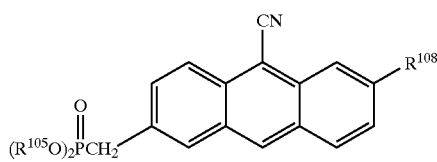

General formula (42)

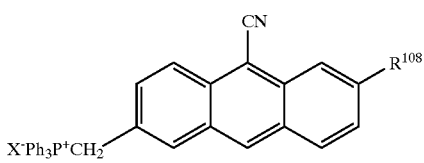

General formula (43)

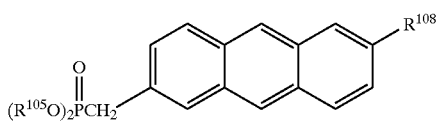

General formula (44)

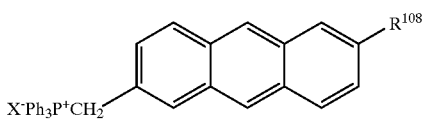

The synthetic intermediate of the present invention may be derived from a synthetic intermediate as its precursor in the following manner.

Reaction between a halogenated aryl compound represented by the following general formula [VIII] and a trialkyl phosphite represented by the following general formula [IX] or triphenylphosphine (PPh₃) gives a phosphonic ester represented by the above-mentioned general formula [VI] or a phosphonium salt represented by the above-mentioned general formula [VII]. This reaction may be carried out without solvent or in a solvent (such as xylene) having a boiling point higher than 120° C. or in a large excess of trialkyl phosphite, at 120–160° C. under normal pressure for 0.5 to 24 hours.

General formula [VIII]

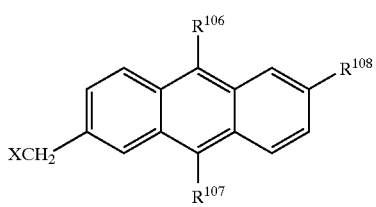

(where, in the general formula [VIII] above, $R^{106}$ and $R^{107}$ are identical or different groups, at least one of them representing a hydrogen atom, cyano group, fluoroalkyl group, nitro group, or halogen atom, $R^{108}$ represents a hydrogen atom, a saturated or unsaturated hydrocarbon group having one or more carbons (preferably 1 to 6 carbons), or an aryl group which may have a substituent, and X represents a halogen atom.)

$$P(OR^{105})_3 \qquad \text{General formula [IX]}$$

(where, in the general formula [IX] above, $R^{105}$ represents a hydrocarbon group, particularly a saturated hydrocarbon group having 1 to 4 carbons.)

The present invention also provides a halogenated aryl compound (referred to as "the synthetic intermediate 2 of the present invention" hereinafter) represented by the above-mentioned general formula [VIII], which is used as a synthetic intermediate to obtain the synthetic intermediate 1.

The synthetic intermediate 2 of the present invention can be obtained by reaction under illumination between an anthracene compound represented by the following general formula [X] and an N-halogenated succinimide represented by the following general formula [XI]. This reaction may be carried out in a solvent (such as carbon tetrachloride, chloroform, benzene, and chlorobenzene) under illumination from a light source (such as high-pressure mercury lamp, low-pressure mercury lamp, xenone lamp, halogen lamp, sunlight, and fluorescent lamp) at 20–120° C. under normal pressure for 30–48 hours.

General formula [X]

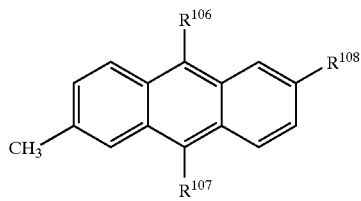

(where, in the general formula [X] above, $R^{106}$ and $R^{107}$ are identical or different groups, at least one of them representing a hydrogen atom, cyano group, fluoroalkyl group, nitro group, or halogen atom, and $R^{108}$ represents a hydrogen atom, a saturated or unsaturated hydrocarbon group having one or more carbons (preferably 1 to 6 carbons), or an aryl group which may have a substituent.)

General formula [XI]

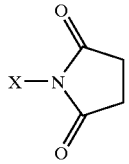

(where, in the general formula [XI] above, X represents a halogen atom.)

The reactions to give the above-mentioned synthetic intermediates 1 and 2 may be expressed by the reaction scheme 2 as follows.

Reaction Scheme 2

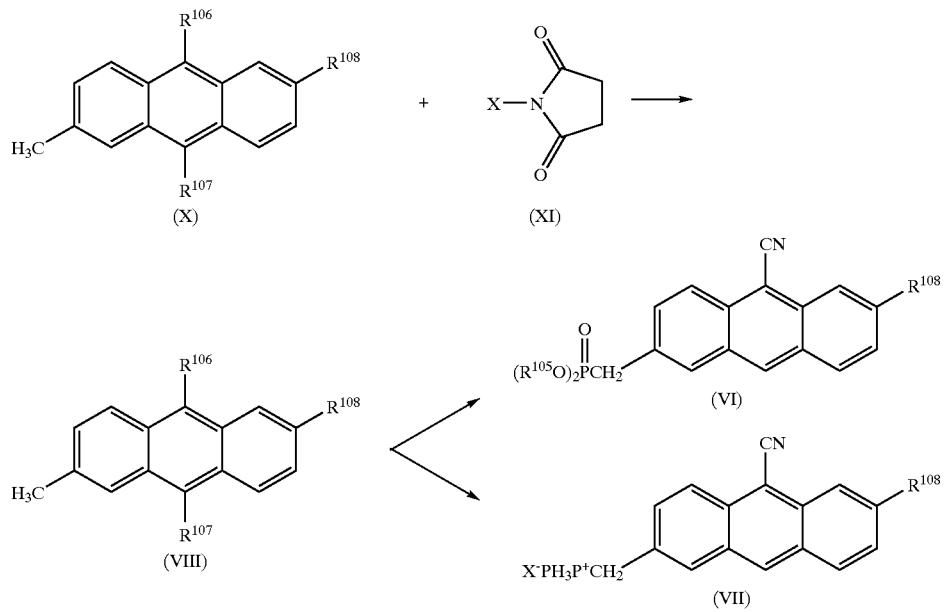

The compound of the present invention is used as an organic luminescent material for the organic electroluminescent element (EL element) illustrated in FIGS. 10 to 13.

FIG. 10 shows a transmission-type organic electroluminescent element A which is designed such that the emitted light 20 passes through the cathode 3 and hence the emitted light 20 is visible from the side of the protective layer 4. FIG. 11 shows a reflection-type organic electroluminescent element B which is designed such that the emitted light 20 is reflected by the cathode 3.

In FIGS. 10 and 11, there is shown a substrate 1 on which is formed the organic electroluminescent element. The substrate may be formed from glass, plastics, or any other appropriated material. In the case where the organic electroluminescent element is used in combination with any other display element, the substrate may be used in common. There is shown a transparent electrode (anode) 2, which may be ITO (indium in oxide) or $SnO_2$.

There is shown an organic luminescent layer 5, which contains the compound of the present invention as a luminescent material. The luminescent layer may have any known layer construction. In the case where either of the hole transfer layer or the electron transfer layer is formed from a luminescent material, the luminescent layer may be formed from these layers placed one over another, as explained later. Both or either of the hole transfer layer and the electron transfer layer may be of laminate structure composed of thin films of a plurality of materials or may be a thin film composed of a plurality of materials. This structure may be used to increase the charge transfer performance to such an extent as to meet the object of the present invention. Another layer structure that can be used to increase the luminescent performance includes one in which a thin film of at least one kind of fluorescent material is interposed between the hole transfer layer and the electron transfer layer, or one in which at least one kind of fluorescent material is contained in both the hole transfer layer and the electron transfer layer. In this case the layer structure may contain an additional thin film to control the hole transfer or electron transfer, thereby improving the luminescence efficiency.

The compound of the present invention is capable of both electron transfer and hole transfer; therefore, it can be used as the light-emitting layer which functions also as the electron transfer layer or as the light-emitting layer which functions also as the hole transfer layer. The electroluminescent element may be constructed such that the light-emitting layer (which is formed from the compound of the present invention) is interposed between the electron transfer layer and the hole transfer layer.

Incidentally, there is shown a cathode 3 in FIGS. 10 and 11. The cathode may be formed from an alloy of active metal (such as Li, Mg, and Ca) and metal (such as Ag, Al, and In), or may be formed from layers of these metals. In the case of an organic electroluminescent element of transmission type, the cathode may have an adequate thickness so that a desired light transmittance is attained for specific uses. In addition, there is shown a sealing/protective layer 4, which entirely covers the organic electroluminescent element to ensure its performance. It can be formed from any material which maintains air tightness. There is shown a power source 8 to supply electric current.

The organic electroluminescent element according to the present invention may have an organic layer of laminated structure (or single-hetero structure) which is composed of a hole transfer layer and an electron transfer layer. In this case, the hole transfer layer or the electron transfer layer may be formed from the compound of the present invention. Alternatively, the organic layer may be of double-hetero structure, in which a hole transfer layer, a light-emitting layer, and an electron transfer layer are sequentially laminated on top of the other. In this case, the light-emitting layer is formed from the compound of the present invention.

An example of the organic electroluminescent element of layer structure as mentioned above is illustrated in FIG. 3. It consists of a transparent substrate 1, a transparent anode 2, an organic layer 5a (composed of a hole transfer layer 6 and an electron transfer layer 7), and a cathode 3, which are sequentially placed on top of the other. The entire laminate structure is sealed with a protective film 4, which is Organic electroluminescent element C of single-hetero structure.

The element of layer structure shown in FIG. 12 (in which the light-emitting layer is omitted) emits light 20 of desired wavelength from the interface between the hole transfer layer 6 and the electron transfer layer 7. The emitted light is visible through the substrate 1.

An example of laminate structure shown in FIG. 13 consists of a transparent substrate 1, a transparent anode 2, an organic layer 5b (composed of a hole transfer layer 10, a light-emitting layer 11, and an electron transfer layer 12), and a cathode 3, which are sequentially placed on top of the other. The entire laminate structure is sealed with a protective film 4, which is Organic electroluminescent element D of double-hetero structure.

The organic electroluminescent element shown in FIG. 13 works as follows. A dc voltage applied across the anode 2 and the cathode 3 causes holes (injected from the anode 2) to reach the light-emitting layer 11 through the hole transfer layer 10 and also causes electrons (injected from the cathode 3) to reach the light-emitting layer 11 through the electron transfer layer 12. As the result, recombination of electrons and holes takes place in the light-emitting layer 11, thereby giving rise to singlet excitons which emit light of desired wavelength.

In the above-mentioned organic electroluminescent elements C and D, the substrate 1 may be formed from any transparent material such as glass and plastics. If this element is used in combination with other display element or if the elements of laminate structure as shown in FIGS. 12 and 13 are arranged in a matrix, one substrate may be used in common. Also, the elements C and D may be either of transmission type or of reflection type.

The anode 2 is a transparent electrode, which may be made of ITO (indium tin oxide) or $SnO_2$. A thin film of organic substance or organometallic compound may be interposed between the anode 2 and the hole transfer layer 6 (or 10) for improvement in the charge injection efficiency. In the case where the protective film 4 is made of an electrically conductive material such as metal, then the anode 2 may be surrounded by an insulating film.

In the organic electroluminescent element C, the organic layer 5a is composed of the hole transfer layer 6 and the electron transfer layer 7, and the compound of the present invention is contained in either of them. In this case, the hole transfer layer 6 or the electron transfer layer 7 emits light. In the organic electroluminescent element D, the organic layer 5b is composed of the hole transfer layer 10, the light-emitting layer 11 (containing the compound of the present invention), and the electron transfer layer 12 which are laminated on top of the other. The layer structure may be modified in some other ways. For example, either or both of the hole transfer layer and the electron transfer layer may have the light-emitting function.

In a preferred embodiment, the hole transfer layer 6 or the electron transfer layer 7 or the light-emitting layer 11 should be made of the compound of the present invention by vapor deposition. In this case, the compound of the present invention may be used alone or in combination with another hole or electron transfer material (such as aromatic amine and pyrazoline). In addition, the hole transfer layer may be constructed of laminate of several kinds of hole transfer materials for improvement in the hole transfer performance.

In the organic electroluminescent element C, the light-emitting layer may be the electron transferring light-emitting layer 7. In this case, light is emitted from the hole transfer layer 6 or the interface thereof depending on voltage applied from the power source 8. Likewise, in the organic electroluminescent element D, the electron transfer layer 12 or the hole transfer layer 10 may also function as the light-emitting layer 11. A desirable structure for improved light-emitting performance is such that a light-emitting layer 11 containing at least one kind of fluorescent material is interposed between the hole transfer layer 11 and the electron transfer layer 12. Alternatively, the fluorescent material may be contained in either or both of the hole transfer layer and the electron transfer layer. In this case, the layer structure may contain a thin film (such as hole blocking layer and exciton generating layer) to control the transfer of holes or electrons for improvement in the light-emitting performance.

The cathode 3 may be formed from an alloy of active metal (such as Li, Mg, and Ca) and metal (such as Ag, Al, and In). These metals may be used in the form of laminated layers. The thickness and material of the cathode should be properly selected according to the use of the organic electroluminescent element.

The protective film 4 functions as a sealing film. It should cover the organic electroluminescent element entirely so as to improve the charge injection efficiency and the light-emitting efficiency. It may be formed from any material (such as aluminum, gold, and chromium in the form of metal or alloy) so long as it keeps air tightness.

The above-mentioned organic electroluminescent elements works upon application of direct current. However, it may be operated by pulse current or alternating current. The magnitude of current and voltage is not specifically restricted so long as the element is not broken. It is desirable that the element emit light efficiency with a small amount of electric energy in view of the power consumption and life of the organic electroluminescent elements.

The organic electroluminescent elements of the present invention maybe used to construct a flat display as shown in FIG. 14. For full-color display, the organic layer 5 (5a, 5b), each capable of emitting primary color of red (R), green (G), and blue (B), are interposed between the cathode 3 and the anode 2. The cathode 3 and anode 2 may be stripes intersecting each other. Each element is selected by the luminance signal circuit 14 and the control circuit 15 having a shift register. A signal voltage is applied according to the selection, so that the organic layer (pixel) at the intersection of the selected cathode 3 and anode 2 emits light.

An example of passive matrix (8×3 RGB) is shown in FIG. 14. It is constructed such that a laminate 5 is interposed between the cathode 3 and the anode 2. This laminate is composed of the hole transfer layer and at least either of the light-emitting layer and the electron transfer layer. (See FIGS. 12 and 13.) Both the cathode and the anode are patterned in stripe form so that they intersect each other at right angles. Signal voltage is applied sequentially by the control circuits 14 and 15 (with a shift register). The element at the intersection emits light. The EL element constructed in this way can be used as a display for characters and signs and it can also be used as an image reproducing apparatus. If the stripe pattern of the cathode 3 and anode 2 is arranged for each of red (R), green (G), and blue (B) colors, a multi-color or full-color solid flat display panel can be constructed.

DETAILED DESCRIPTION OF THE INVENTION

The invention will be described in more detail with reference to the following examples, which are not intended to restrict the scope thereof.

EXAMPLE 1

Synthesis of Aminostyrylanthracene Compound (19)-7

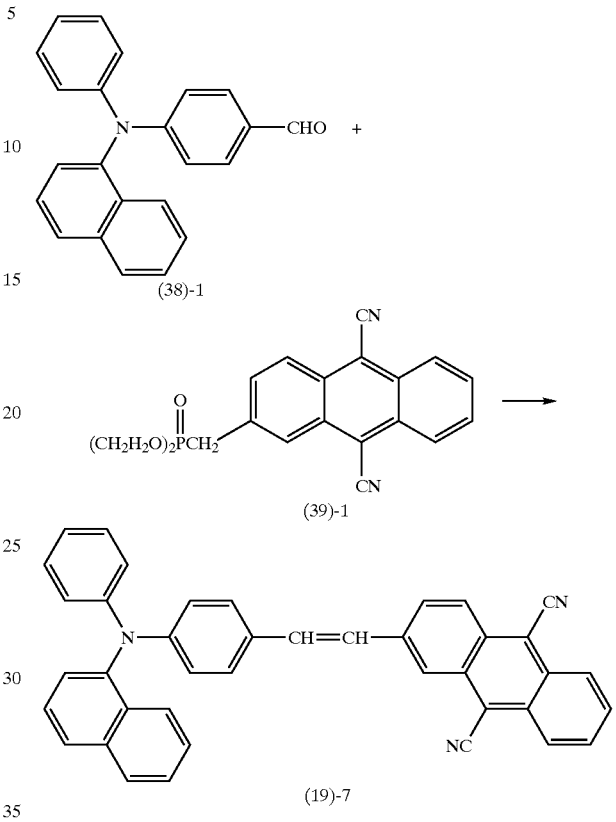

A reactor was charged with 3.75 mmol of sodium hydride (in mineral oil), which was subsequently suspended in 5 mL of anhydrous tetrahydrofuran in an atmosphere of nitrogen. To the reactor was added dropwise with stirring at room temperature a solution of 471 mg (1.24 mmol) of phosphonic ester (39)-1 and 521 mg (1.61 mmol) of 4-[N-(1-naphthyl)-N-phenylamino]benzaldehyde (38)-1 dissolved in 70 mL of 6:1 mixed solvent of anhydrous tetrahydrofuran and anhydrous dimethylformamide. Reaction was carried out with stirring at room temperature for 12 hours. The reaction mixture was quenched with a small amount of ice, washed with a saturated aqueous solution of sodium chloride, and dried with anhydrous sodium sulfate. The reaction solution was concentrated. Upon addition of water, the concentrated reaction solution gave precipitates. The precipitates were washed sequentially with water, ethanol, and hexane.

The reaction product was purified by silica gel chromatography (WAKO-gel C-300, toluene), and the purified product was recrystallized from toluene. Thus there were obtained red crystals (383 mg). Upon analysis by $^1$H-NMR and FAB-MS, the reaction product was identified as the desired compound (19)-7.

Yield: 56%.

The analytical data are as follows.

$^1$H-NMR (CDCl$_3$) δ (ppm): 6.99–7.54(15H, m), 7.79–7.95(4H, m), 8.08(2H, d), 8.34(1H, s), 8.42–8.50(3H, m).

Glass transition point: 137° C., melting point: 312° C.

Figure 1:
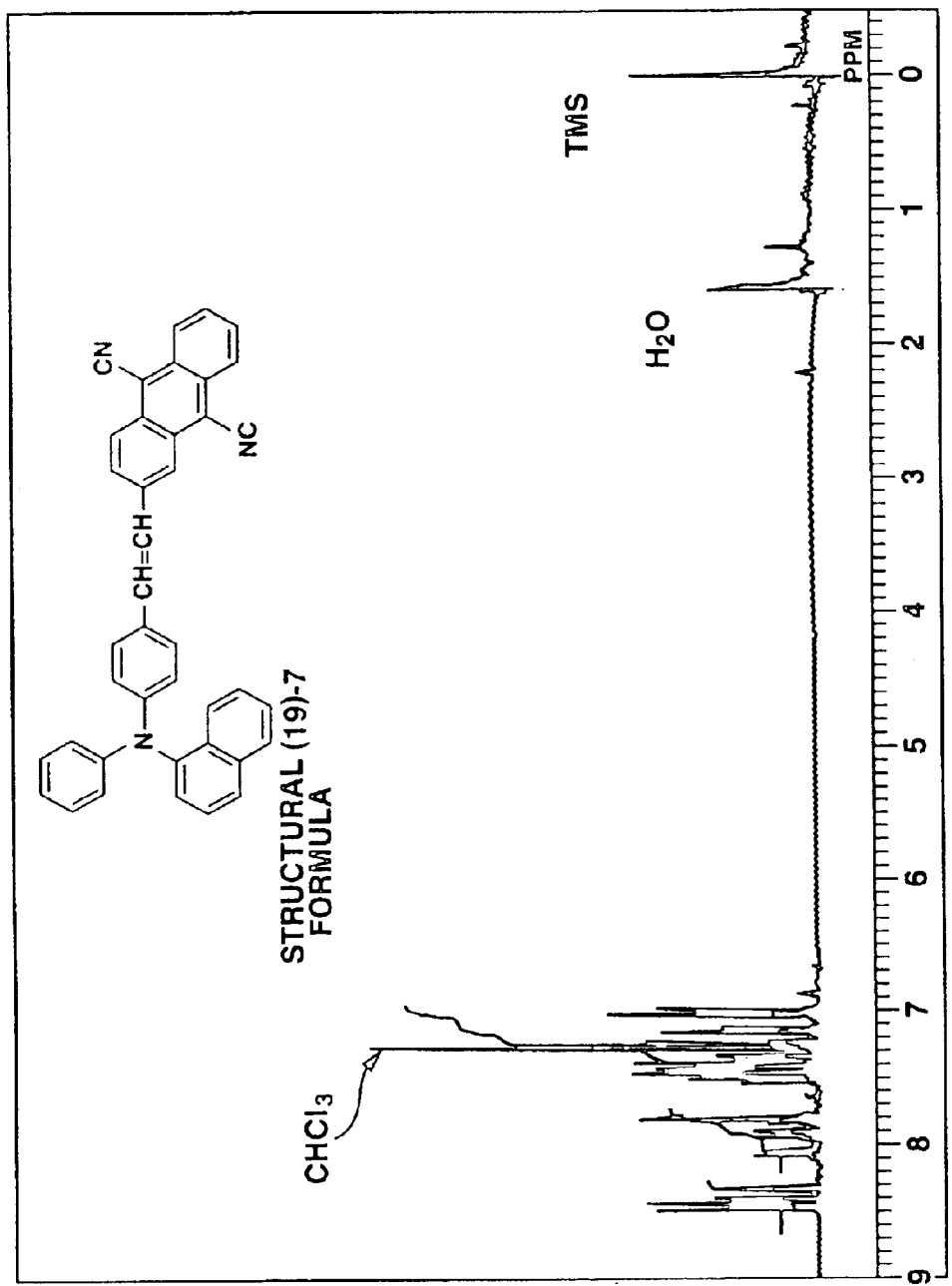
FIG. 1 is a $^1$H-NMR spectrum of the compound obtained in Example 1 of the present invention.

The desired compound was found to have a maximum visible absorption at 511 nm and a maximum fluorescence wavelength at 615 nm. The ¹H-NMR spectrum is shown in FIG. 1.

EXAMPLE 2

Synthesis of Aminostyrylanthracene Compound (19)-8

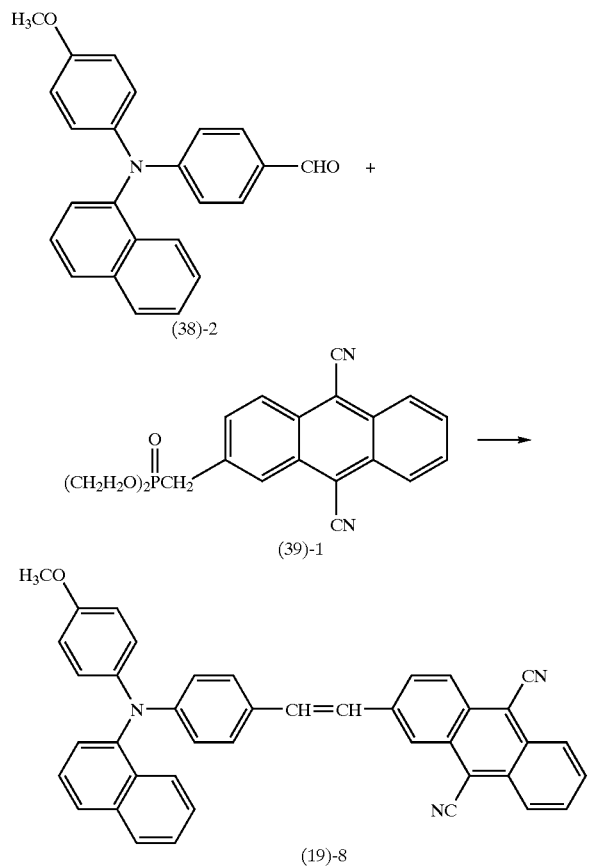

A reactor was charged with 3.75 mmol of sodium hydride (in mineral oil), which was subsequently suspended in 5 mL of anhydrous tetrahydrofuran in an atmosphere of nitrogen. To the reactor was added dropwise with stirring at room temperature a solution of 471 mg (1.24 mmol) of phosphonic ester (39)-1 and 521 mg (1.47 mmol) of 4-[N-(4-methoxyphenyl)-N-(1-naphthyl)amino]benzaldehyde (38)-2 dissolved in 70 mL of 6:1 mixed solvent of anhydrous tetrahydrofuran and anhydrous dimethylformamide. Reaction was carried out with stirring at room temperature for 12 hours. The reaction mixture was quenched with a small amount of ice, washed with a saturated aqueous solution of sodium chloride, and dried with anhydrous sodium sulfate. The reaction solution was concentrated. Upon addition of water, the concentrated reaction solution gave precipitates. The precipitates were washed sequentially with water, ethanol, and hexane.

The reaction product was purified by silica gel chromatography (WAKO-gel C-300, toluene), and the purified product was recrystallized from toluene. Thus there were obtained red crystals (417 mg). Upon analysis by ¹H-NMR and FAB-MS, the reaction product was identified as the desired compound (19)-8.

Yield: 34%.

The analytical data are as follows.

¹H-NMR (CDCl₃) δ (ppm): 3.80(3H, s), 6.86(4H, d), 7.14–7.53(1H, d), 7.81(3H, m) 7.90–7.98(2H, m), 8.07(2H, d), 8.31(1H, s), 8.40–8.48(3H, m).

Figure 2:
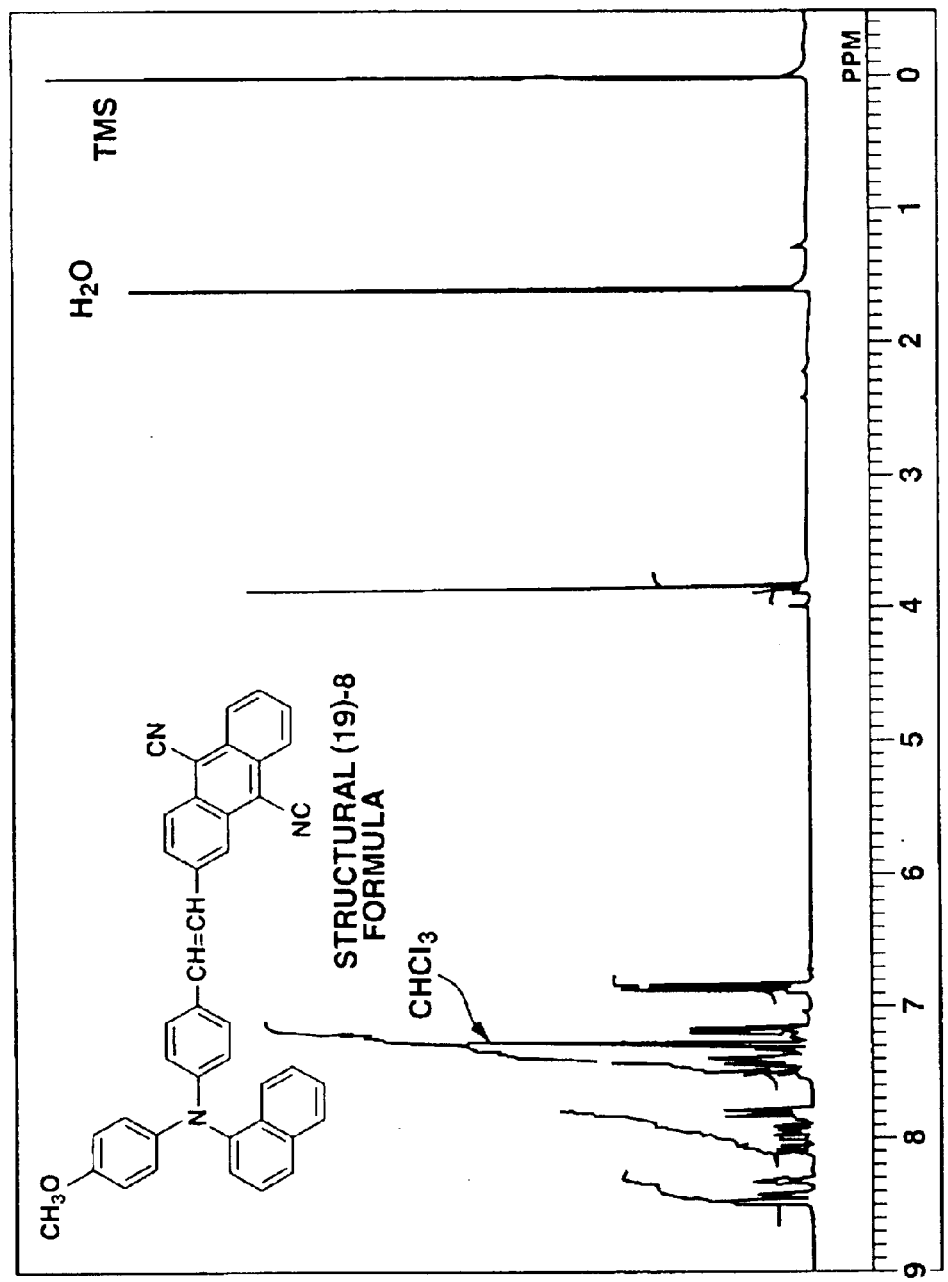
FIG. 2 is a $^1$H-NMR spectrum of the compound obtained in Example 2 of the present invention.

The desired compound was found to have a maximum visible absorption at 527 nm and a maximum fluorescence wavelength at 640 nm. The ¹H-NMR spectrum is shown in FIG. 2.

EXAMPLE 3

Synthesis of Aminostyrylanthracene Compound (19)-9

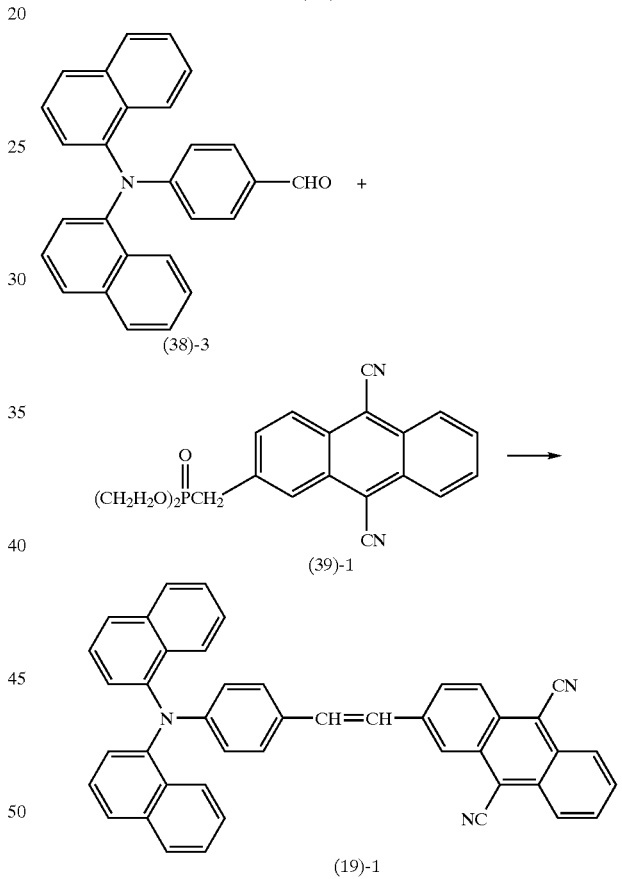

A reactor was charged with 7.50 mmol of sodium hydride (in mineral oil), which was subsequently suspended in 10 mL of anhydrous tetrahydrofuran in an atmosphere of nitrogen. To the reactor was added dropwise with stirring at room temperature a solution of 500 mg (1.32 mmol) of phosphonic ester (39)-1 and 758 mg (2.03 mmol) of 4-[N,N-di(1-naphthyl)amino]benzaldehyde (38)-3 dissolved in 70 mL of 3:1 mixed solvent of anhydrous tetrahydrofuran and anhydrous dimethylformamide. Reaction was carried out with stirring at room temperature for 12 hours. The reaction mixture was quenched with a small amount of ice, washed with a saturated aqueous solution of sodium chloride, and dried with anhydrous sodium sulfate. The reaction solution was concentrated. Upon addition of water, the concentrated reaction solution gave precipitates. The precipitates were washed sequentially with water, ethanol, and hexane.

The reaction product was purified by silica gel chromatography (WAKO-gel C-300, toluene), and the purified product was recrystallized from toluene. Thus there were obtained red crystals (443 mg). Upon analysis by $^1$H-NMR and FAB-MS, the reaction product was identified as the desired compound (19)-9.

Yield: 55%.

The analytical data are as follows.

$^1$H-NMR (CDCl$_3$) δ (ppm): 6.70(2H, d), 7.15–7.50(12H, m), 7.74–7.82(4H, m), 7.92(2H, m), 8.06(3H, m), 8.31(1H, s), 8.41–8.49(3H, s).

Glass transition point: 165° C., melting point: 314° C.

Figure 3:
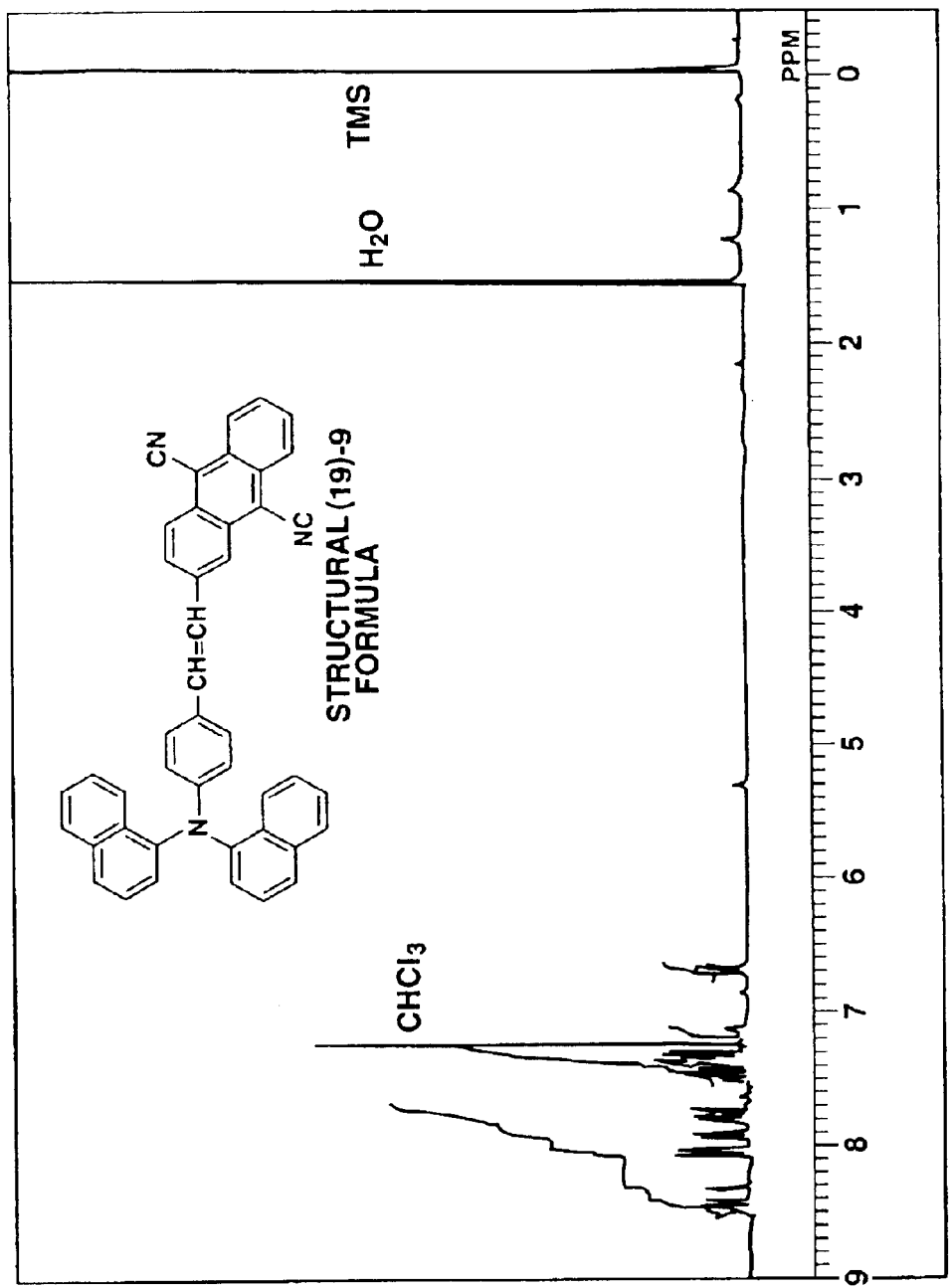
FIG. 3 is a $^1$H-NMR spectrum of the compound obtained in Example 3 of the present invention.

The desired compound was found to have a maximum visible absorption at 514 nm and a maximum fluorescence wavelength at 610 nm. The $^1$H-NMR spectrum is shown in FIG. 3.

EXAMPLE 4

Synthesis of Aminostyrylanthracene Compound (19)-10

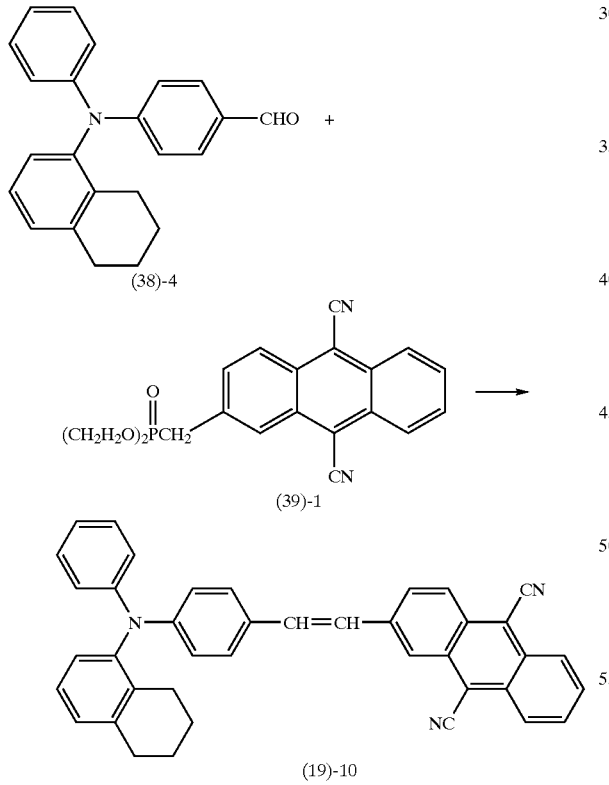

A reactor was charged with 1.56 mmol of sodium hydride (in mineral oil), which was subsequently suspended in 5 mL of anhydrous tetrahydrofuran in an atmosphere of nitrogen. To the reactor was added dropwise with stirring and ice cooling a solution of 200 mg (0.53 mmol) of phosphonic ester (39)-1 and 208 mg (0.63 mmol) of 4-[N-phenyl-N-(5, 6,7,8-tetrahydro-1-naphthylamino)]benzaldehyde (38)-4 dissolved in 40 mL of 4:1 mixed solvent of anhydrous tetrahydrofuran and anhydrous dimethylformamide. Reaction was carried out with ice cooling for 3 hours and then with stirring at room temperature for 12 hours. The reaction mixture was quenched with a small amount of ice, washed with a saturated aqueous solution of sodium chloride, and dried with anhydrous sodium sulfate. The reaction solution was concentrated. Upon addition of water, the concentrated reaction solution gave precipitates. The precipitates were washed sequentially with water, ethanol, and hexane.

The reaction product was purified by silica gel chromatography (WAKO-gel C-300, toluene), and the purified product was recrystallized from toluene. Thus there were obtained red crystals (196 mg). Upon analysis by $^1$H-NMR and FAB-MS, the reaction product was identified as the desired compound (19)-10.

Yield: 56%.

The analytical data are as follows.

$^1$H-NMR (CDCl$_3$) δ (ppm): 1.72(4H, m), 2.40(2H, m), 2.84(2H, m), 6.94–7.44(12H, m), 7.46(2H, d), 7.83(2H, m), 8.08(1H, d), 8.35(1H, s), 8.42–8.50(3H, m).

Glass transition point: 309° C.

Figure 4:
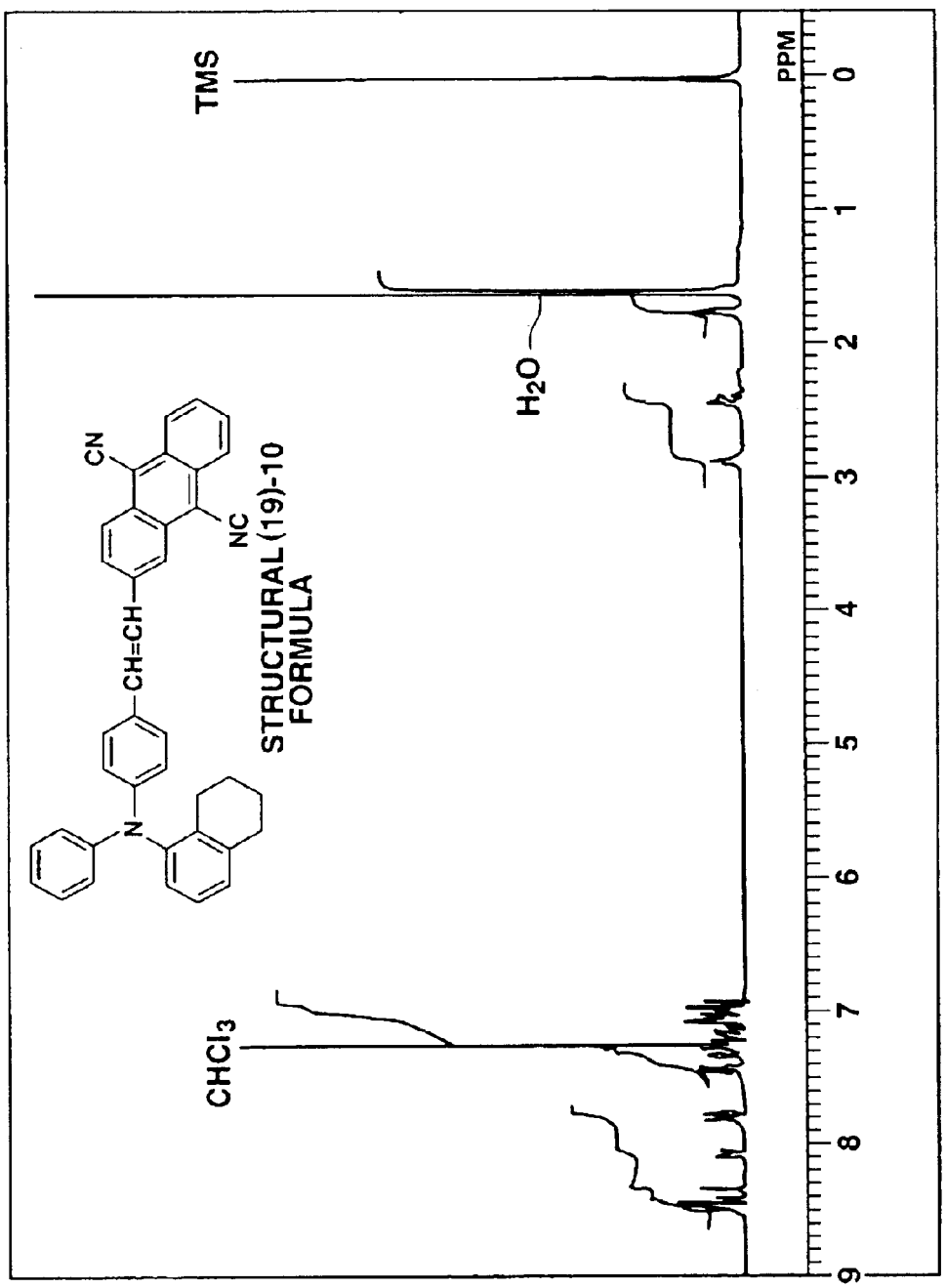
FIG. 4 is a $^1$H-NMR spectrum of the compound obtained in Example 4 of the present invention.

The desired compound was found to have a maximum visible absorption at 515 nm and a maximum fluorescence wavelength at 630 nm. The $^1$H-NMR spectrum is shown in FIG. 4.

EXAMPLE 5

Synthesis of Aminostyrylanthracene Compound (19)-11

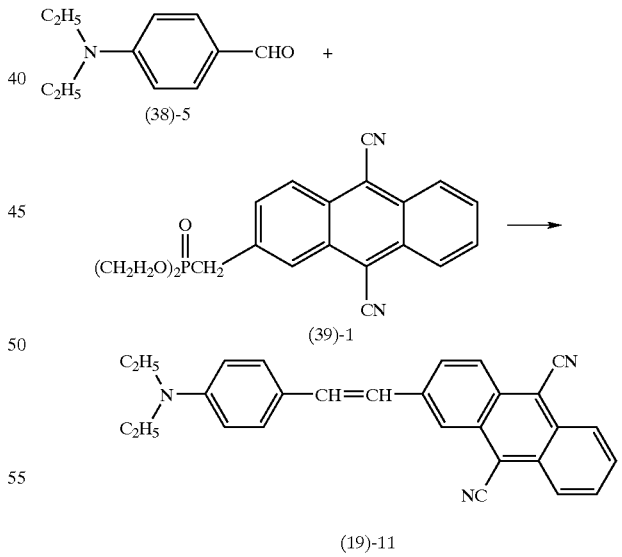

A reactor was charged with 3.75 mmol of sodium hydride (in mineral oil), which was subsequently suspended in 10 mL of anhydrous tetrahydrofuran in an atmosphere of nitrogen. To the reactor was added dropwise with stirring at room temperature a solution of 470 mg (1.24 mmol) of phosphonic ester (39)-1 and 330 mg (1.86 mmol) of 4-(N,N-diethyamino)benzaldehyde (38)-5 dissolved in 80 mL of 7:1 mixed solvent of anhydrous tetrahydrofuran and anhydrous dimethylformamide. Reaction was carried out with stirring at room temperature for 12 hours. The reaction mixture was quenched with a small amount of ice, washed with a saturated aqueous solution of sodium chloride, and dried with anhydrous sodium sulfate.

The reaction product was purified by silica gel chromatography (WAKO-gel C-300, toluene:THF=10:1), and the purified product was recrystallized from toluene. Thus there were obtained red-brown crystals (280 mg). Upon analysis by $^1$H-NMR and FAB-MS, the reaction product was identified as the desired compound (19)-11. Yield: 56%

The analytical data are as follows.

$^1$H-NMR (CDCl$_3$) δ (ppm): 1.22(6H,t), 3.43(4H,q), 6.72 (2H, d), 7.14(1H, d), 7.37(1H, d), 7.50(2H, d), 7.81(2H, m), 8.08(1H, d), 8.30(2H, s), 8.40–8.48(3H, m).

Glass transition point: 109° C., melting point: 266° C.

Figure 5:
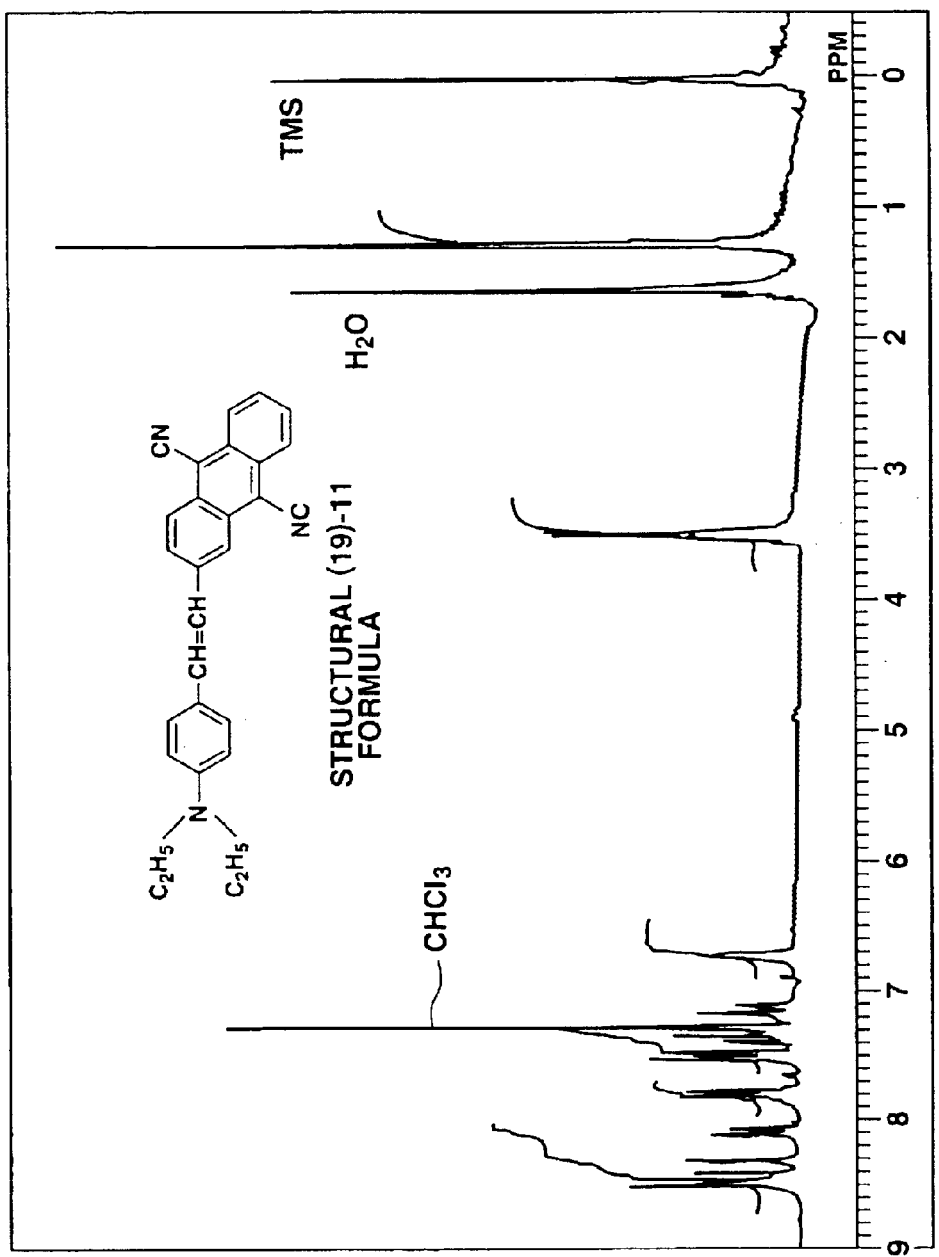
FIG. 5 is a $^1$H-NMR spectrum of the compound obtained in Example 5 of the present invention.

The desired compound was found to have a maximum visible absorption at 540 nm and a maximum fluorescence wavelength at 665 nm. The $^1$H-NMR spectrum is shown in FIG. 5.

EXAMPLE 6

Synthesis of Aminostyrylanthracene Compound (19)-6

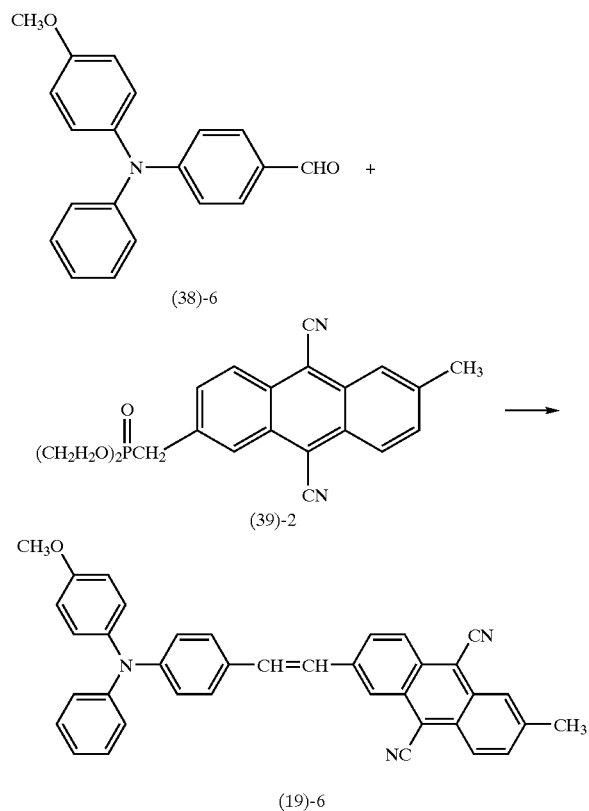

A reactor was charged with 3.75 mmol of sodium hydride (in mineral oil), which was subsequently suspended in 10 mL of anhydrous tetrahydrofuran in an atmosphere of nitrogen. To the reactor was added dropwise with stirring at room temperature a solution of 470 mg (1.24 mmol) of phosphonic ester (39)-2 and 570 mg (1.86 mmol) of 4-[N-(4-methoxyphenyl)-N-phenylamino]benzaldehyde (38)-6 dissolved in 120 mL of 1:1 mixed solvent of anhydrous tetrahydrofuran and anhydrous dimethylformamide. Reaction was carried out with stirring at room temperature for 12 hours. The reaction mixture was quenched with a small amount of ice, washed with a saturated aqueous solution of sodium chloride, and dried with anhydrous sodium sulfate.

The reaction product was purified by silica gel chromatography (WAKO-gel C-300, toluene), and the purified product was recrystallized from toluene. Thus there were obtained red-brown crystals (150 mg). Upon analysis by $^1$H-NMR and FAB-MS, the reaction product was identified as the desired compound (19)-6. Yield: 22%

The analytical data are as follows.

$^1$H-NMR (CDCl$_3$) δ (ppm): 2.67(3H, s), 3.83(3H, s), 6.87(2H, d), 6.88–7.39(5H, m), 7,45(2H, d), 7.65(1H, d), 8.05(1H, d), 8.23(1H, s), 8.33–8.43(3H, m).

Melting point: 279° C.

Figure 6:
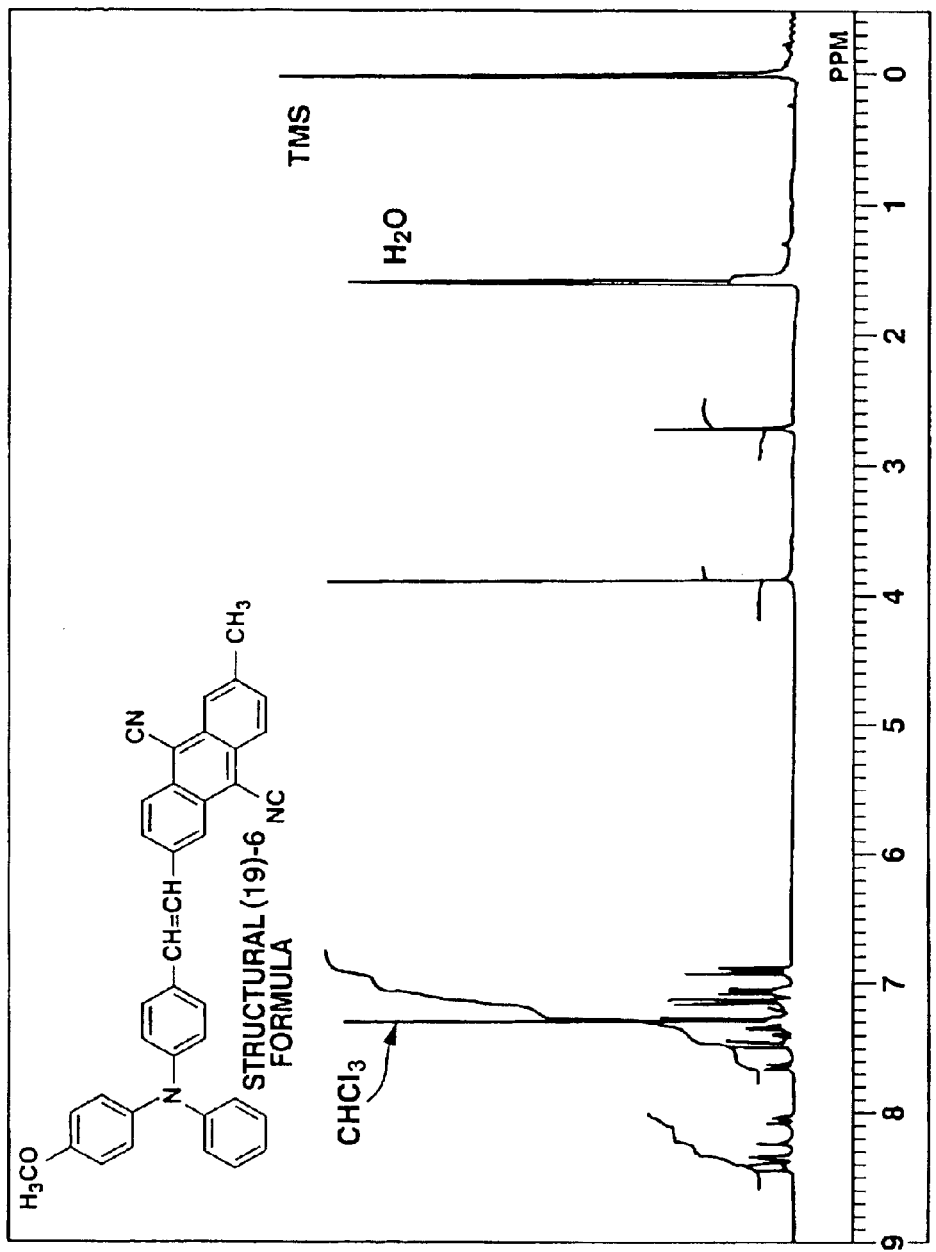
FIG. 6 is a $^1$H-NMR spectrum of the compound obtained in Example 6 of the present invention.

The desired compound was found to have a maximum visible absorption at 520 nm and a maximum fluorescence wavelength at 640 nm. The $^1$H-NMR spectrum is shown in FIG. 6.

EXAMPLE 7

Synthesis of Aminostyrylanthracene Compound (19)-12

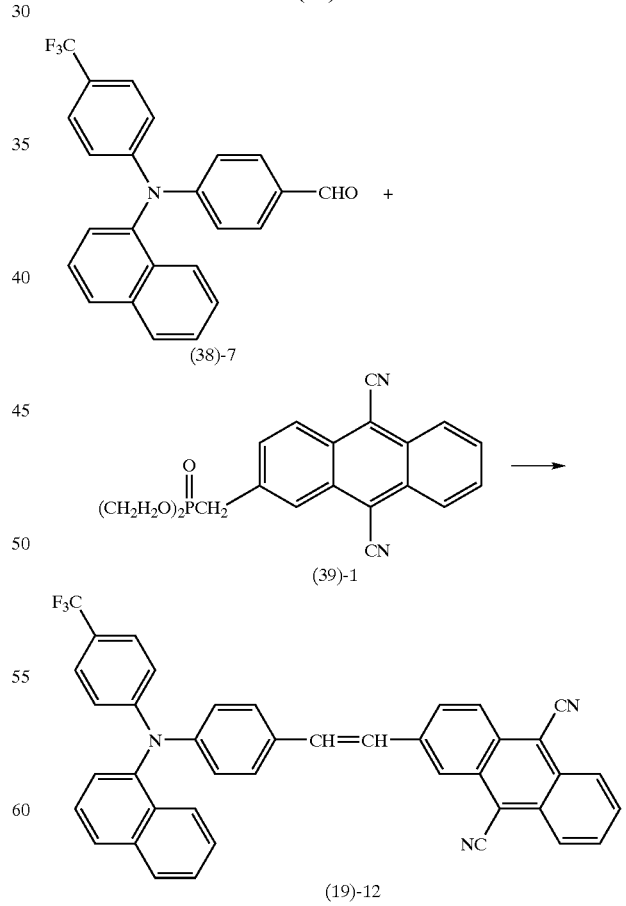

A reactor was charged with 0.158 g (3.96 mmol) of sodium hydride (in mineral oil), which was subsequently suspended in 20 mL of anhydrous tetrahydrofuran in an atmosphere of nitrogen. To the reactor was added dropwise with ice cooling and stirring a solution of 200 mg (0.53 mmol) of phosphonic ester (39)-1 and 621 mg (1.59 mmol) of 4-[N,N-(1-naphthyl-4-trifluoromethylphenyl)] benzaldehyde (38)-7 dissolved in 40 mL of 9:1 mixed solvent of anhydrous tetrahydrofuran and anhydrous dimethylformamide. Reaction was carried out with ice cooling and stirring for 12 hours. The reaction mixture was quenched with a small amount of ice, extracted with toluene, washed with a saturated aqueous solution of sodium chloride, and dried with anhydrous sodium sulfate.

The reaction product was purified by silica gel chromatography (WAKO-gel C-300, toluene:hexane=1:4), and the purified product was recrystallized from acetone-hexane. Thus there were obtained red-brown crystals (371 mg). Upon analysis by $^1$H-NMR and FAB-MS, the reaction product was identified as the desired compound (19)-12. Yield: 46%

The analytical data are as follows.

$^1$H-NMR (CDCl$_3$) δ (ppm): 7.08(2H, d), 7.15(2H, d), 7.35–7.57(10H, m), 7.80–7.89(4H, m), 7.94(1H, d), 8.07 (1H, d), 8.37(1H, s), 8.44–8.50(3H, m).

Glass transition point: 134° C., melting point: 303° C.

Figure 7:
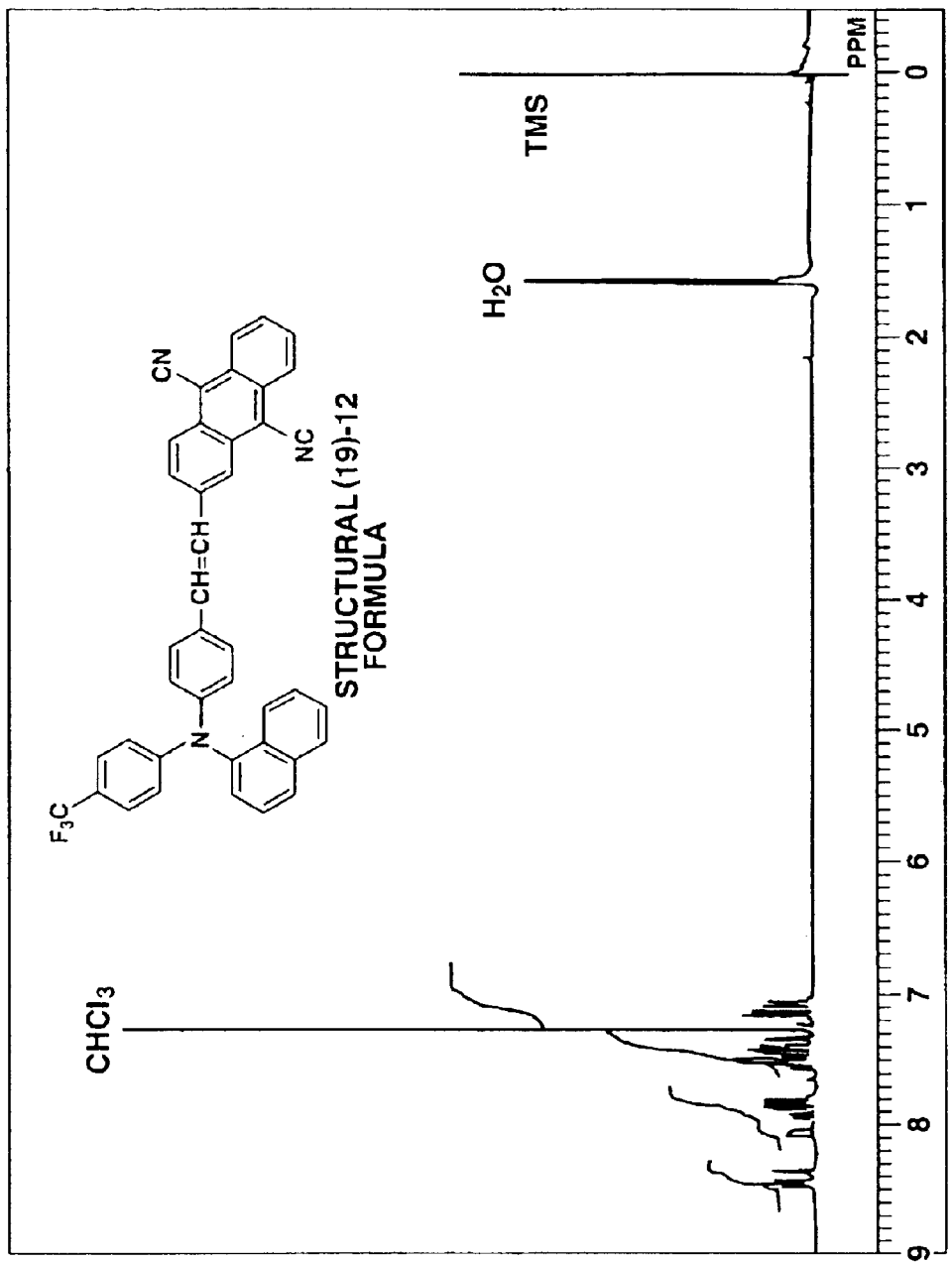
FIG. 7 is a $^1$H-NMR spectrum of the compound obtained in Example 7 of the present invention.

The desired compound was found to have a maximum visible absorption at 510 nm and a maximum fluorescence wavelength at 617 nm. It is interesting that the red color of the desired product is closer to the standard value than that of the compound (19)-7 in Example 1. The $^1$H-NMR spectrum is shown in FIG. 7.

EXAMPLE 8

Synthesis of Phosphonic Ester (39)-1

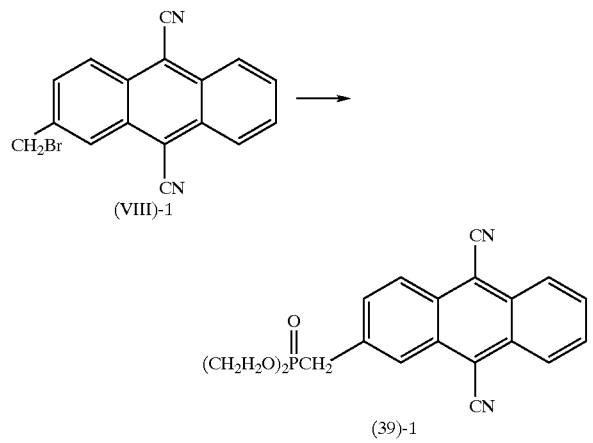

In 60 mL of xylene was suspended 947 mg (2.95 mmol) of 2-(bromomethyl)anthracene-9,10-dicarbonitrile [VII]-1. To the suspension was added dropwise 2.48 g (14.9 mmol) of tributyl phosphite. Reaction was carried out with stirring at 125° C. for 15 hours.

The reaction solution was cooled to room temperature and then given 100 mL of hexane. The solution was allowed to stand for precipitation. The precipitates were washed with hexane repeatedly. Thus there were obtained yellow crystals (942 mg). Upon analysis by $^1$H-NMR and FAB-MS, the reaction product was identified as the desired compound (39)-1. Yield: 84%

The analytical data are as follows.

$^1$H-NMR (CDCl$_3$) δ (ppm): 1.30(6H,t), 3.47(4H, d), 4.12 (8H,q), 7.85(3H, m), 8.38(1H, d), 8.51(3H, m).

Figure 8:
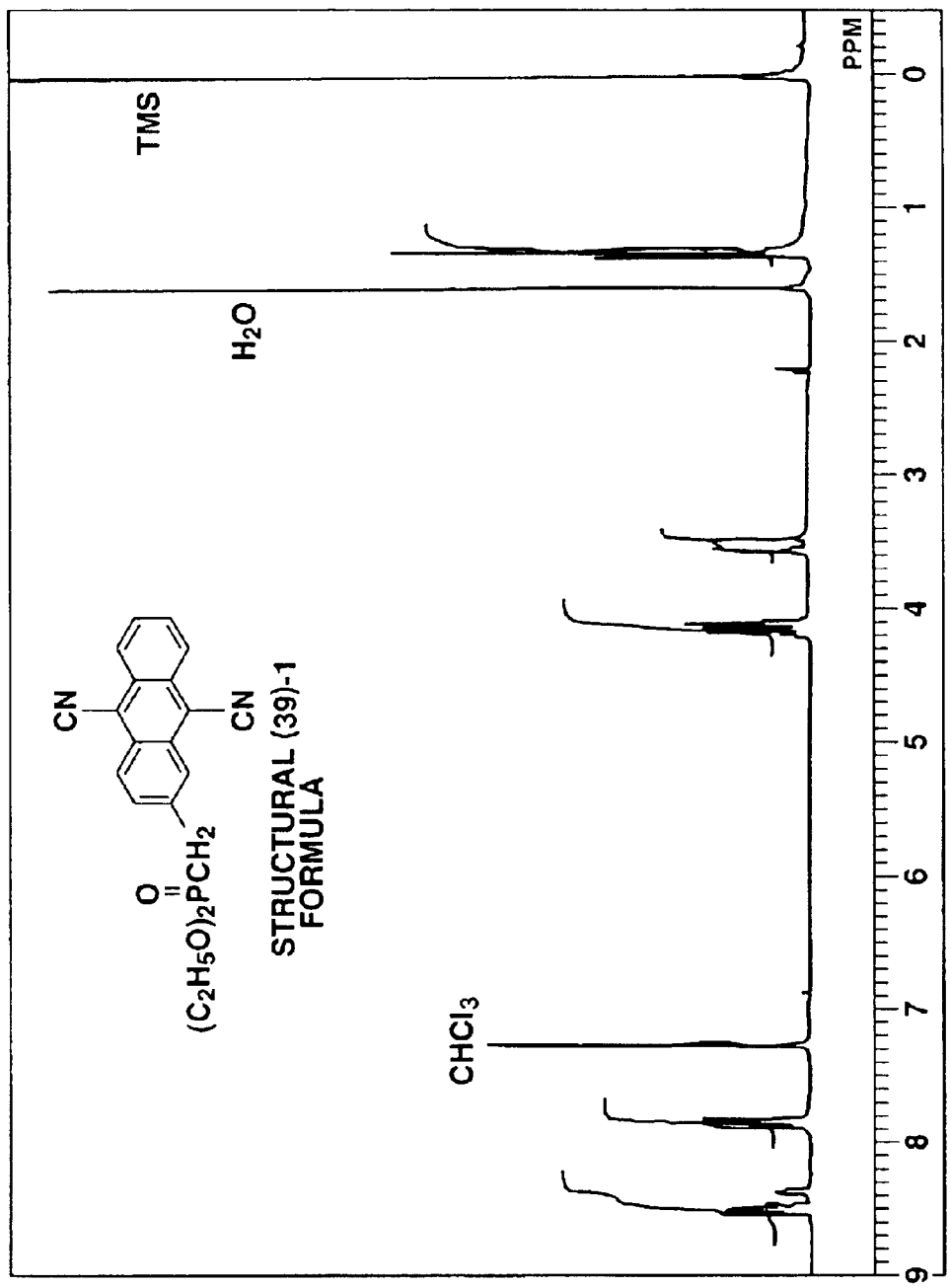
FIG. 8 is a $^1$H-NMR spectrum of the compound obtained in Example 8 of the present invention.

The $^1$H-NMR spectrum is shown in FIG. 8.

EXAMPLE 9

Synthesis of 2-(bromomethyl)anthracene-9,10-dicarbonitrile [VIII]-1

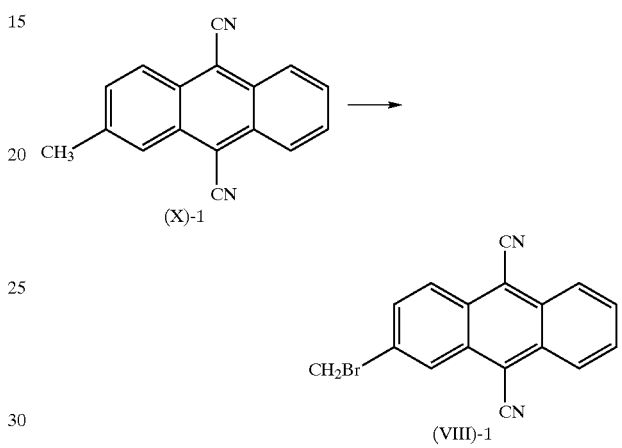

In 200 mL of chloroform was dissolved 800 mg (3.30 mmol) of 2-anthracene-9,10-dicarbonitrile [X]-1. The atmosphere in the reactor was replaced with nitrogen. To the solution was added 5.76 g (32.4 mmol) of N-bromosuccinimide with refluxing in six portions at intervals of 12 hours.

The reaction solution was concentrated, and the concentrated solution was purified by alumina chromatography (active alumina, 300 mesh, chloroform). Precipitates were filtered off and washed repeatedly with hexane. Thus there were obtained yellow crystals (947 mg). Upon analysis by $^1$H-NMR and FAB-MS, the reaction product was identified as the desired compound [VIII]-1. Yield: 89%

The analytical data are as follows.

$^1$H-NMR (CDCl$_3$) δ (ppm): 4.75(2H, s), 7.88(3H, m), 8.47–8.55(4H, m).

Figure 9:
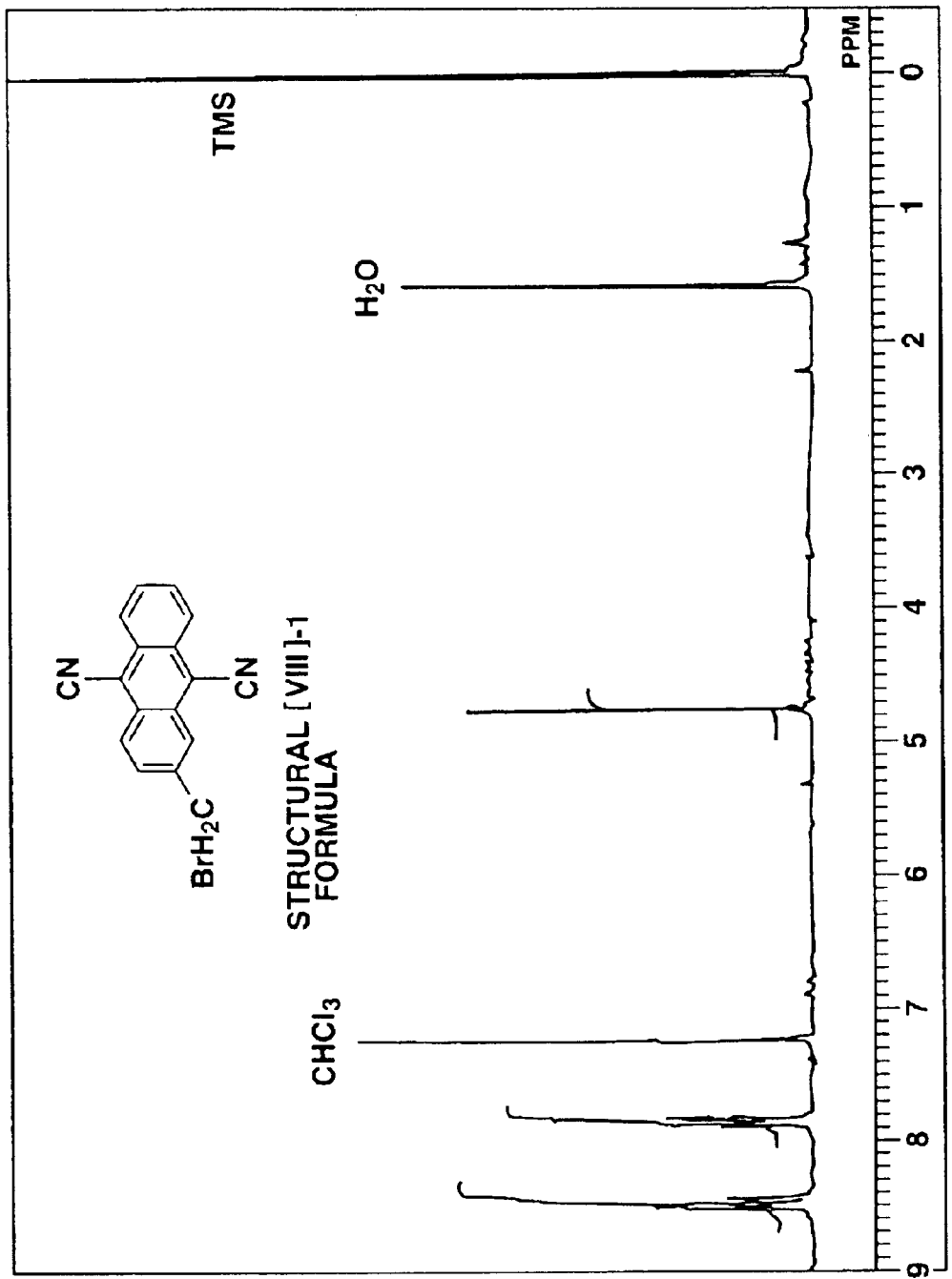
FIG. 9 is a $^1$H-NMR spectrum of the compound obtained in Example 9 of the present invention.
Figure 10:
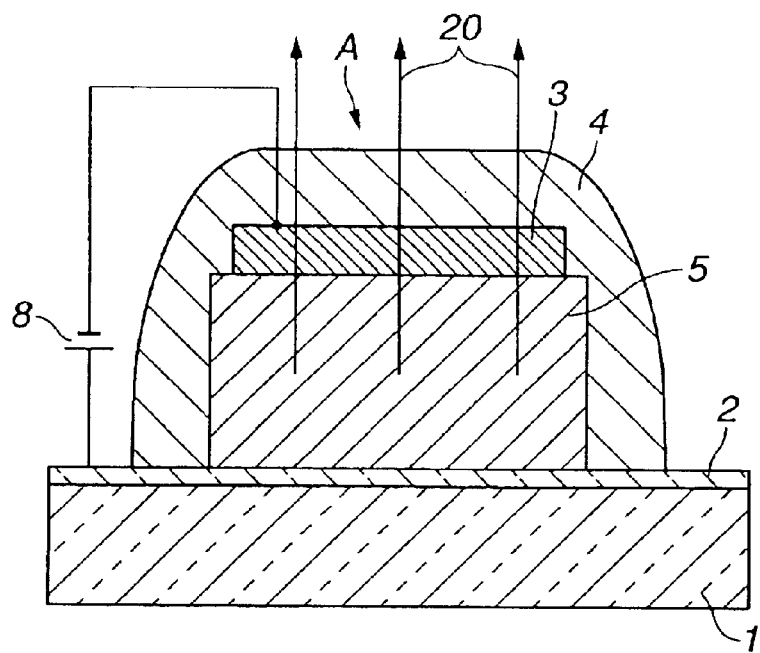
FIG. 10 is a schematic sectional view showing important parts of one organic electroluminescent element according to the present invention.
Figure 11:
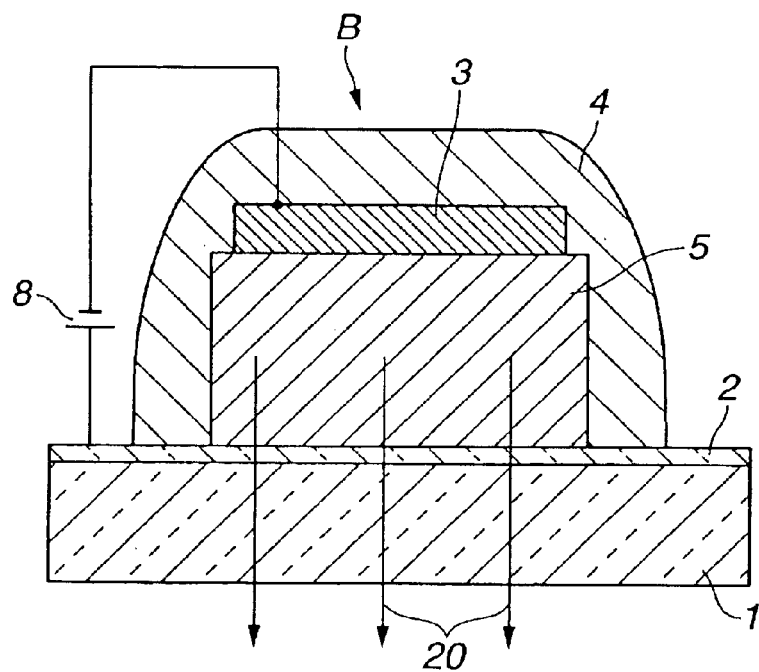
FIG. 11 is a schematic sectional view showing important parts of another organic electroluminescent element according to the present invention.
Figure 12:
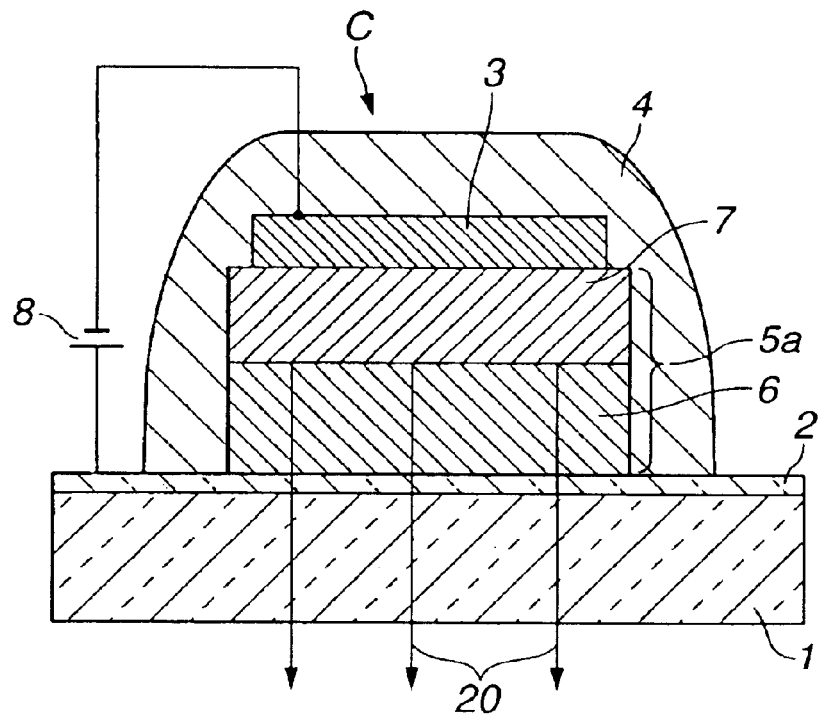
FIG. 12 is a schematic sectional view showing important parts of another organic electroluminescent element according to the present invention.
Figure 13:
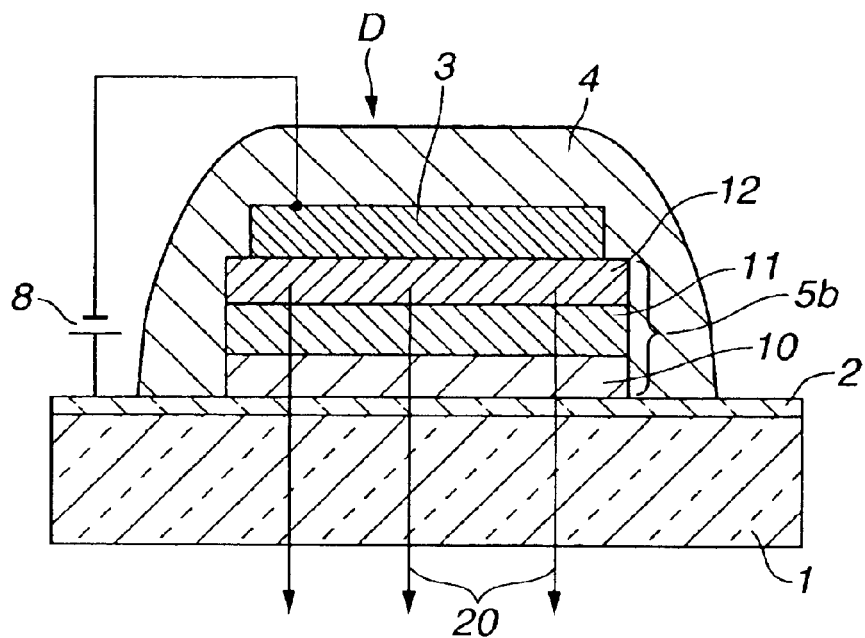
FIG. 13 is a schematic sectional view showing important parts of another organic electroluminescent element according to the present invention.
Figure 14:
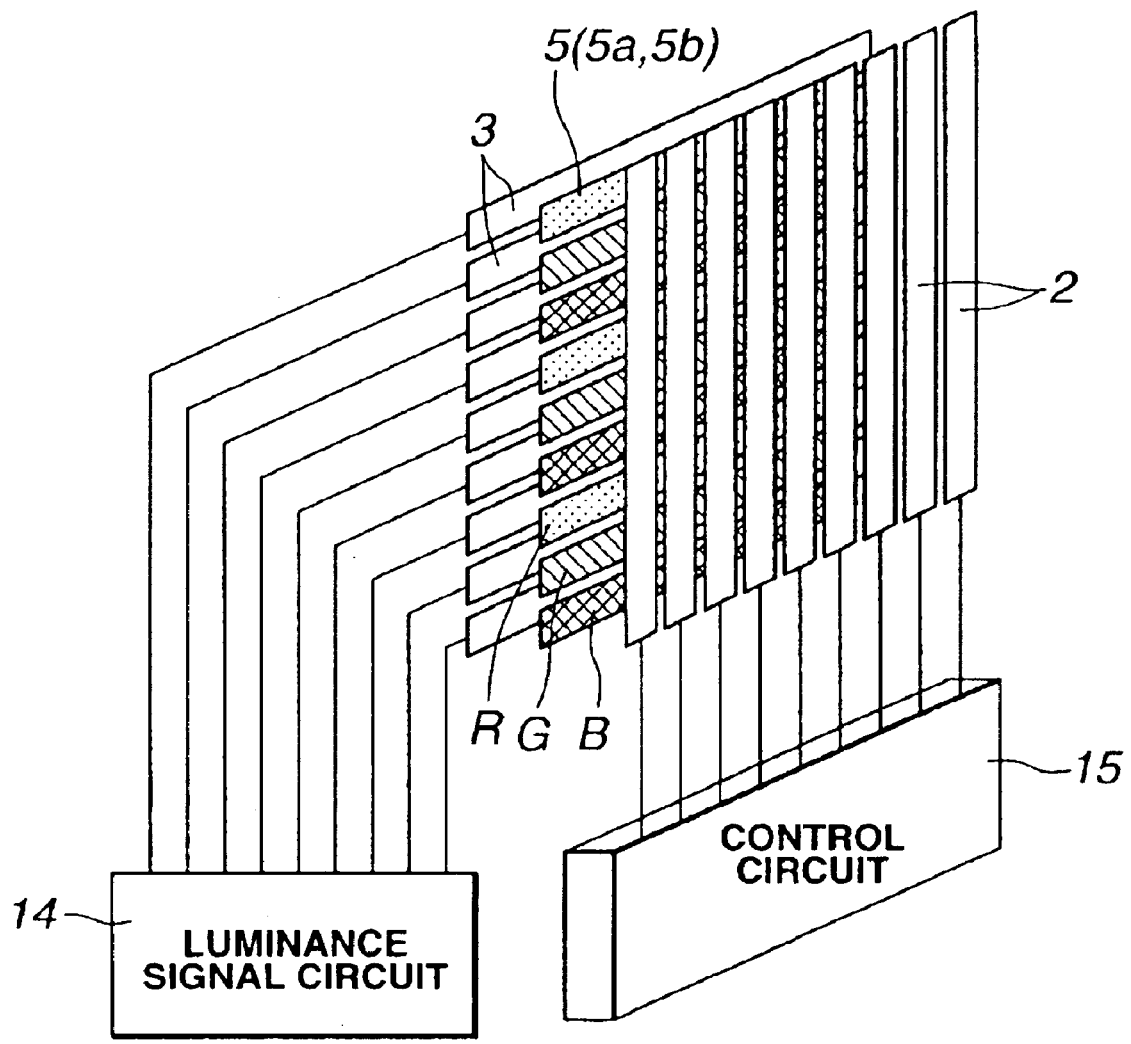
FIG. 14 is a diagram showing the structure of a full-color flat display composed of the organic electroluminescent elements according to the present invention.

The $^1$H-NMR spectrum is shown in FIG. 9.

Industrial Applicability

The compound of the present invention emits intense yellow to red light according to the substituent introduced into its structure. Therefore, it can be effectively used as an organic luminescent material. It has a high glass transition point and a high melting point. It is superior in heat resistance and also in electrical, thermal and chemical stability. It is amorphous and readily takes on a glassy state. It is sublimable and hence it forms a uniform amorphous film by vacuum deposition. It can be produced efficiently by ordinary process via the synthetic intermediate of the present invention.

What is claimed is:

1. An aminostyrylanthracene compound selected from the group consisting of:

General formula I having the formula:

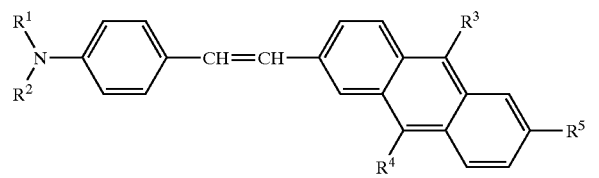

wherein $R^2$ is an unsubstituted aryl group; $R^3$ and $R^4$ are identical or different groups wherein at least one of $R^3$ and $R^4$ being selected from the group consisting of a hydrogen atom, a cyano group, a fluoroalkyl group, a nitro group, and a halogen atom; $R^5$ is selected from the group consisting of a hydrogen atom, a saturated or unsaturated hydrocarbon group having one or more carbons, or an aryl group which may have a substituent; and $R^1$ represents is an aryl group having a general formula 1:

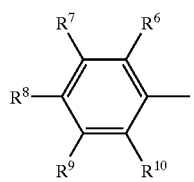

wherein $R^6$, $R^7$, $R^8$, $R^9$, and $R^{10}$ are identical or different groups separately selected from the group consisting of a hydrogen atom, a saturated or unsaturated hydrocarbon oxy group having one or more carbons, a hydrocarbon group, a hydrocarbon amino group, a fluoroalkyl group, and an aryl group which may have a substituent;

General formula II having the formula:

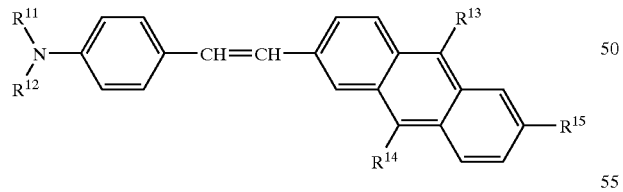

wherein $R^{13}$ and $R^{14}$ are identical or different groups wherein at least one of $R^{13}$ and $R^{14}$ being selected from the group consisting of a hydrogen atom, a cyano group, a fluoroalkyl group, a nitro group, and a halogen atom; $R^{15}$ is selected from the group consisting of a hydrogen atom, a saturated or unsaturated hydrocarbon group having one or more carbons, and an aryl group which may have a substituent; $R^{11}$ and $R^{12}$ are identical or different groups each representing an aryl group represented by the following general formula 2:

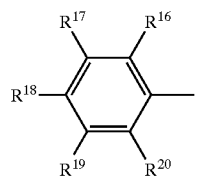

wherein $R^{16}$, $R^{17}$, $R^{18}$, $R^{19}$, and $R^{20}$ are identical or different groups separately selected from the group consisting of a hydrogen atom, a saturated or unsaturated hydrocarbon oxy group leaving one or more carbons, a hydrocarbon group, a hydrocarbon amino group, a fluoroalkyl group, and an aryl group which may have a substituent;

General formula III having the formula:

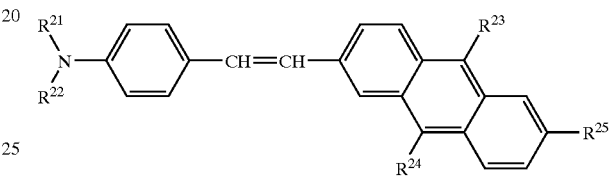

wherein $R^{23}$ and $R^{24}$ are identical or different groups wherein at least one of $R^{23}$ and $R^{24}$ is selected from the group consisting of a hydrogen atom, a cyano group, a fluoroalkyl group, a nitro group, and a halogen atom; $R^{25}$ is selected from the group consisting of a hydrogen atom, a saturated or unsaturated hydrocarbon group having one or more carbons, and an aryl group which may have a substituent; $R^{21}$ is an aryl group represented by the following general formula 3:

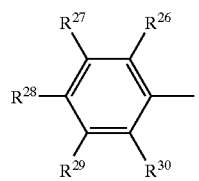

wherein $R^{26}$, $R^{27}$, $R^{28}$, $R^{29}$, and $R^{30}$ are identical or different groups separately selected from the group consisting of a hydrogen atom, a saturated or unsaturated hydrocarbon oxy group having one or more carbons, a hydrocarbon group, a hydrocarbon amino group, and a fluoroalkyl group; $R^{22}$ is an aryl group represented by the following general formula 4:

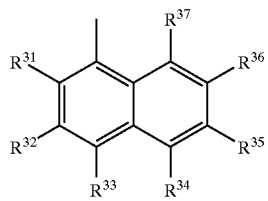

wherein $R^{31}$, $R^{32}$, $R^{33}$, $R^{34}$, $R^{35}$, $R^{36}$, and $R^{37}$ are identical or different groups separately selected from the group consisting of a hydrogen atom, a saturated or unsatur ated hydrocarbon oxy group having one or more carbons, a hydrocarbon group, a hydrocarbon amino group, and a fluoroalkyl group, and an aryl group which may have a substituent; and General formula IV having the formula:

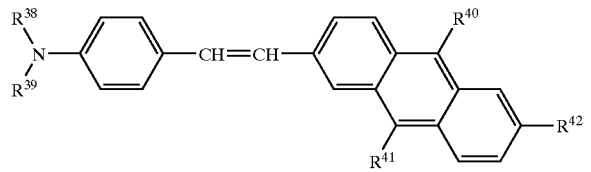

wherein $R^{38}$ and $R^{39}$ are identical or different groups wherein at least one of $R^{38}$ and $R^{39}$ is selected from the group consisting of a hydrogen atom, and a saturated or unsaturated hydrocarbon group having one or more carbons; $R^{40}$ and $R^{41}$ are identical or different groups separately selected from the group consisting of a hydrogen atom, a cyano group, a fluoroalkyl group, a nitro group, and a halogen atom; and $R^{42}$ is selected from the group consisting of a hydrogen atom, a saturated or unsaturated hydrocarbon group having one or more carbons, and an aryl group which may have a substituent.

2. An aminostyrylanthracene compound in according to claim 1 wherein said compound is represented by general formula 5 having the formula:

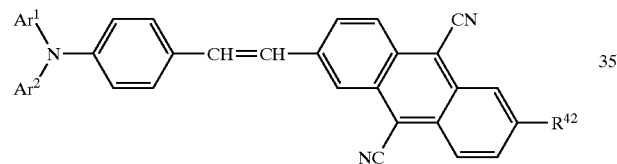

wherein $Ar^1$ and $Ar^2$ are identical or different aryl groups which may have a substituent selected from the group consisting of general formula 6, general formula 7, general formula 8, general formula 9, general formula 10, and general formula 11;

wherein general formula 6 has the formula:

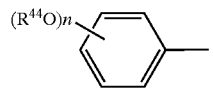

wherein general formula has the formula:

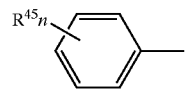

wherein general formula has the formula:

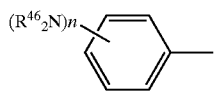

wherein general formula has the formula:

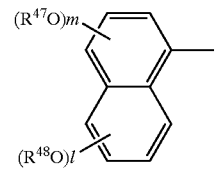

wherein general formula has the formula:

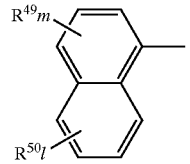

wherein general formula has the formula:

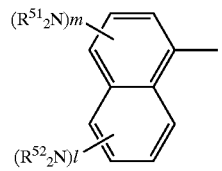

wherein $R^{44}$, $R^{45}$, and $R^{46}$ are separately selected from a group consisting of a saturated or unsaturated hydrocarbon group having one or more carbons, and a fluoroalkyl group; $R^{47}$, $R^{48}$, $R^{49}$, $R^{50}$, $R^{51}$, and $R^{52}$ are identical or different groups separately selected from a group consisting of a saturated or unsaturated hydrocarbon group having one or more carbons, and a fluoroalkyl group; n is an integer of 0 to 5; m is an integer of 0 to 3; l is an integer of 0 to 3; and $R^{43}$ is selected from the group consisting of a hydrogen atom, a saturated or unsaturated hydrocarbon group having one or more carbons, and an aryl group which may have a substituent.

3. An aminostyrylanthracene compound according to claim 2 wherein $R^{44}$, $R^{45}$, $R^{46}$, $R^{47}$, $R^{48}$, $R^{49}$, $R^{50}$, $R^{51}$, and $R^{52}$ each represent a group having 1 to 6 carbons.

4. An aminostyrylanthracene compound according to claim 2 wherein said compound is represented by a formula selected from the group consisting of general formula 12, general formula 13, general formula 14, general formula 15, general formula 16, general formula 17, and general formula 18;

wherein general formula 12 has the formula:

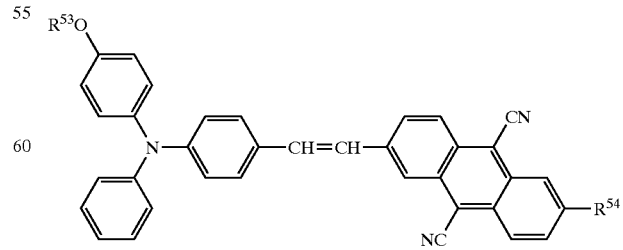

wherein $R^{53}$ is selected from the group consisting of a saturated or unsaturated hydrocarbon group having 1 to 6 carbons, and an aryl group which may have a substituent; $R^{54}$ is selected from the group consisting of a hydrogen atom, a saturated or unsaturated hydrocarbon group having 1 to 6 carbons, and an aryl group which may have a substituent;

wherein general formula 13 has the formula:

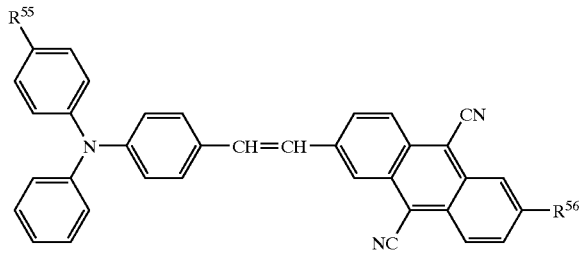

wherein $R^{55}$ is selected from the group consisting of a saturated or unsaturated hydrocarbon group having 1 to 6 carbons, a trifluoromethyl group, and an aryl group which may have a substituent; $R^{56}$ is selected from the group consisting of a hydrogen atom, a saturated or unsaturated hydrocarbon group having 1 to 6 carbons, and an aryl group which may have a substituent;

wherein general formula 14 has the formula:

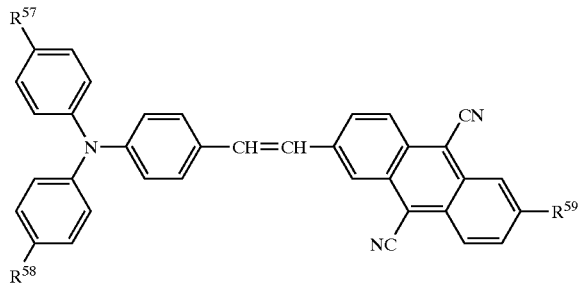

wherein $R^{57}$ and $R^{58}$ are separately selected from the group consisting of a saturated or unsaturated hydrocarbon group having 1 to 6 carbons, a trifluoromethyl group, and an aryl group which may have a substituent; $R^{59}$ is selected from the group consisting of a hydrogen atom, a saturated or unsaturated hydrocarbon group having 1 to 6 carbons, and an aryl group which may have a substituent;

wherein general formula 15 has the formula:

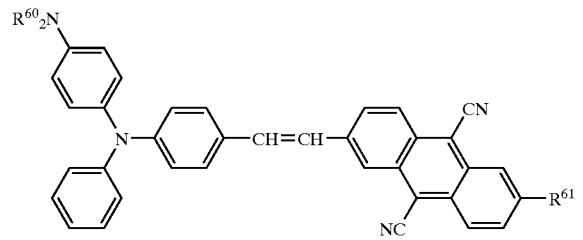

wherein $R^{60}$ is selected from the group consisting of a saturated or unsaturated hydrocarbon group having 1 to 6 carbons, and an aryl group which may have a substituent; $R^{61}$ is selected from the group consisting of a hydrogen atom, a saturated or unsaturated hydrocarbon group having 1 to 6 carbons, and an aryl group which may have a substituent;

wherein general formula 16 has the formula:

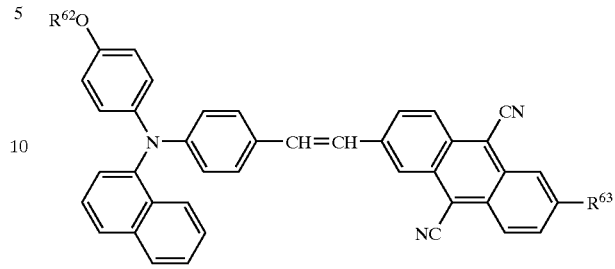

wherein $R^{62}$ is selected from the group consisting of a saturated or unsaturated hydrocarbon group having 1 to 6 carbons, and an aryl group which may have a substituent; $R^{63}$ is selected from the group consisting of a hydrogen atom, a saturated or unsaturated hydrocarbon group having 1 to 6 carbons, and an aryl group which may have a substituent;

wherein general formula 17 has the formula:

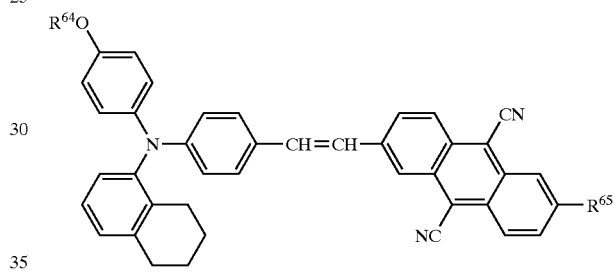

wherein $R^{64}$ is selected from the group consisting of a saturated or unsaturated hydrocarbon group having 1 to 6 carbons, and an aryl group which may have a substituent; $R^{65}$ is selected from the group consisting of a hydrogen atom, a saturated or unsaturated hydrocarbon group having 1 to 6 carbons, and an aryl group which may have a substituent;

wherein general formula 18 has the formula:

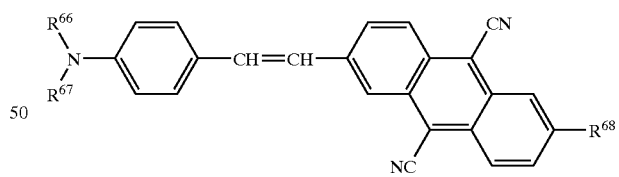

wherein $R^{66}$ and $R^{67}$ are separately selected from the group consisting of a saturated or unsaturated hydrocarbon group having 1 to 6 carbons, and an aryl group which may have a substituent; $R^{68}$ is selected from the group consisting of a hydrogen atom, a saturated or unsaturated hydrocarbon group having 1 to 6 carbons, and an aryl group which may have a substituent.

5. An aminostyrylanthracene compound according to claim 2 wherein said compound has a formula selected from the group consisting of structural formula 19-1, structural formula 19-2, structural formula 19-3, structural formula 19-4, structural formula 19-5, structural formula 19-6, structural formula 19-7, structural formula 19-8, structural formula 19-9, structural formula 19-10, structural formula 19-11, and structural formula 19-12;

wherein structural formula 19-1 has the formula:

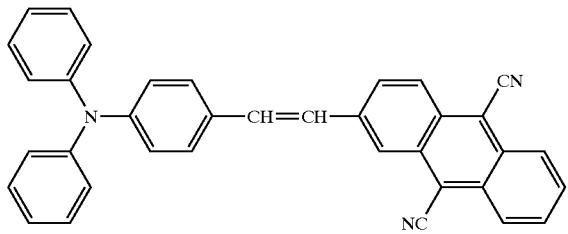

wherein structural formula 19-2 has the formula:

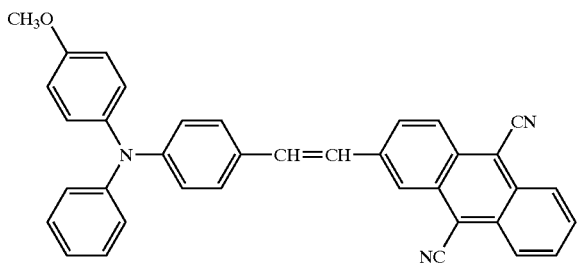

wherein structural formula 19-3 has the formula:

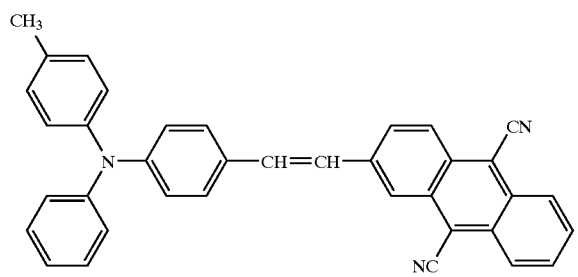

wherein structural formula 19-4 has the formula:

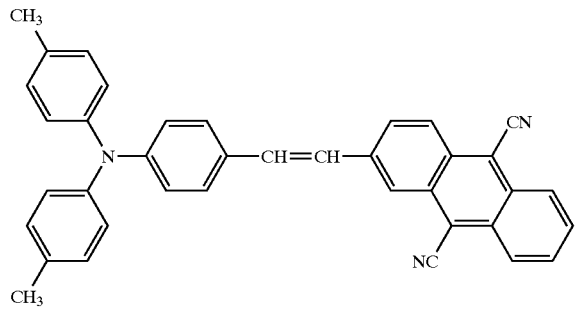

wherein structural formula 19-5 has the formula:

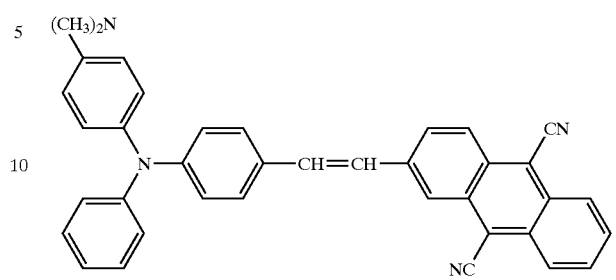

wherein structural formula 19-6 has the formula:

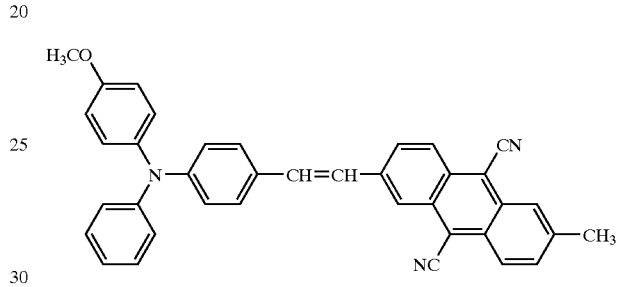

wherein structural formula 19-7 has the formula:

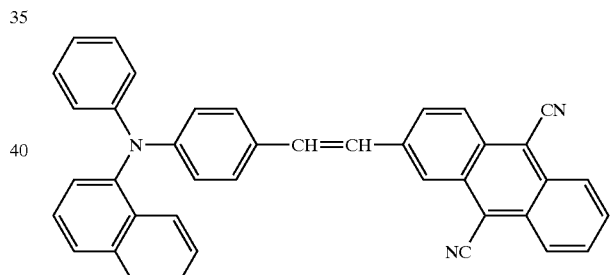

wherein structural formula 19-8 has the formula:

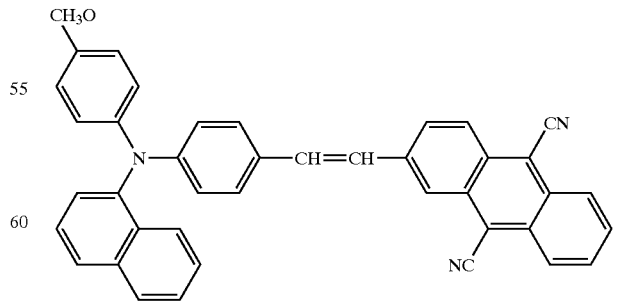

wherein structural formula 19-9 has the formula:

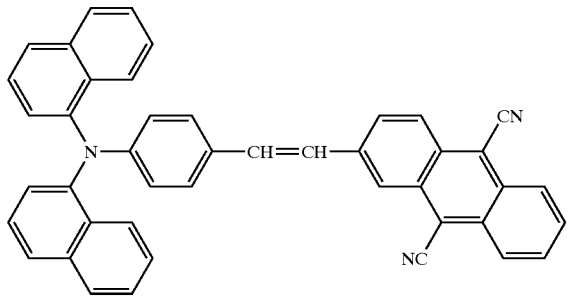

wherein structural formula 19-10 has the formula:

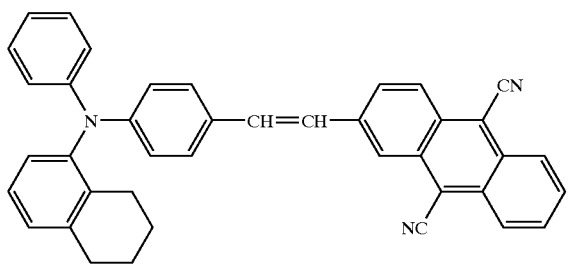

wherein structural formula 19-11 has the formula:

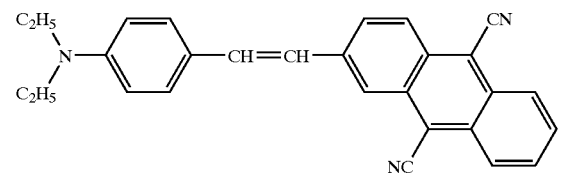

wherein structural formula 19-12 has the formula:

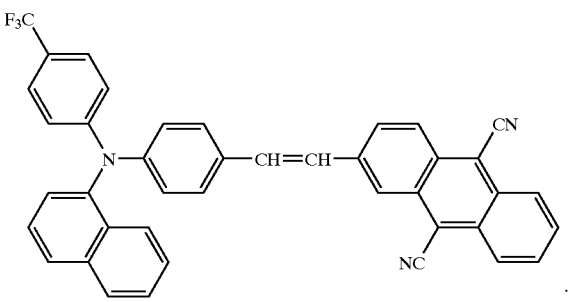

6. An aminostyrylanthracene compound according to claim 1 wherein said compound is represented by general formula 20 having the formula:

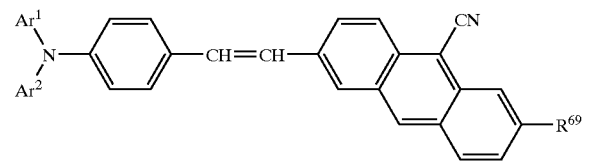

wherein $Ar^1$ and $Ar^2$ are identical or different aryl groups which may have a substituent wherein said substituent is selected from the group consisting of general formula 6, general formula 7, general formula 8, general formula 9, general formula 10 and general formula 11;

wherein general formula 6 has the formula:

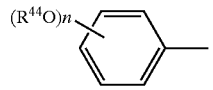

wherein general formula 7 has the formula:

wherein general formula 8 has the formula:

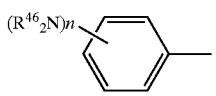

wherein general formula 9 has the formula:

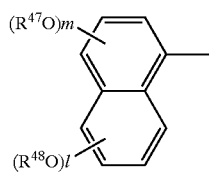

wherein general formula 10 has the formula:

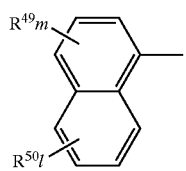

wherein general formula 11 has the formula:

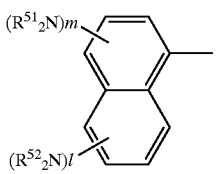

wherein $R^{44}$, $R^{45}$, and $R^{46}$ are separately selected from the group consisting of a saturated or unsaturated hydrocarbon groups having one or more carbons, and a fluoroalkyl group; $R^{47}$, $R^{48}$, $R^{49}$, $R^{50}$, $R^{51}$, and $R^{52}$ are identical or different groups separately selected from the group consisting of a saturated or unsaturated hydrocarbon group having one or more carbons, and a fluoroalkyl group; n is an integer of 0 to 5; m is an integer of 0 to 3; l is an integer of 0 to 3; and $R^{69}$ is selected from the group consisting of a hydrogen atom, a saturated or unsaturated hydrocarbon group, and an aryl group which may have a substituent.

7. An aminostyrylanthracene compound according to claim 6 wherein $R^{44}$, $R^{45}$, $R^{46}$, $R^{47}$, $R^{48}$, $R^{49}$, $R^{50}$, $R^{51}$, and $R^{52}$ each represent a group having 1 to 6 carbons.

8. An aminostyrylanthracene compound according to claim 6 wherein said compound is represented by a formula selected from the group consisting of general formula 21, general formula 22, general formula 23, general formula 24, general formula 25, general formula 26, and general formula 27;

wherein general formula 21 has the formula:

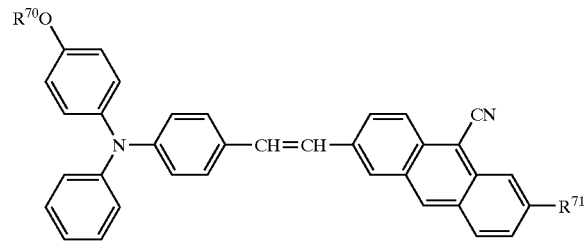

wherein $R^{70}$ is selected from the group consisting of a saturated or unsaturated hydrocarbon group having 1 to 6 carbons, and an aryl group which may have a substituent; $R^{71}$ is selected from the group consisting of a hydrogen atom, a saturated or unsaturated hydrocarbon group having 1 to 6 carbons, and an aryl group which may have a substituent;

wherein general formula 22 has the formula:

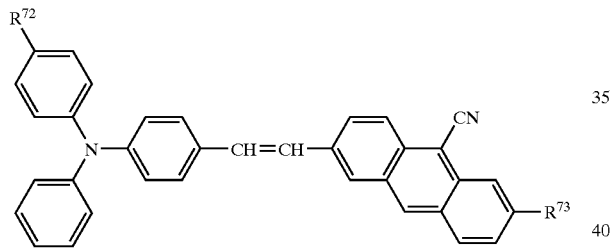

wherein $R^{72}$ is selected from the group consisting of a saturated or unsaturated hydrocarbon group having 1 to 6 carbons, a trifluoromethyl group, and an aryl group which may have a substituent; $R^{73}$ is selected from the group consisting of a hydrogen atom, a saturated or unsaturated hydrocarbon group having 1 to 6 carbons, and an aryl group which may have a substituent;

wherein general formula 23 has the formula:

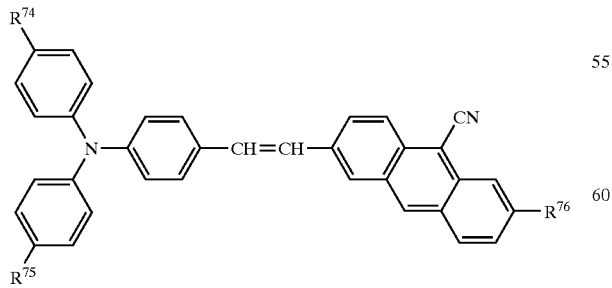

wherein $R^{74}$ and $R^{75}$ are separately selected from the group consisting a saturated or unsaturated hydrocarbon group having 1 to 6 carbons, a trifluoromethyl group, and an aryl group which may have a substituent; $R^{76}$ is selected from the group consisting of a hydrogen atom, a saturated or unsaturated hydrocarbon group having 1 to 6 carbons, and an aryl group which may have a substituent;

wherein general formula 24 has the formula:

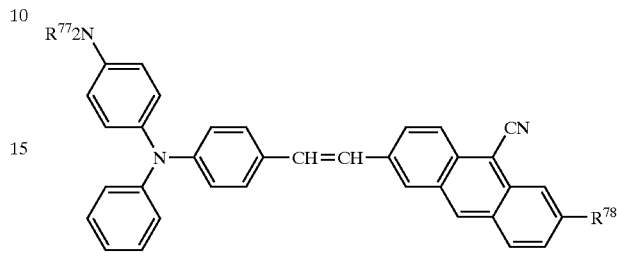

wherein $R^{77}$ is selected from the group consisting of a saturated or unsaturated hydrocarbon group having 1 to 6 carbons, and an aryl group which may have a substituent; $R^{78}$ is selected from the group consisting of a hydrogen atom, a saturated or unsaturated hydrocarbon group having 1 to 6 carbons, and an aryl group which may have a substituent;

wherein general formula 25 has the formula:

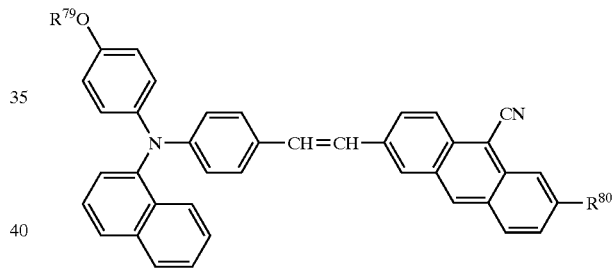

wherein $R^{79}$ is selected from the group consisting of a saturated or unsaturated hydrocarbon group having 1 to 6 carbons, and an aryl group which may have a substituent; $R^{80}$ is selected from the group consisting of a hydrogen atom, a saturated or unsaturated hydrocarbon group having 1 to 6 carbons, and an aryl group which may have a substituent;

wherein general formula 26 has the formula:

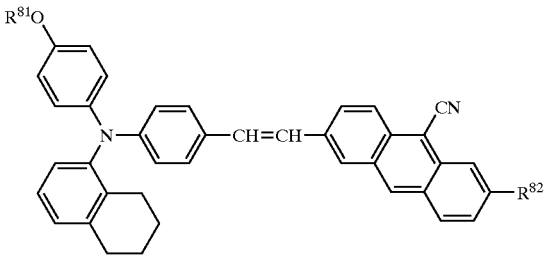

wherein R$^{81}$ is selected from the group consisting of a saturated or unsaturated hydrocarbon group having 1 to 6 carbons, and an aryl group which may have a substituent; R$^{82}$ is selected from the group consisting of a hydrogen atom, a saturated or unsaturated hydrocarbon group having 1 to 6 carbons, and an aryl group which may have a substituent;

wherein general formula 27 has the formula:

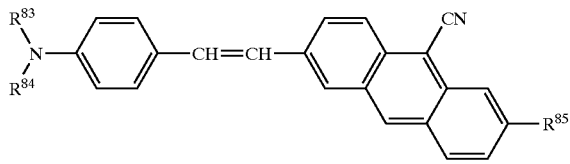

wherein R$^{83}$ and R$^{84}$ are separately selected from the group consisting of a saturated or unsaturated hydrocarbon group having 1 to 6 carbons, and an aryl group which may have a substituent; R$^{85}$ is selected from the group consisting of a hydrogen atom, a saturated or unsaturated hydrocarbon group having 1 to 6 carbons, and an aryl group which may have a substituent.

9. An aminostyrylanthracene compound according to claim 6 wherein said compound is represented by a formula selected from the group consisting of structural formula 28-1, structural formula 28-2, structural formula 28-3, structural formula 28-4, structural formula 28-5, structural formula 28-6, structural formula 28-7, structural formula 28-8, structural formula 28-9, structural formula 28-10, structural formula 28-11, and structural formula 28-12;

wherein structural formula 28-1 has the formula:

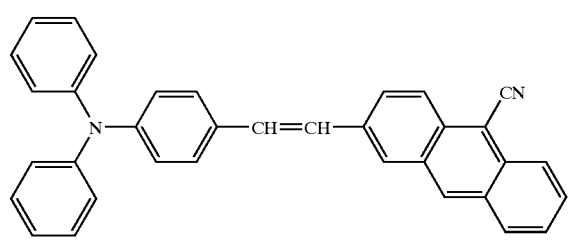

wherein structural formula 28-2 has the formula:

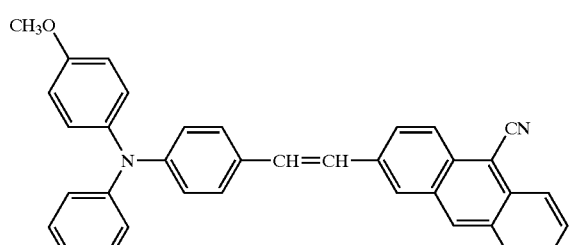

wherein structural formula 28-3 has the formula:

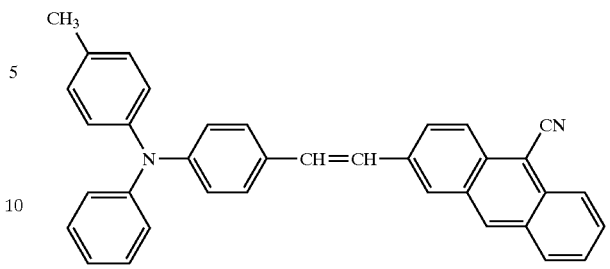

wherein structural formula 28-4 has the formula:

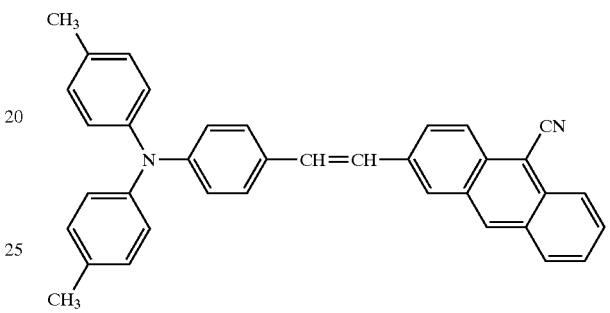

wherein structural formula 28-5 has the formula:

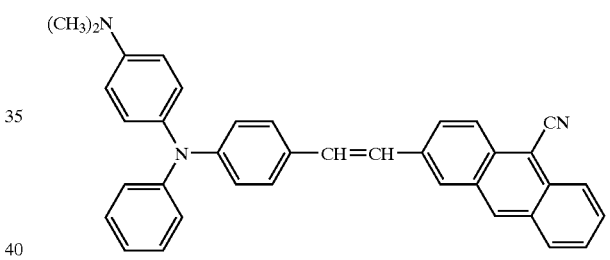

wherein structural formula 28-6 has the formula:

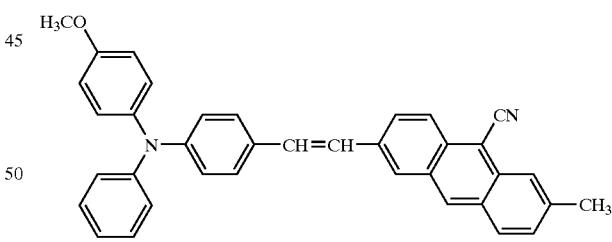

wherein structural formula 28-7 has the formula:

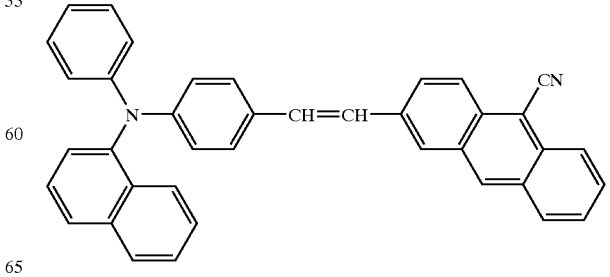

wherein structural formula 28-8 has the formula:

wherein structural formula 28-9 has the formula:

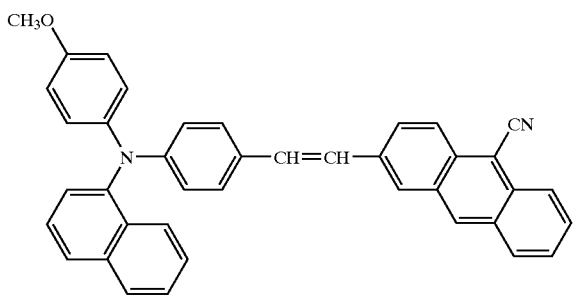

wherein structural formula 28-10 has the formula:

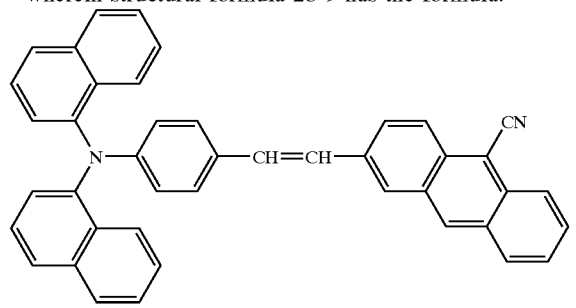

wherein structural formula 28-11 has the formula: and

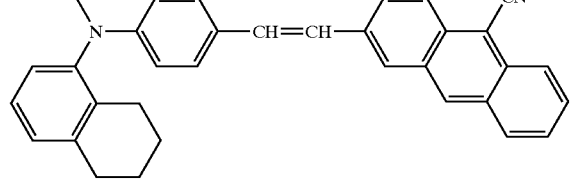

wherein structural formula 28-12 has the formula:

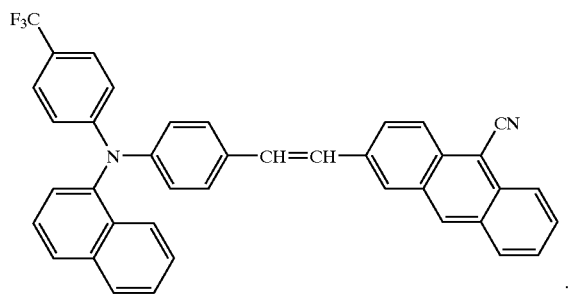

10. An aminostyrylanthracene compound according to claim 1 wherein said compound is represented by general formula 29 having the formula:

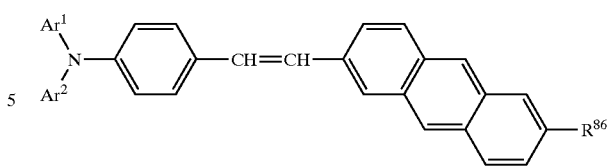

wherein $Ar^1$ and $Ar^2$ are identical or different aryl groups which may have a substituent wherein said substituent is selected from the group consisting of general formula 6, general formula 7, general formula 8, general formula 9, general formula 10, and general formula 11;

wherein general formula 6 has the formula:

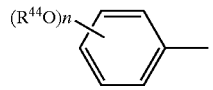

wherein general formula 7 has the formula:

wherein general formula 8 has the formula:

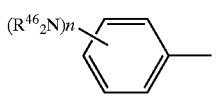

wherein general formula 9 has the formula:

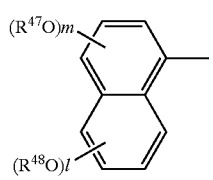

wherein general formula 10 has the formula:

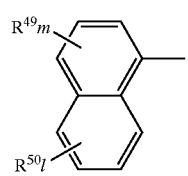

wherein general formula 11 has the formula:

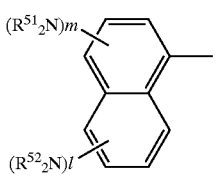

wherein $R^{44}$, $R^{45}$, and $R^{46}$ are separately selected from the group consisting of a saturated or unsaturated hydrocarbon groups having one or more carbons, and a fluoroalkyl group; $R^{47}$, $R^{48}$, $R^{49}$, $R^{50}$, $R^{51}$, and $R^{52}$ are identical or different groups separately selected from the group consisting of a saturated or unsaturated hydrocarbon group having one or more carbons, and a fluoroalkyl group; n is an integer of 0 to 5; m is an integer of 0 to 3; 1 is an integer of 0 to 3; and $R^{86}$ is selected from the group consisting of a hydrogen atom, a saturated or unsaturated hydrocarbon group, and an aryl group which may have a substituent.

11. An aminostyrylanthracene compound according to claim 10 wherein $R^{44}$, $R^{45}$, $R^{46}$, $R^{47}$, $R^{48}$, $R^{49}$, $R^{50}$, $R^{51}$, and $R^{52}$ each represent a group having 1 to 6 carbons.

12. An aminostyrylanthracene compound according to claim 10 wherein said compound is represented by a formula selected from the group consisting of general formula 30, general formula 31, general formula 32, general formula 33, general formula 34, general formula 35, and general formula 36;

wherein general formula 30 has the formula:

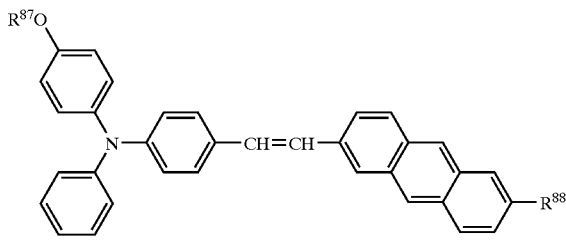

wherein $R^{87}$ is selected from the group consisting of a saturated or unsaturated hydrocarbon group having 1 to 6 carbons, and an aryl group which may have a substituent; $R^{88}$ is selected from the group consisting of a hydrogen atom, a saturated or unsaturated hydrocarbon group having 1 to 6 carbons, and an aryl group which may have a substituent;

wherein general formula 31 has the formula:

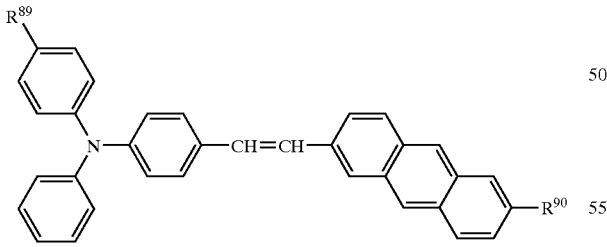

wherein $R^{89}$ is selected from the group consisting of a saturated or unsaturated hydrocarbon group having 1 to 6 carbons, a trifluoromethyle group, and an aryl group which may have a substituent; $R^{90}$ is selected from the group consisting of a hydrogen atom, a saturated or unsaturated hydrocarbon group having 1 to 6 carbons, and an aryl group which may have a substituent;

wherein general formula 32 has the formula:

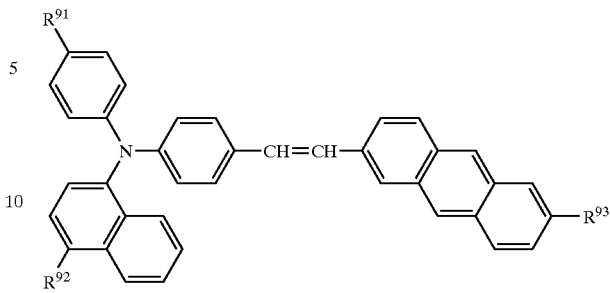

wherein $R^{91}$ and $R^{92}$ are separately selected from the group consisting of a saturated or unsaturated hydrocarbon group having 1 to 6 carbons, a trifluoromethyl group, and an aryl group which may have a substituent; $R^{93}$ is selected from the group consisting of a hydrogen atom, a saturated or unsaturated hydrocarbon group having 1 to 6 carbons, and an aryl group which may have a substituent;

wherein general formula 33 has the formula:

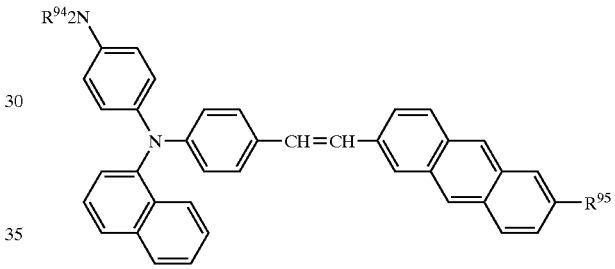

wherein $R^{94}$ is selected from the group consisting of a saturated or unsaturated hydrocarbon group having 1 to 6 carbons, and an aryl group which may have a substituent; $R^{95}$ is selected from the group consisting of a hydrogen atom, a saturated or unsaturated hydrocarbon group having 1 to 6 carbons, and an aryl group which may have a substituent;

wherein general formula 34 has the formula:

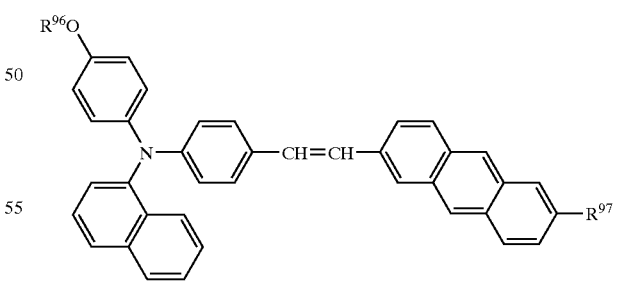

wherein $R^{96}$ is selected from the group consisting of a saturated or unsaturated hydrocarbon group having 1 to 6 carbons, and an aryl group which may have a substituent; $R^{97}$ is selected from the group consisting of a hydrogen atom, a saturated or unsaturated hydrocarbon group having 1 to 6 carbons, and an aryl group which may have a substituent;

wherein general formula 35 has the formula:

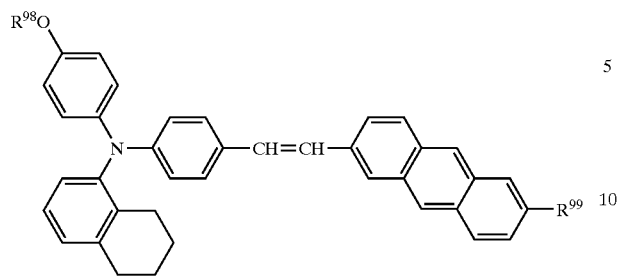

wherein $R^{98}$ is selected from the group consisting of a saturated or unsaturated hydrocarbon group having 1 to 6 carbons, and an aryl group which may have a substituent; $R^{99}$ is selected from the group consisting of a hydrogen atom, a saturated or unsaturated hydrocarbon group having 1 to 6 carbons, and an aryl group which may have a substituent;

wherein general formula 36 has the formula:

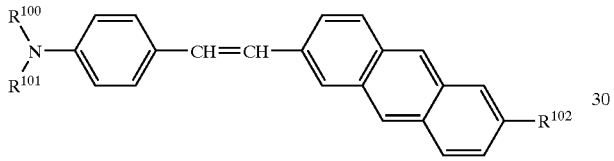

wherein $R^{100}$ and $R^{101}$ are separately selected from the group consisting of a saturated or unsaturated hydrocarbon group having 1 to 6 carbons, and an aryl group which may have a substituent; $R^{102}$ is selected from the group consisting of a hydrogen atom, a saturated or unsaturated hydrocarbon group having 1 to 6 carbons, and an aryl group which may have a substituent.

13. An aminostyrylanthracene compound according to claim 10 wherein said compound is represented by a formula selected from the group consisting of structural formula 37-1, structural formula 37-2, structural formula 37-3, structural formula 37-4, structural formula 37-5, structural formula 37-6, structural formula 37-7, structural formula 37-8, structural formula 37-9, structural formula 37-10, structural formula 37-11, and structural formula 37-12;

wherein structural formula 37-1 has the formula:

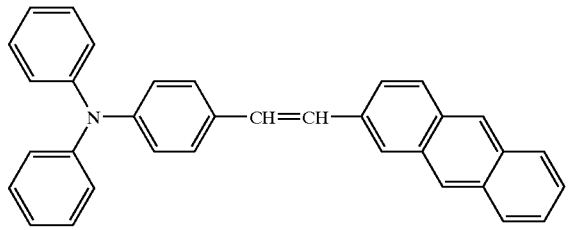

wherein structural formula 37-2 has the formula:

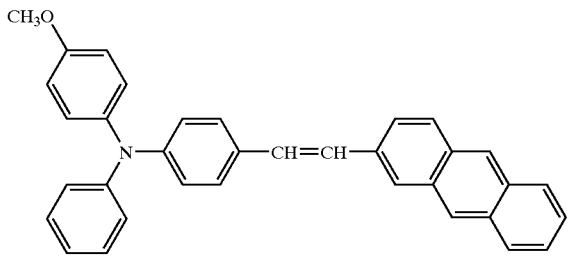

wherein structural formula 37-3 has the formula:

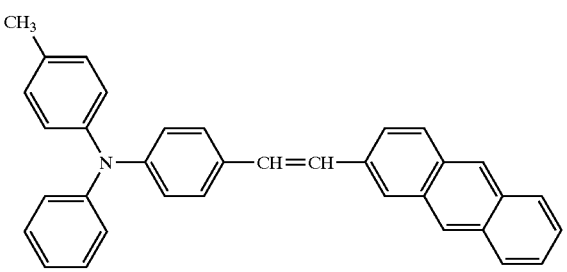

wherein structural formula 37-4 has the formula:

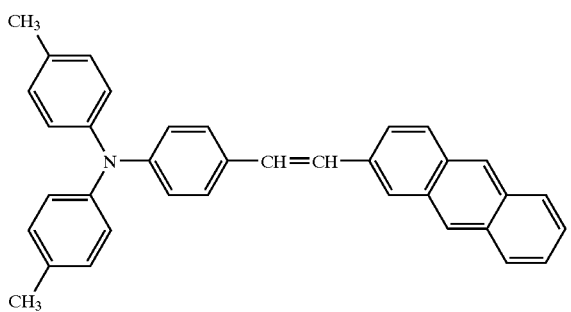

wherein structural formula 37-5 has the formula:

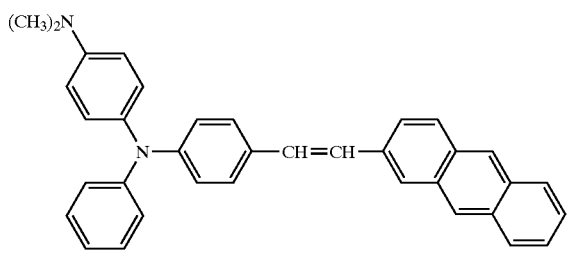

wherein structural formula 37-6 has the formula:

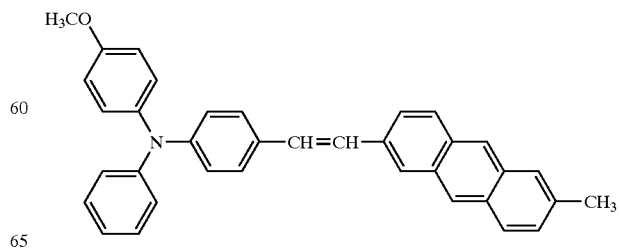

wherein structural formula 37-7 has the formula:

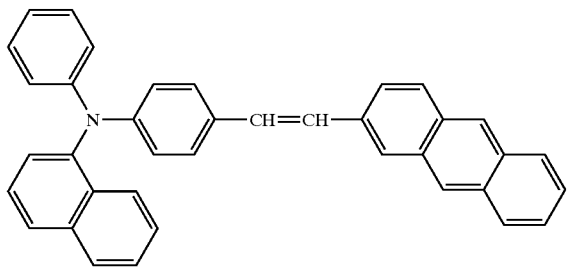

wherein structural formula 37-8 has the formula:

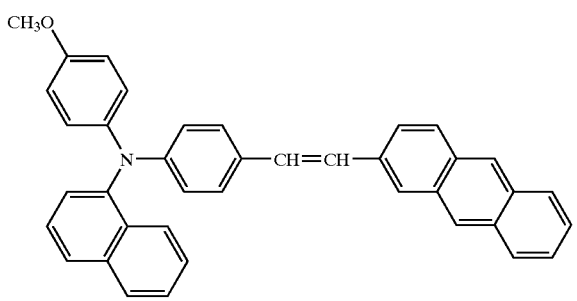

wherein structural formula 37-9 has the formula:

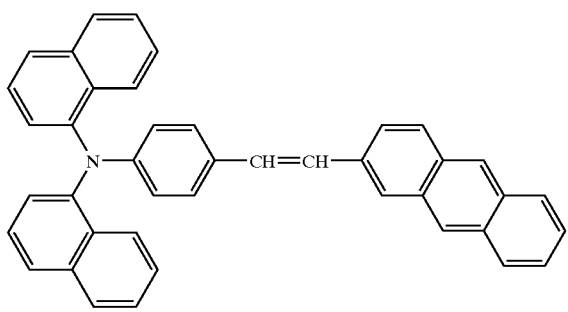

wherein structural formula 37-10 has the formula:

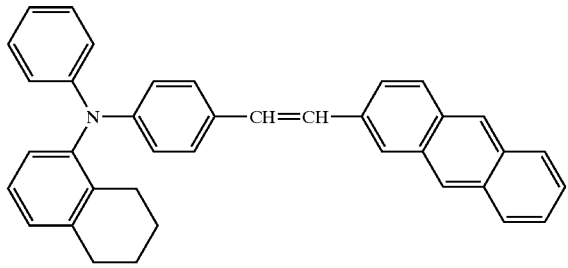

wherein structural formula 37-11 has the formula: and

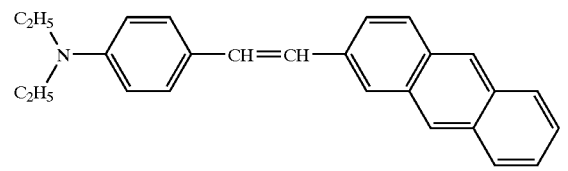

wherein structural formula 37-12 has the formula:

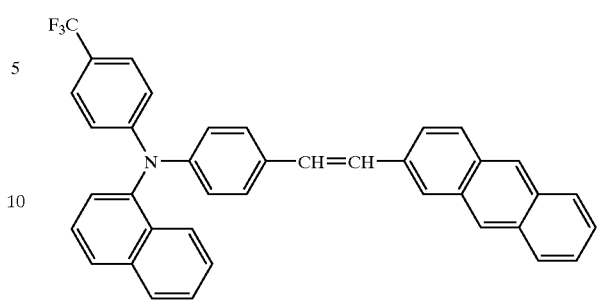

14. A process for producing an aminostyrylanthracene compound which comprises the following steps:

condensing in aminobenzaldehyde having a general formula V:

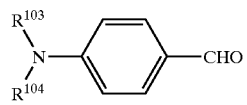

wherein $R^{103}$ and $R^{104}$ are separately selected from the group consisting of $R^1$, $R^2$, $R^{11}$, $R^{12}$, $R^{21}$, $R^{22}$, $R^{38}$, and $R^{39}$, with a phosphonic ester having a general formula VI:

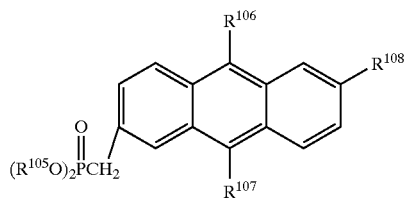

or a phosphonium salt having a general formula VII:

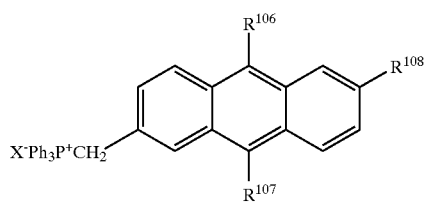

wherein $R^{105}$ is a hydrocarbon group; $R^{106}$ and $R^{107}$ are separately selected from the group consisting of $R^3$, $R^4$, $R^{13}$, $R^{14}$, $R^{23}$, $R^{24}$, $R^{40}$, or $R^{41}$; $R^{108}$ is selected from the group consisting of $R^5$, $R^{16}$, $R^{25}$, and $R^{42}$; and X is a halogen atom;

thereby forming an aminostyrylanthracene compound represented by a formula selected from the group consisting of general formula I, general formula II, general formula III, and general formula IV;

wherein general formula I has the formula:

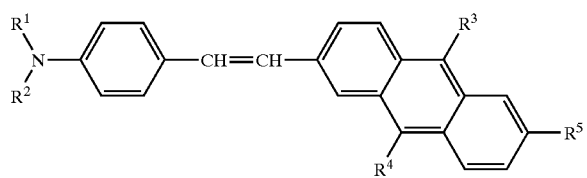

wherein $R^2$ is an unsubstituted aryl group; $R^3$ and $R^4$ are identical or different groups wherein at least one of $R^3$ and $R^4$ is selected from the group consisting of a hydrogen atom, a cyano group, a fluoroalkyl group, a nitro group, or a halogen atom; $R^5$ is selected from the group consisting of a hydrogen atom, a saturated or unsaturated hydrocarbon group having one or more carbons, and an aryl group which may have a substituent; and $R^1$ is an aryl group having general formula 1:

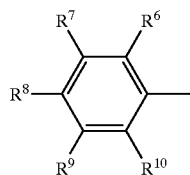

wherein $R^6$, $R^7$, $R^8$, $R^9$, and $R^{10}$ are identical or different groups separately selected from the group consisting of a hydrogen atom, a saturated or unsaturated hydrocarbon oxy group having one or more carbons, a hydrocarbon group, a hydrocarbon amino group, a fluoroalkyl group, and an aryl group which may have a substituent;

wherein general formula II has the formula:

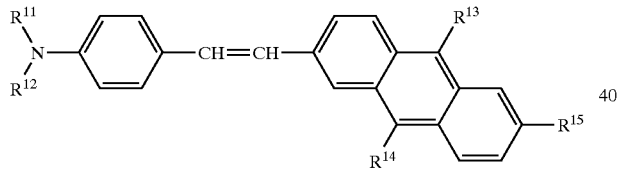

wherein $R^{13}$ and $R^{14}$ are identical or different groups wherein at least one of $R^{13}$ and $R^{14}$ being selected from the group consisting of hydrogen atom, a cyano group, a fluoroalkyl group, a nitro group, and a halogen atom; $R^{15}$ is selected from the group consisting of a hydrogen atom, a saturated or unsaturated hydrocarbon group having one or more carbons, and an aryl group which may have a substituent; $R^{11}$ and $R^{12}$ are identical or different groups wherein each is an aryl group having general formula 2:

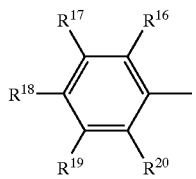

wherein $R^{16}$, $R^{17}$, $R^{18}$, $R^{19}$, and $R^{20}$ are identical or different groups separately selected from the group consisting of a hydrogen atom, a saturated or unsaturated hydrocarbon oxy group having one or more carbons, a hydrocarbon group, a hydrocarbon amino group, a fluoroalkyl group, and an aryl group which may have a substituent;

wherein general formula III has the formula:

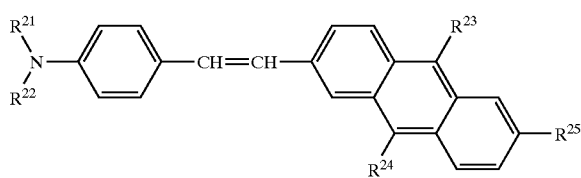

wherein $R^{23}$ and $R^{24}$ are identical or different groups wherein at least one of $R^{23}$ and $R^{24}$ being selected from the group consisting of hydrogen atom, a cyano group, a fluoroalkyl group, a nitro group, and a halogen atom; $R^{25}$ is selected from the group consisting of a hydrogen atom, a saturated or unsaturated hydrocarbon group having on or more carbons, and an aryl group which may have a substituent; $R^{21}$ is an aryl group having general formula 3:

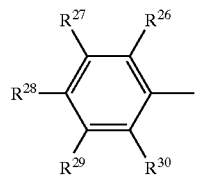

wherein $R^{26}$, $R^{27}$, $R^{28}$, $R^{29}$, and $R^{30}$ are identical or different groups separately selected from the group consisting of a hydrogen atom, a saturated or unsaturated hydrocarbon oxy group having one or more carbons, a hydrocarbon group, a hydrocarbon amino group, a fluoroalkyl group; and $R^{22}$ is an aryl group having a general formula 4:

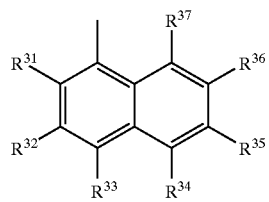

wherein $R^{31}$, $R^{32}$, $R^{33}$, $R^{34}$, $R^{35}$, $R^{36}$, and $R^{37}$ are identical or different groups separately selected from the group consisting of a hydrogen atom, a saturated or unsaturated hydrocarbon oxy group having one or more carbons, a hydrocarbon group, a hydrocarbon amino group, a fluoroalkyl group, and an aryl group which may have a substituent; and

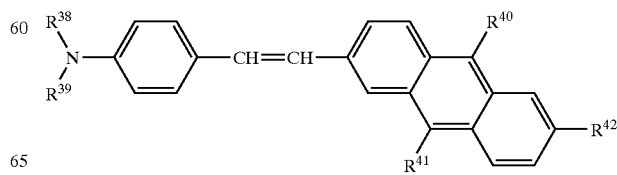

wherein $R^{38}$ and $R^{39}$ are identical or different groups wherein at least one of $R^{38}$ and $R^{39}$ is selected from the group consisting of a hydrogen atom, and a saturated or unsaturated hydrocarbon group having one or more carbons; $R^{40}$ and $R^{41}$ are identical or different groups separately selected from the group consisting of a hydrogen atom, a cyano group, a fluoroalkyl group, a nitro group, and a halogen atom; and $R^{42}$ is selected from the group consisting of a hydrogen atom, a saturated or unsaturated hydrocarbon group having one or more carbons, and an aryl group which may have a substituent.

15. A process for producing an aminostyrylanthracene compound according to claim 14 wherein said process further comprises the steps of:

performing said condensation by Wittig-Horner reaction or Wittig reaction;

treating said phosphonic ester or, in the alternative, said phosphonium salt with a base in a solvent thereby producing carboanions; and condensing said carboanions with said aminobenzaldehyde.

16. A process for producing an aminostyrylanthracene compound to claim 14 wherein said aminostyrylanthracene compound is represented by a general formula 5 having the formula:

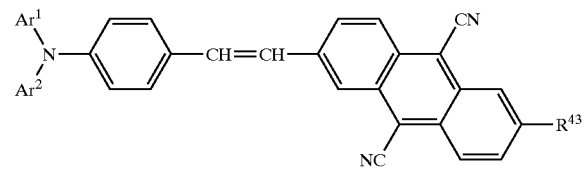

wherein $Ar^1$ and $Ar^2$ are identical or different aryl groups which may have a substituent selected from the group consisting of general formula 6, general formula 7, general formula 8, general formula 9, general formula 10, and general formula 11;

wherein general formula 6 has the formula:

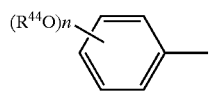

wherein general formula has the formula:

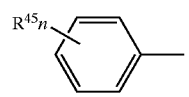

wherein general formula has the formula:

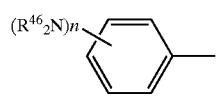

wherein general formula has the formula:

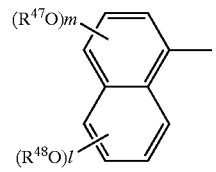

wherein general formula has the formula:

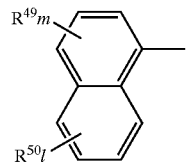

wherein general formula has the formula:

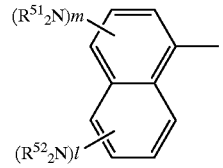

wherein $R^{44}$, $R^{45}$, and $R^{46}$ are separately selected from the group consisting of a saturated or unsaturated hydrocarbon groups having one or more carbons, and a fluoroalkyl group; $R^{47}$, $R^{48}$, $R^{49}$, $R^{50}$, $R^{51}$, and $R^{52}$ are identical or different groups separately selected from a group consisting of a saturated or unsaturated hydrocarbon group having one or more carbons, and a fluoroalkyl group; n is an integer of 0 to 5; m is an integer of 0 to 3; l is an integer of 0 to 3; and $R^{43}$ is selected from the group consisting of a hydrogen atom, a saturated or unsaturated hydrocarbon group having one or more carbons, and an aryl group which may have a substituent;

wherein said compound is obtained by condensing a 4-(N,N-diarylamino)benzaldehyde having a general formula 38:

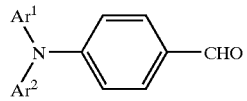

with a phosphonic ester having a general formula 39:

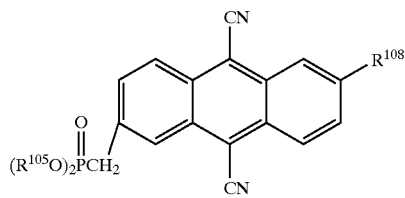

or, in the alternative, a phosphonium salt having a general formula 40:

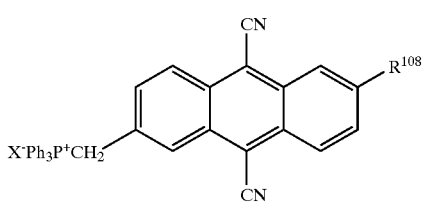

wherein Ar¹, Ar², $R^{105}$, and X are defined as above.

17. A process for producing an aminostyrylanthracene compound according to claim 14 wherein $R^{105}$ is a saturated hydrocarbon group having 1 to 4 carbons.

18. A process for producing an aminostyrylanthracene compound according to claim 16 wherein $R^{44}$, $R^{45}$, $R^{46}$, $R^{47}$, $R^{48}$, $R^{49}$, $R^{50}$, $R^{51}$, and $R^{52}$ are groups having 1 to 6 carbons.

19. A process for producing an aminostyrylanthracene compound according to claim 16 wherein said process gives an aminostyrylanthracene compound having a formula selected from the group consisting of general formula 12, general formula 13, general formula 14, general formula 15, general formula 16, general formula 17, and general formula 18;

wherein general formula 12 has the formula:

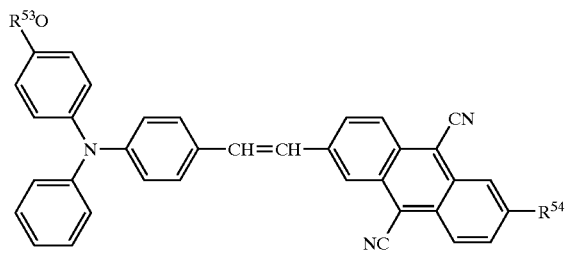

wherein, $R^{53}$ is selected from the group consisting of a saturated or unsaturated hydrocarbon group having 1 to 6 carbons, and an aryl group which may have a substituent; $R^{54}$ is selected from the group consisting of a hydrogen atom, a saturated or unsaturated hydrocarbon group having 1 to 6 carbons, and an aryl group which may have a substituent;

wherein general formula 13 has the formula:

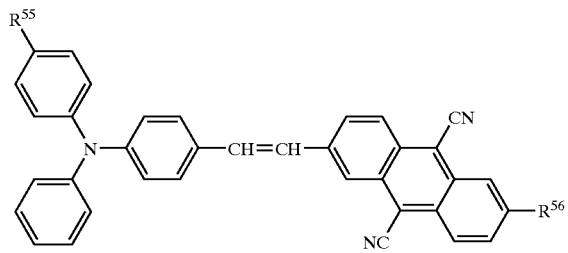

wherein $R^{55}$ is selected from the group consisting of a saturated or unsaturated hydrocarbon group having 1 to 6 carbons, a trifluoromethyl group, and an aryl group which may have a substituent; $R^{56}$ is selected from the group consisting of a hydrogen atom, a saturated or unsaturated hydrocarbon group having 1 to 6 carbons, and an aryl group which may have a substituent;

wherein general formula 14 has the formula:

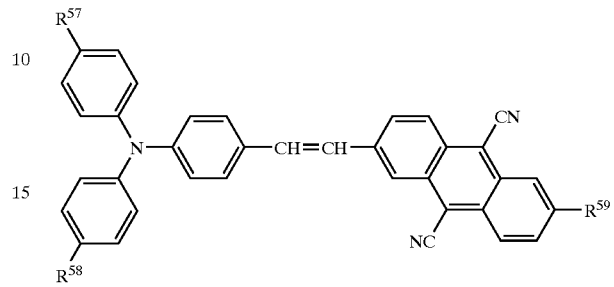

wherein $R^{57}$ and $R^{58}$ are separately selected from the group consisting of a saturated or unsaturated hydrocarbon group having 1 to 6 carbons, a trifluoromethyl group, and an aryl group which may have a substituent; $R^{59}$ is selected from the group consisting of a hydrogen atom, a saturated or unsaturated hydrocarbon group having 1 to 6 carbons, and an aryl group which may have a substituent;

wherein general formula 15 has the formula:

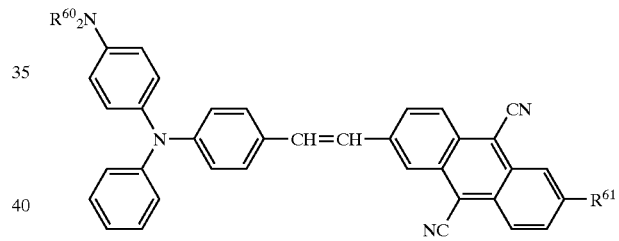

wherein $R^{60}$ is selected from the group consisting of a saturated or unsaturated hydrocarbon group having 1 to 6 carbons, and an aryl group which may have a substituent; $R^{61}$ is selected from the group consisting of a hydrogen atom, a saturated or unsaturated hydrocarbon group having 1 to 6 carbons, and an aryl group which may have a substituent;

wherein general formula 16 has the formula:

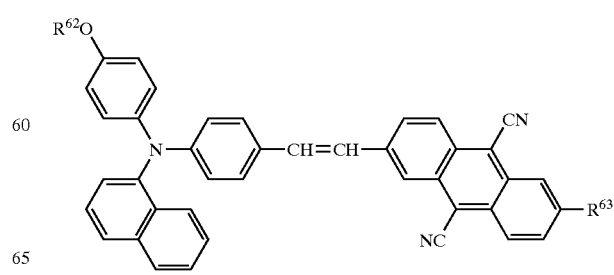

wherein $R^{62}$ is selected from the group consisting of a saturated or unsaturated hydrocarbon group having 1 to 6 carbons, and an aryl group which may have a substituent; $R^{63}$ is selected from the group consisting of a hydrogen atom, a saturated or unsaturated hydrocarbon group having 1 to 6 carbons, and an aryl group which may have a substituent;

wherein general formula 17 has the formula:

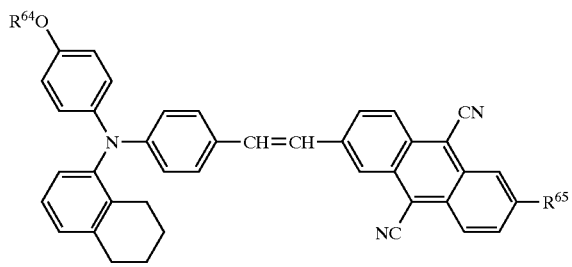

wherein $R^{64}$ is selected from the group consisting of a saturated or unsaturated hydrocarbon group having 1 to 6 carbons, and an aryl group which may have a substituent; $R^{65}$ is selected from the group consisting of a hydrogen atom, a saturated or unsaturated hydrocarbon group having 1 to 6 carbons, and an aryl group which may have a substituent;

wherein general formula 18 has the formula:

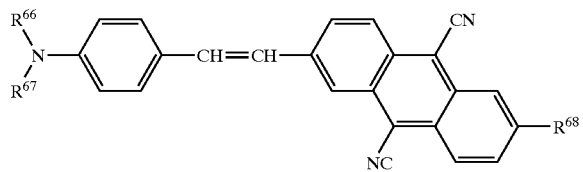

wherein $R^{66}$ and $R^{67}$ are separately selected from the group consisting of a saturated or unsaturated hydrocarbon group having 1 to 6 carbons, and an aryl group which may have a substituent; $R^{68}$ is selected from the group consisting of a hydrogen atom, a saturated or unsaturated hydrocarbon group having 1 to 6 carbons, and an aryl group which may have a substituent.

20. A process for producing an aminostyrylanthracene compound according to claim 16 wherein said process gives an aminostyrylanthracene compound wherein said compound has a formula selected from the group consisting of structural formula 19-1, structural formula 19-2, structural formula 19-3, structural formula 19-4, structural formula 19-5, structural formula 19-6, structural formula 19-7, structural formula 19-8, structural formula 19-9, structural formula 19-10, structural formula 19-11, and structural formula 19-12;

wherein structural formula 19-1 has the formula:

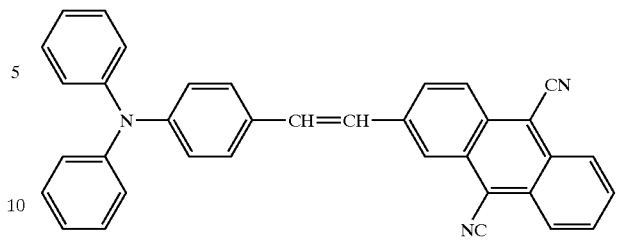

wherein structural formula 19-2 has the formula:

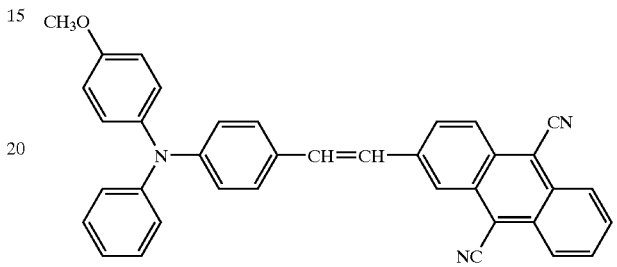

wherein structural formula 19-3 has the formula:

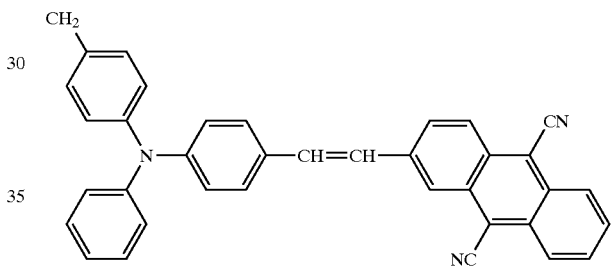

wherein structural formula 19-4 has the formula:

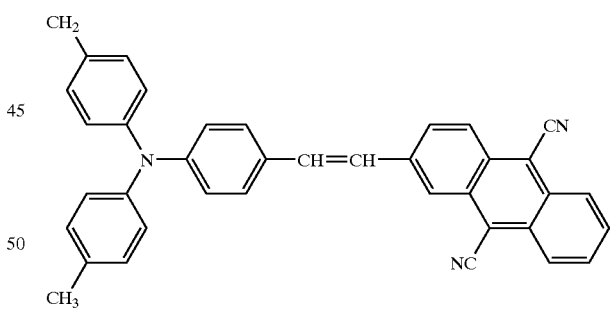

wherein structural formula 19-5 has the formula:

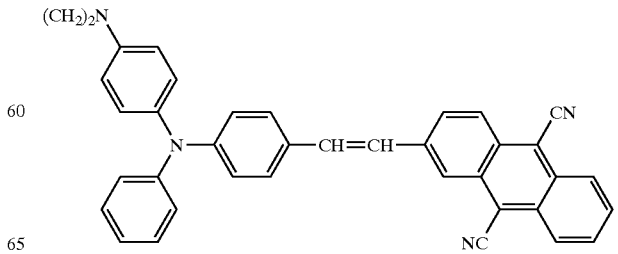

wherein structural formula 19-6 has the formula:

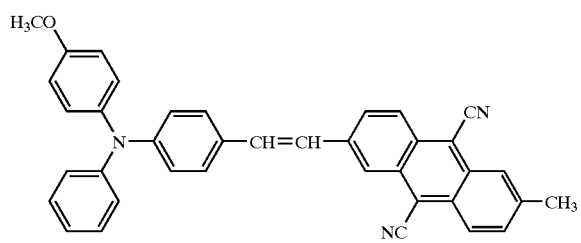

wherein structural formula 19-7 has the formula:

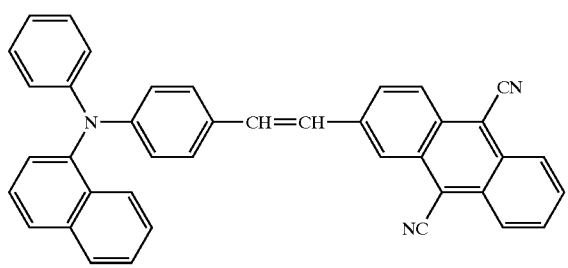

wherein structural formula 19-8 has the formula:

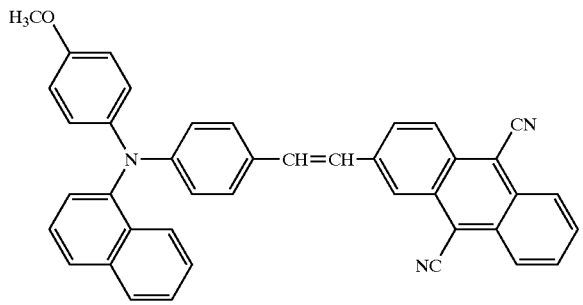

wherein structural formula 19-9 has the formula:

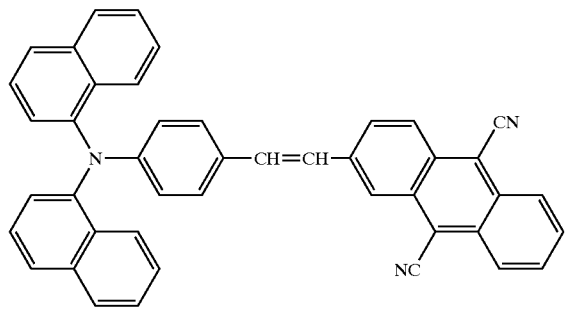

wherein structural formula 19-10 has the formula:

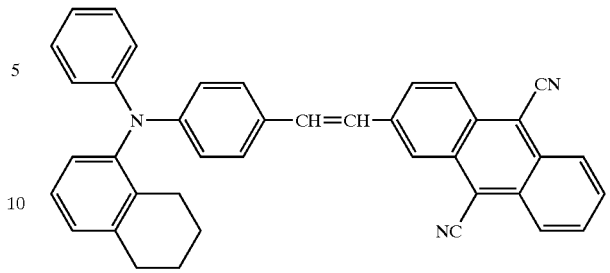

wherein structural formula 19-11 has the formula:

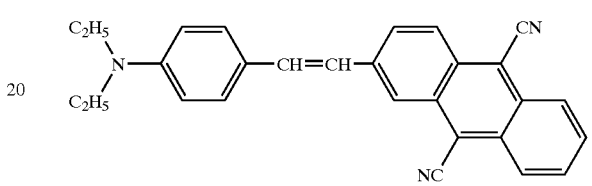

wherein structural formula 19-12 has the formula:

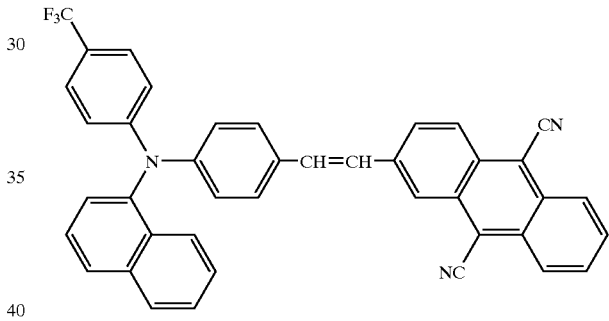

21. A process for producing an aminostyrylanthracene compound according to claim 14 wherein said compound is represented by general formula 20 having the formula:

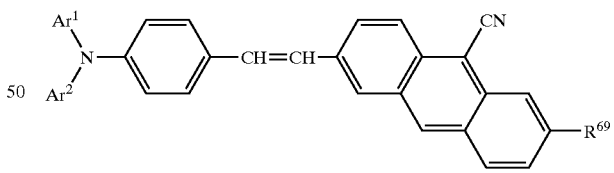

wherein $Ar^1$ and $Ar^2$ are identical or different aryl groups which may have a substituent wherein said substituent is selected from the group consisting of general formula 6, general formula 7, general formula 8, general formula 9, general formula 10, and general formula 11;

wherein general formula 6 has the formula:

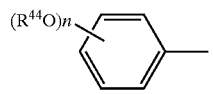

wherein general formula 7 has the formula:

wherein general formula 8 has the formula:

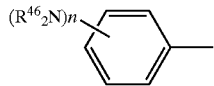

wherein general formula 9 has the formula:

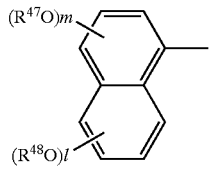

wherein general formula 10 has the formula:

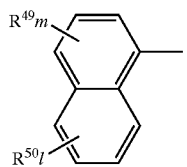

wherein general formula 11 has the formula:

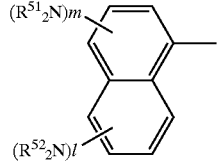

wherein $R^{44}$, $R^{45}$, and $R^{46}$ are separately selected from the group consisting of a saturated or unsaturated hydrocarbon groups having one or more carbons, and a fluoroalkyl group; $R^{47}$, $R^{48}$, $R^{49}$, $R^{50}$, $R^{51}$, and $R^{52}$ are identical or different groups separately selected from the group consisting of a saturated or unsaturated hydrocarbon group having one or more carbons, and a fluoroalkyl group; n is an integer of 0 to 5; m is an integer of 0 to 3; l is an integer of 0 to 3; and $R^{69}$ is selected from the group consisting of a hydrogen atom, a saturated or unsaturated hydrocarbon group, and an aryl group which may have a substituent;

wherein said compound is obtained by condensing a 4-(N,N-diarylamino)benzaldehyde having a general formula 38:

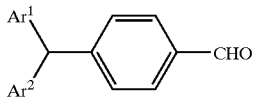

wherein $Ar^1$ and $Ar^2$ are identical or different aryl groups which may have a substituent selected from the group consisting of general formula 6, general formula 7, general formula 8, general formula 9, general formula 10, and general formula 11;

wherein general formula 6 has the formula:

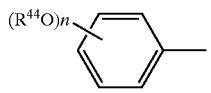

wherein general formula 7 has the formula:

wherein general formula 8 has the formula:

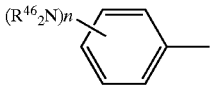

wherein general formula 9 has the formula:

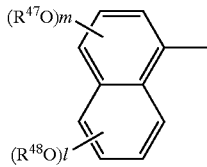

wherein general formula 10 has the formula:

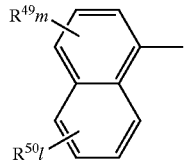

wherein general formula 11 has the formula:

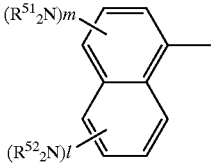

wherein $R^{44}$, $R^{45}$, and $R^{46}$ each represent a saturated or unsaturated hydrocarbon group having one or more carbons; $R^{47}$, $R^{48}$, $R^{49}$, $R^{50}$, $R^{51}$, and $R^{52}$ are identical or different groups separately selected from the group consisting of a saturated or unsaturated hydrocarbon group having one or more carbons, and a fluoroalkyl group; n is an integer of 0 to 5; m is an integer of 0 to 3; l is an integer of 0 to 3;

with a phosphonic ester having a general formula 39:

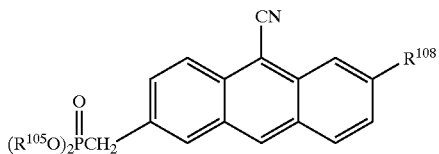

or, in the alternative, a phosphonium salt having a general formula 40:

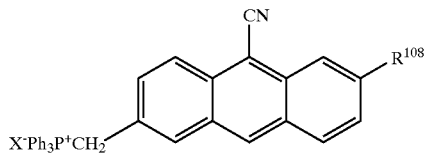

wherein and $R^{108}$ is selected from the group consisting of $R^5$, $R^{16}$, $R^{25}$, and $R^{42}$; and X is a halogen atom.

22. A process for producing an aminostyrylanthracene compound according to claim 21 wherein $R^{44}$, $R^{45}$, $R^{46}$, $R^{47}$, $R^{48}$, $R^{49}$, $R^{50}$, $R^{51}$, and $R^{52}$ each represent a group having 1 to 6 carbons.

23. A process for producing an aminostyrylanthracene compound according to claim 21 wherein said process gives an aminostyrylanthracene compound represented by a formula selected from the group consisting of general formula 21, general formula 22, general formula 23, general formula 24, general formula 25, general formula 26, and general formula 27;

wherein general formula 21 has the formula:

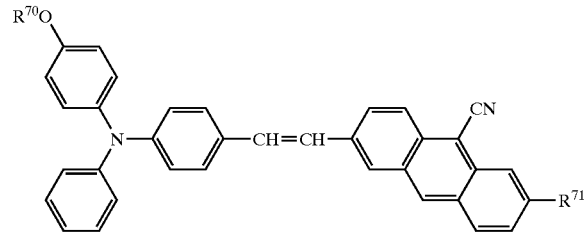

wherein $R^{70}$ is selected from the group consisting of a saturated or unsaturated hydrocarbon group having 1 to 6 carbons, and an aryl group which may have a substituent; $R^{71}$ is selected from the group consisting of a hydrogen atom, a saturated or unsaturated hydrocarbon group having 1 to 6 carbons, and an aryl group which may have a substituent;

wherein general formula 22 has the formula:

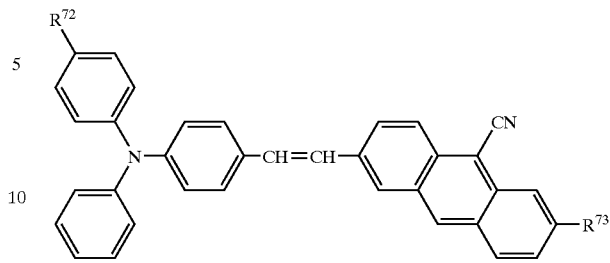

wherein $R^{72}$ is selected from the group consisting of a saturated or unsaturated hydrocarbon group having 1 to 6 carbons, a trifluoromethyl group, and an aryl group which may have a substituent; $R^{73}$ is selected from the group consisting of a hydrogen atom, a saturated or unsaturated hydrocarbon group having 1 to 6 carbons, and an aryl group which may have a substituent;

wherein general formula 23 has the formula:

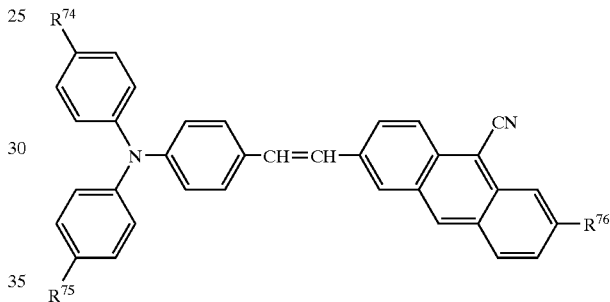

wherein $R^{74}$ and $R^{75}$ are separately selected from the group consisting of a saturated or unsaturated hydrocarbon group having 1 to 6 carbons, a trifluoromethyl group, and an aryl group which may have a substituent; $R^{76}$ is selected from the group consisting of a hydrogen atom, a saturated or unsaturated hydrocarbon group having 1 to 6 carbons, and an aryl group which may have a substituent;

wherein general formula 24 has the formula:

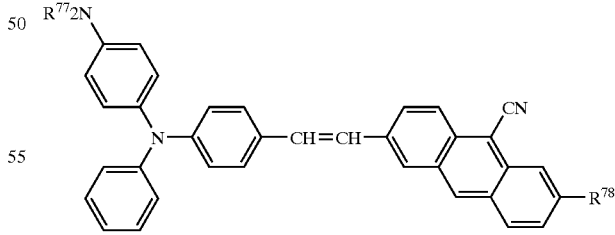

wherein $R^{77}$ is selected from the group consisting of a saturated or unsaturated hydrocarbon group having 1 to 6 carbons, and an aryl group which may have a substituent; $R^{78}$ is selected from the group consisting of a hydrogen atom, a saturated or unsaturated hydrocarbon group having 1 to 6 carbons, and an aryl group which may have a substituent;

wherein general formula 25 has the formula:

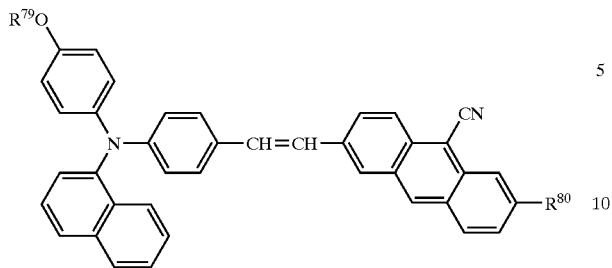

wherein $R^{79}$ is selected from the group consisting of a saturated or unsaturated hydrocarbon group having 1 to 6 carbons, and an aryl group which may have a substituent; $R^{80}$ is selected from the group consisting of a hydrogen atom, a saturated or unsaturated hydrocarbon group having 1 to 6 carbons, and an aryl group which may have a substituent;

wherein general formula 26 has the formula:

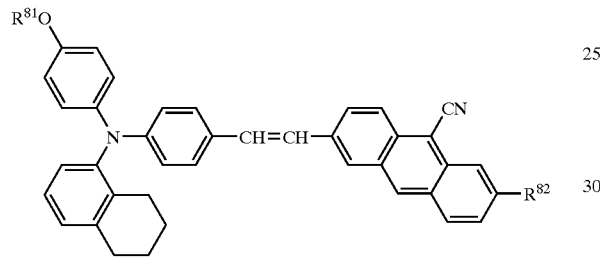

wherein $R^{81}$ is selected from the group consisting of a saturated or unsaturated hydrocarbon group having 1 to 6 carbons, and an aryl group which may have a substituent; $R^{82}$ is selected from the group consisting of a hydrogen atom, a saturated or unsaturated hydrocarbon group having 1 to 6 carbons, and an aryl group which may have a substituent;

wherein general formula 27 has the formula:

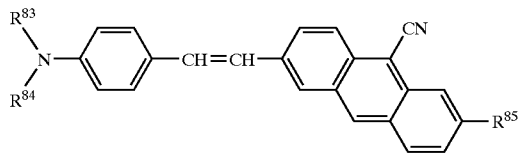

wherein $R^{83}$ and $R^{84}$ are separately selected from the group consisting of a saturated or unsaturated hydrocarbon group having 1 to 6 carbons, and an aryl group which may have a substituent; $R^{85}$ is selected from the group consisting of a hydrogen atom, a saturated or unsaturated hydrocarbon group having 1 to 6 carbons, and an aryl group which may have a substituent.

24. A process for producing an aminostyrylanthracene compound according to claim 21 wherein said process gives an aminostyrylanthracene compound represented by a formula selected from the group consisting of structural formula 28-1, structural formula 28-2, structural formula 28-3, structural formula 28-4, structural formula 28-5, structural formula 28-6, structural formula 28-7, structural formula 28-8, structural formula 28-9, structural formula 28-10, structural formula 28-11, and structural formula 28-12;

wherein structural formula 28-1 has the formula:

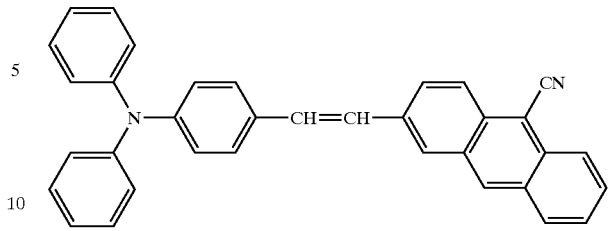

wherein structural formula 28-2 has the formula:

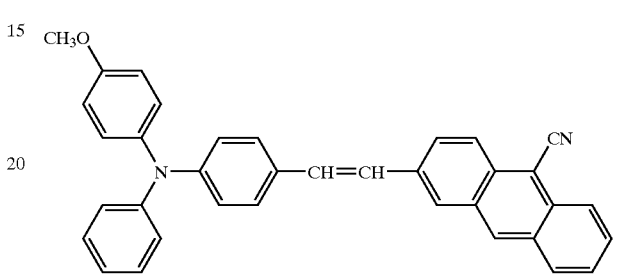

wherein structural formula 28-3 has the formula:

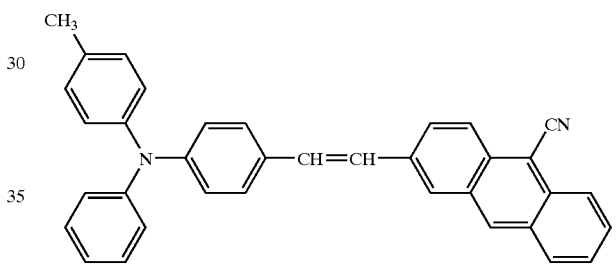

wherein structural formula 28-4 has the formula:

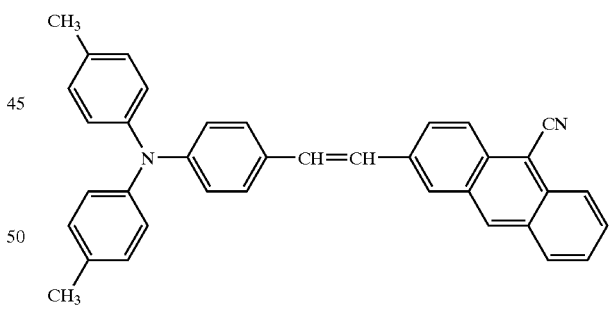

wherein structural formula 28-5 has the formula:

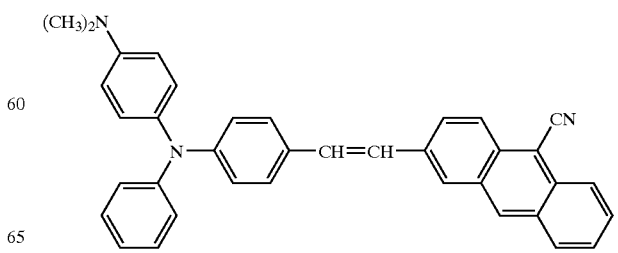

wherein structural formula 28-6 has the formula:

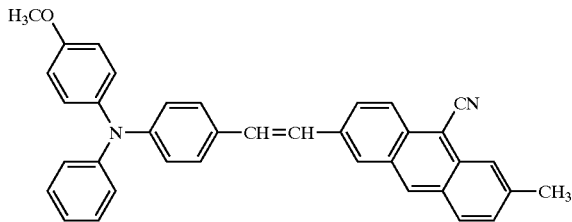

wherein structural formula 28-7 has the formula:

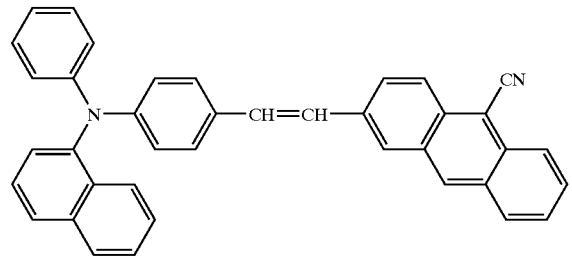

wherein structural formula 28-8 has the formula:

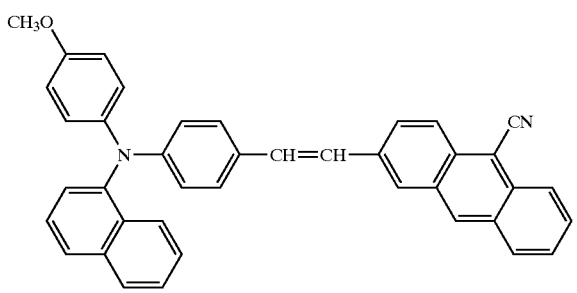

wherein structural formula 28-9 has the formula:

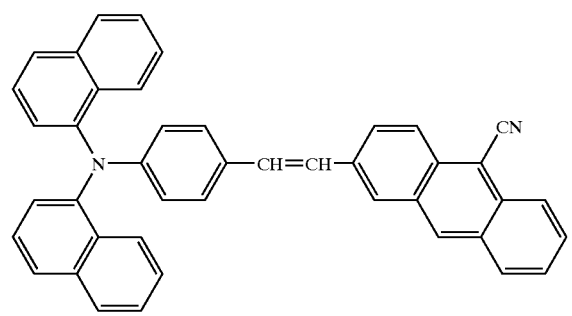

wherein structural formula 28-10 has the formula:

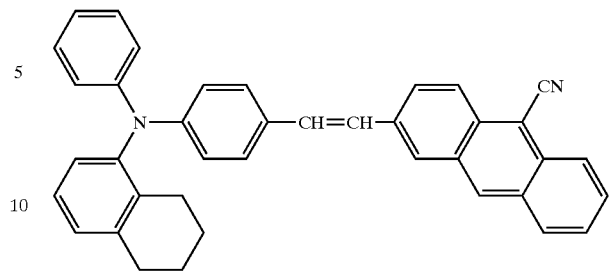

wherein structural formula 28-11 has the formula: and

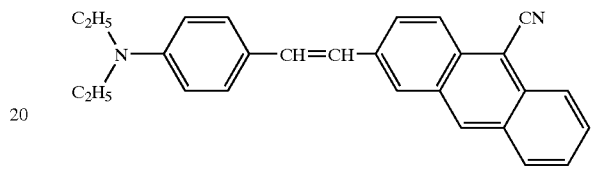

wherein structural formula 28-12 has the formula:

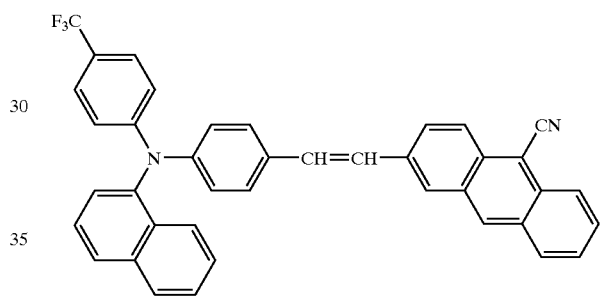

25. A process for producing an aminostyrylanthracene compound according to claim 14 wherein an aminostyrylanthracene compound is represented by general formula 29 having the formula:

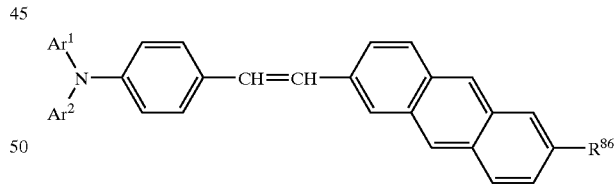

wherein $Ar^1$ and $Ar^2$ are identical or different aryl groups which may have a substituent wherein said substituent is selected from the group consisting of general formula 6, general formula 7, general formula 8, general formula 9, general formula 10, and general formula 11; wherein general formula 6 has the formula:

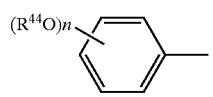

wherein general formula 7 has the formula:

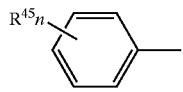

wherein general formula 8 has the formula:

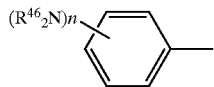

wherein general formula 9 has the formula:

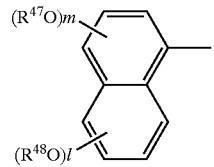

wherein general formula 10 has the formula:

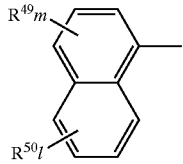

wherein general formula 11 has the formula:

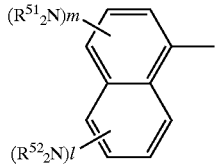

wherein $R^{44}$, $R^{45}$, and $R^{46}$ are separately selected from the group consisting of a saturated or unsaturated hydrocarbon groups having one or more carbons, and a fluoroalkyl group; $R^{47}$, $R^{48}$, $R^{49}$, $R^{50}$, $R^{51}$, and $R^{52}$ are identical or different groups separately selected from the group consisting of a saturated or unsaturated hydrocarbon group having one or more carbons, and a fluoroalkyl group; n is an integer of 0 to 5; m is an integer of 0 to 3; 1 is an integer of 0 to 3; and $R^{86}$ is selected from the group consisting of a hydrogen atom, a saturated or unsaturated hydrocarbon group, and an aryl group which may have a substituent;

wherein said compound is obtained by condensing a 4-(N,N-diarylamino)benzaldehyde having a general formula 38:

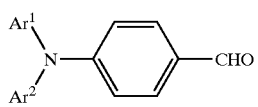

wherein $Ar^1$ and $Ar^2$ are identical or different aryl groups which may have a substituent selected from the group consisting of general formula 6, general formula 7, general formula 8, general formula 9, general formula 10, and general formula 11;

wherein general formula 6 has the formula:

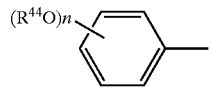

wherein general formula 7 has the formula:

wherein general formula 8 has the formula:

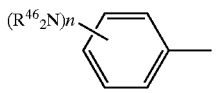

wherein general formula 9 has the formula:

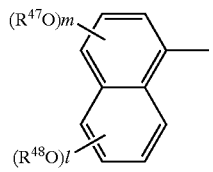

wherein general formula 10 has the formula:

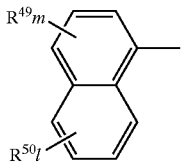

wherein general formula 11 has the formula:

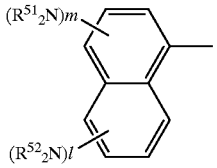

wherein $R^{44}$, $R^{45}$, and $R^{46}$ each represent a saturated or unsaturated hydrocarbon group having one or more carbons; $R^{47}$, $R^{48}$, $R^{49}$, $R^{50}$, $R^{51}$, and $R^{52}$ are identical or different groups separately selected from the group consisting of a saturated or unsaturated hydrocarbon group having one or more carbons, and a fluoroalkyl group; n is an integer of 0 to 5; m is an integer of 0 to 3; l is an integer of 0 to 3;
with a phosphonic ester having a general formula 43:

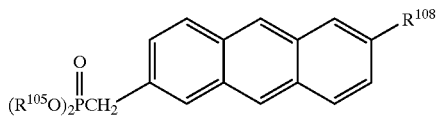

or, in the alternative, a phosphonium salt having a general formula 44:

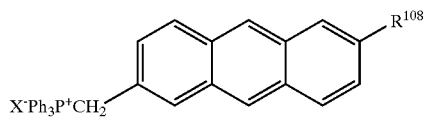

wherein; and $R^{108}$ is selected from the group consisting of $R^5$, $R^{16}$, $R^{25}$, and $R^{42}$; and X is a halogen atom.

26. A process for producing an aminostyrylanthracene compound according to claim 25 wherein $R^{44}$, $R^{45}$, $R^{46}$, $R^{47}$, $R^{48}$, $R^{49}$, $R^{50}$, $R^{51}$, and $R^{52}$ each represent a groups having 1 to 6 carbons.

27. A process for producing an aminostyrylanthracene compound according to claim 25 wherein said process gives an aminostyrylanthracene compound represented by a formula selected from the group consisting of general formula 30, general formula 31, general formula 32, general formula 33, general formula 34, general formula 35, and general formula 36;

wherein general formula 30 has the formula:

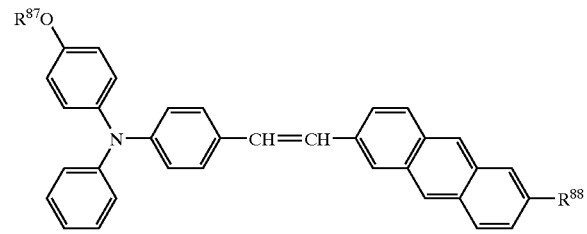

wherein $R^{87}$ is selected from the group consisting of a saturated or unsaturated hydrocarbon group having 1 to 6 carbons, and an aryl group which may have a substituent; $R^{88}$ is selected from the group consisting of a hydrogen atom, a saturated or unsaturated hydrocarbon group having 1 to 6 carbons, and an aryl group which may have a substituent;

wherein general formula 31 has the formula:

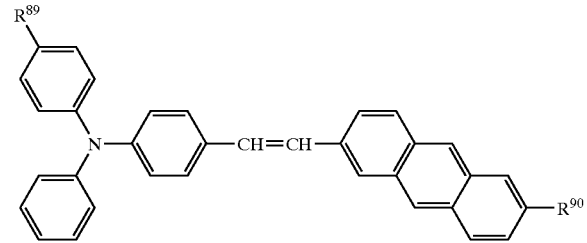

wherein $R^{89}$ is selected from the group consisting of a saturated or unsaturated hydrocarbon group having 1 to 6 carbons, a trifluoromethyl group, and an aryl group which may have a substituent; $R^{90}$ is selected from the group consisting of a hydrogen atom, a saturated or unsaturated hydrocarbon group having 1 to 6 carbons, and an aryl group which may have a substituent;

wherein general formula 32 has the formula:

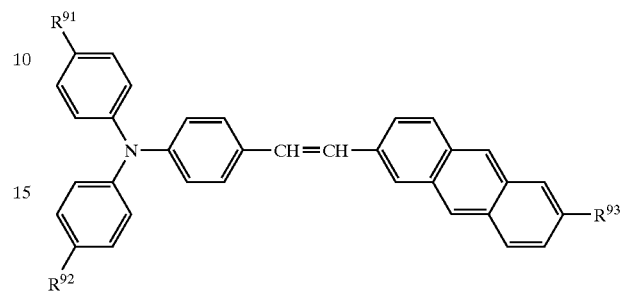

wherein $R^{91}$ and $R^{92}$ are separately selected from the group consisting of a saturated or unsaturated hydrocarbon group having 1 to 6 carbons, a trifluoromethyl group, and an aryl group which may have a substituent; $R^{93}$ is selected from the group consisting of a hydrogen atom, a saturated or unsaturated hydrocarbon group having 1 to 6 carbons, and an aryl group which may have a substituent;

wherein general formula 33 has the formula:

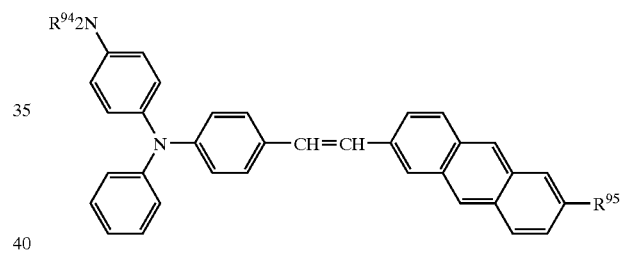

wherein $R^{94}$ is selected from the group consisting of a saturated or unsaturated hydrocarbon group having 1 to 6 carbons, and an aryl group which may have a substituent; $R^{95}$ is selected from the group consisting of a hydrogen atom, a saturated or unsaturated hydrocarbon group having 1 to 6 carbons, and an aryl group which may have a substituent;

wherein general formula 34 has the formula:

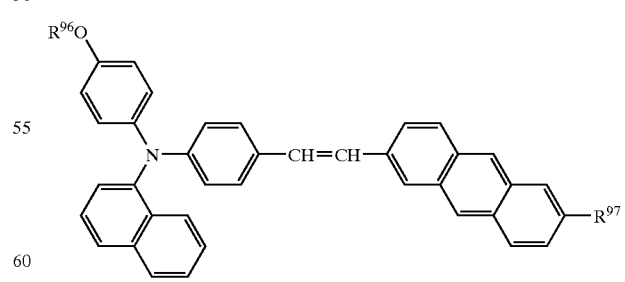

wherein $R^{96}$ is selected from the group consisting of a saturated or unsaturated hydrocarbon group having 1 to 6 carbons, and an aryl group which may have a substituent; $R^{97}$ is selected from the group consisting of a hydrogen atom, a saturated or unsaturated hydrocar bon group having 1 to 6 carbons, and an aryl group which may have a substituent;

wherein general formula 35 has the formula:

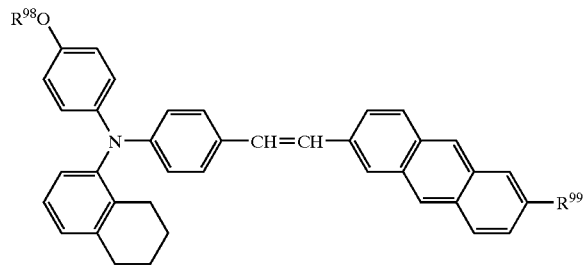

wherein $R^{98}$ is selected from the group consisting of a saturated or unsaturated hydrocarbon group having 1 to 6 carbons, and an aryl group which may have a substituent; $R^{99}$ is selected from the group consisting of a hydrogen atom, a saturated or unsaturated hydrocarbon group having 1 to 6 carbons, and an aryl group which may have a substituent;

wherein general formula 36 has the formula:

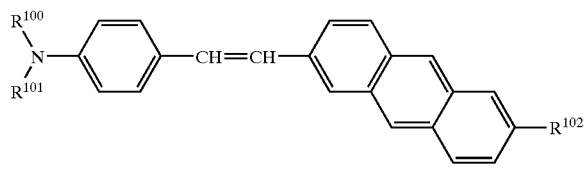

wherein $R^{100}$ and $R^{101}$ are separately selected from the group consisting of a saturated or unsaturated hydrocarbon group having 1 to 6 carbons, and an aryl group which may have a substituent; $R^{102}$ is selected from the group consisting of a hydrogen atom, a saturated or unsaturated hydrocarbon group having 1 to 6 carbons, and an aryl group which may have a substituent.

28. A process for producing an aminostyrylanthracene compound according to claim 25 wherein said process gives an aminostyrylanthracene compound represented by a formula selected from the group consisting of structural formula 37-1, structural formula 37-2, structural formula 37-3, structural formula 37-4, structural formula 37-5, structural formula 37-6, structural formula 37-7, structural formula 37-8, structural formula 37-9, structural formula 37-10, structural formula 37-11, and structural formula 37-12;

wherein structural formula 37-1 has the formula:

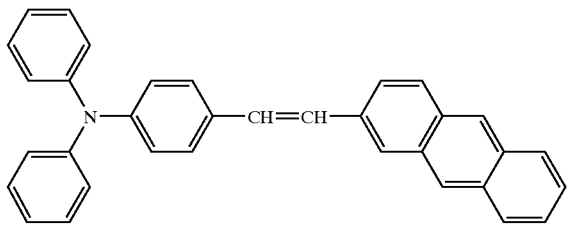

wherein structural formula 37-2 has the formula:

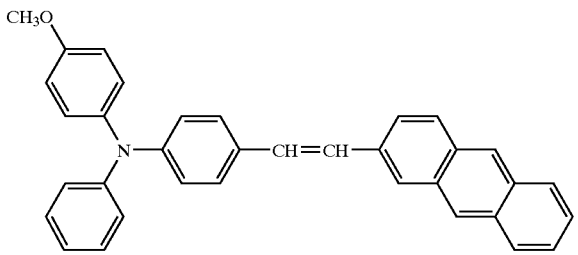

wherein structural formula 37-3 has the formula:

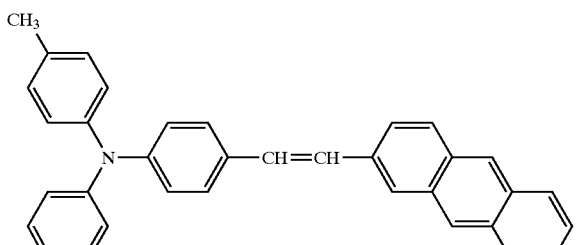

wherein structural formula 37-4 has the formula:

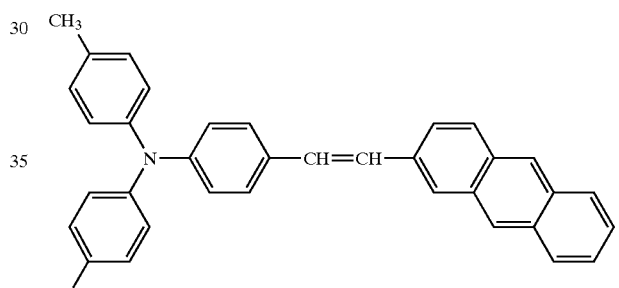

wherein structural formula 37-5 has the formula:

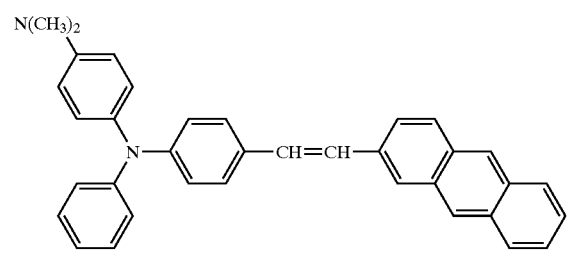

wherein structural formula 37-6 has the formula:

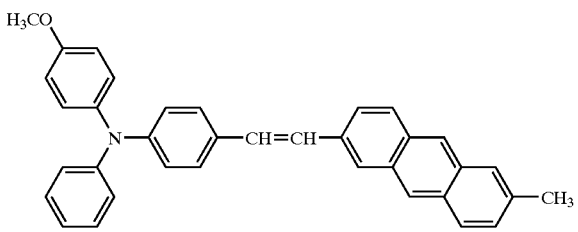

wherein structural formula 37-7 has the formula:
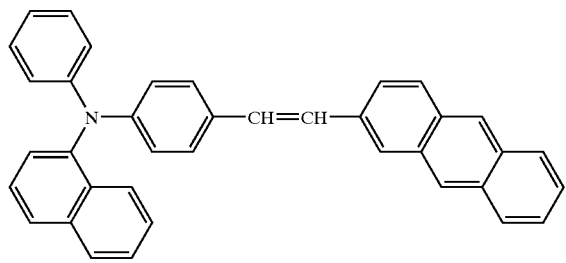
wherein structural formula 37-8 has the formula:
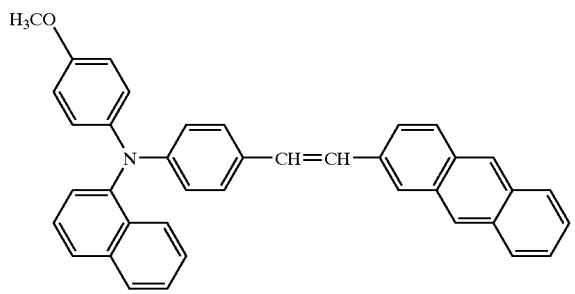
wherein structural formula 37-9 has the formula:
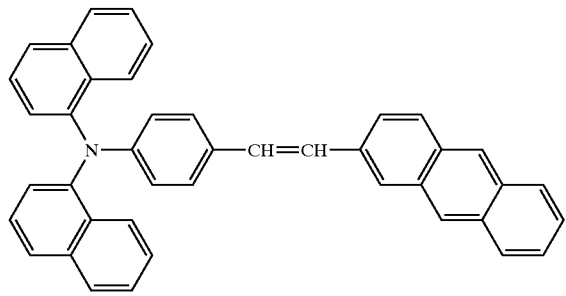
wherein structural formula 37-10 has the formula:
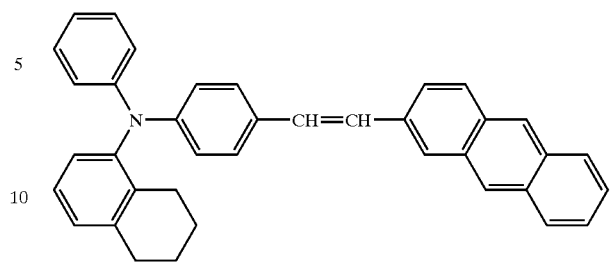
wherein structural formula 37-11 has the formula: and
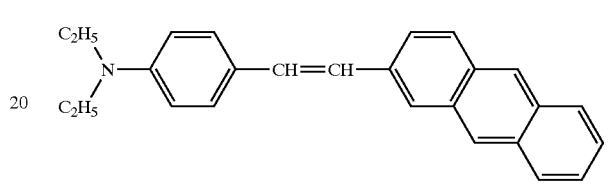
wherein structural formula 37-12 has the formula:
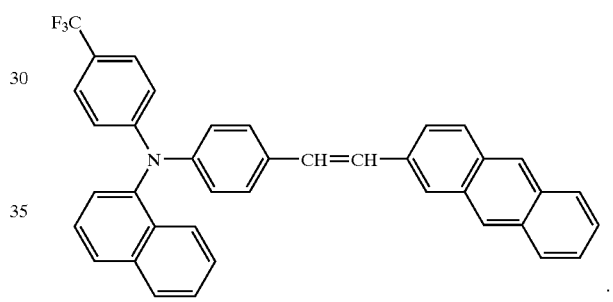
* * * * *